United States Patent [19]

Dougherty et al.

[11] Patent Number: 5,583,021
[45] Date of Patent: Dec. 10, 1996

[54] PRODUCTION OF VIRUS RESISTANT PLANTS

[75] Inventors: William G. Dougherty, Philomath, Oreg.; John A. Lindbo, Kent, Wash.

[73] Assignee: The State of Oregon Acting by and Through the State Board of Higher Education on Behalf of Oregon State University, Eugene, Oreg.

[21] Appl. No.: 271,829

[22] Filed: Jul. 7, 1994

Related U.S. Application Data

[63] Continuation-in-part of Ser. No. 838,509, Feb. 19, 1992, abandoned.

[51] Int. Cl.$^6$ .......................... C12N 15/83; C12N 15/33; A01H 5/00
[52] U.S. Cl. .................... 435/172.3; 435/240.4; 435/252.3; 435/320.1; 536/23.72; 800/205
[58] Field of Search ........................ 435/172.3, 240.4, 435/252.3, 320.1; 536/23.72; 800/205

[56] References Cited

U.S. PATENT DOCUMENTS 4,970,168  11/1990  Tumer .............................. 435/317.1

FOREIGN PATENT DOCUMENTS

65749/90  5/1991  Australia .

OTHER PUBLICATIONS

Allison et al., "Biochemical Analysis of the Capsid Protein Gene and capsid Protein of Tobacco Etch Virus: N–Terminal Amino Acids Are Located on the Virion's Surface," *Virology* 147:309–316 (1985).
Allison et al., "The Nucleotide siquence of the Coding Region of Tobacco Etch Virus Genomic RNA: Evidence for the Syntheisis of a Single Polyprotein," *Virology* 154:9–20 (1986).
Allison et al., "Sequence Determination of the Capsid Protein Gene and Flanking Regions of Tobacco Etch Virus: Evidence for Synthesis and Processing of a Polyprotein in Potyvirus Genome Expression," *Proc. Natl. Acad. Sci. USA* 82:3969–3972 (1985).
Baulcombe, "Strategies for virus resistance in plants," *Trends in Genetics* 5(2):56–60 (1989).
Beachy et al., "Coat Protein–Mediated Resistance Against Virus Infection," *Annu. Rev. Phytopathol.* 28:451–474 (1990).
Carrington, J. and Dougherty, W., "Small Nuclear Inclusion Protein Encoded by a Plant Potyvirus Genome Is A Protease," *J. Virol.* 61:2540–2548 (1987).
Carrington et al., "Vectors for Cell–Free Expression and Mutagenesis of Protein–Coding Sequences," *Nucl. Acids Res.* 15:10066 (1987).
Clark et al., "Tissue–Specific Expression of the TMV Coat Protein in Transgenic Tobacco Plants Affects the Level of Coat Protein–Mediated Virus Protection," *Virology* 179:640–647 (1990).
Day et al., "Expression of an antisense viral gene in transgenic tobacco confers resistance to the DNA virus tomato golden mosaic virus," *Proc. Natl. Acad. Sci. USA* 88:6721–6725 (1991).
Golemboski et al., "Plants Transformed with a Tobacco Mosaic Virus Nonstructural Gene Sequence Are Resistant to the Virus," *Proc. Natl. Acad. Sci. USA* 87:6311–6315 (1990).
Hemenway et al., "Anaylsis of the Mechanism of Protection in Transgenic Plants Expressing the Potato Virus X Coat Protein or Its Antisense RNA," *Embo J.* 7:1273–1280 (1988).
Hollings and Brunt, "Potyvirus Group," *CMI/AAB Descriptions of Plant Viruses* 245 (1981).
Kawchuk et al., "Sense and Antisense RNA–Mediated Resistance to Potato Leafroll Virus in Russet Burbank Potato Plants," *Mol. Plant–Mirobe Intractns* 4:247–253 (1991).
Lawson et al., "Engineering Resistance to Mixed Virus Infection in a Commercial Potato Cultivar: Resistance to Potato Virus X and Potato Virus Y in Transgenic Russet Burbank," *Bio/Technology* 8:127–134 (1990).
Lindbo et al., "Pathogen–derived resistance to a potyvirus; immune and resistant phenotypes in transgenic tobacco expressing altered forms of a potyvirus coat protein nucleotide sequence," *Molecular Plant–Microbe Interactions,* 5(2):144–153 (1992).
Lindbo et al., "Untranslatable transcript of the tobacco etch virus coat protein gene sequence can interfere with tobacco etch virus replication in transgenic plants and protoplasts," *Virology,* 189(2):725–733 (1992).
Ling et al., "Protection Against Detrimental Effects of Potyvirus Infection in Trasgenic Tobacco Plants Expressing the Papaya Ringspot Virus Coat Protein Gene," *Bio/Technology* 9:752–758 (1991).

(List continued on next page.)

Primary Examiner—Patricia R. Moody
Attorney, Agent, or Firm—Klarquist Sparkman Campbell Leigh & Whinston, LLP

[57] ABSTRACT

A method of suppressing virus gene expression in plants using untranslatable plus sense RNA is disclosed. The method is useful for the production of plants that are resistant to virus infection.

29 Claims, 8 Drawing Sheets

OTHER PUBLICATIONS

Loesch–Fries et al., "Expression of Alfalfa Mosaic Virus RNA 4 in Transgenic Plants Confers Virus Resistance," *Embo J.* 6:1845–1851 (1987).

Marsh et al., "Artificial Defective Interfering RNAs Derived From Brome Mosaic Virus," *J. of Gen. Virology* 72:1787–1792 (1991).

Nelson et al., "Lesions and Virus Accumulation in Inoculated Transgenic Tobacco Plants Expressing the Coat Protein Gene of Tobacco Mosaic Virus," *Virology* 158:126–132 (1987).

Powell et al., "Protection Against Tobacco Mosaic Virus Infection in Transgenic Plants Requires Accumulation of Coat Protein Rather Than Coat Protein RNA Sequences," *Virology* 175:124–130 (1990).

Stark, D. and Beachy, R., "Protection Against Potyvirus Infection in Trasgenic Plants: Evidence for Broad Spectrum Resistance," *Bio/Technology* 7:1257–1262 (1989).

van der Wilk et al., "Expression of the Potato Leafroll Luteovirus Coat Protein Gene in Transgenic Potato Plants Inhibits Viral Infection," *Plant Mol. Biol.* 17:431–439 (1991).

Jorgenson 1990 Trends in Biotech 8:340–344.

van der Vlugt et al. 1992 Plant Molec Biol. 20:631–639.

Grierson et al. 1991 (Apr.) Trends in Biotech 9:122–123.

deltaan et al 1992 Bio/Technology 10:1133–1137.

Mol et al 1991 (Jun.) Trends in biotech 9:182–183.

Farinelli et al 1992 Bio/Technology 10:1020–1025.

Hull et al 1992 Critical Reviews in Plant Sciences 11(1):17–33.

Pang et al 1993 (INJul.) Bio/Technology 11:819.

Goelet et al 1982 Proc Natl Acad Sci USA 79:5818–5822.

Lindbo et al 1993 Encyclopedia of Virology vol. 3 pp. 1148–1153.

FIG. 4   TEV Coat Protein Gene Constructs Inserted into Nicotiana tabacum cv. Burley 49

| Plant Line | Construct | Products in Transgenic Plants | Plant Type |
|---|---|---|---|
| 35S | Enh 35S — CaMV 5' UTS — CaMV 3' UTS | RNA transcript of CaMV UTS | Could not be determined |
| FL | Enh 35S — CaMV 5' UTS — Full Length Coat protein gene — CaMV 3' UTS | RNA transcript and 30 kDa Protein | Slightly dwarf phenotype Oval leaves |
| ΔN29 | Enh 35S — CaMV 5' UTS — ΔN29 Coat protein gene — CaMV 3' UTS | RNA transcript and 26 kDa Protein | Slightly dwarf phenotype Oval leaves |
| ΔC18 | Enh 35S — CaMV 5' UTS — ΔC18 Coat protein gene (TAG) — CaMV 3' UTS | RNA transcript and 27 kDa Protein | Dwarfed phenotype Shortened internodes Round leaves |
| ΔC118 | Enh 35S — CaMV 5' UTS — ΔC118 Coat protein gene (TAG) — CaMV 3' UTS | RNA transcript | Slightly dwarf phenotype Oval leaves |
| ΔN/C | Enh 35S — CaMV 5' UTS — ΔN/C Coat protein gene (TAG) — CaMV 3' UTS | RNA transcript and 24 kDa Protein | Dwarfed phenotype Shortened internodes Round leaves |
| AS | Enh 35S — CaMV 5' UTS — Full Length Coat protein gene (reverse) — CaMV 3' UTS | Antisense RNA | Could not be determined |
| RC | Enh 35S — CaMV 5' UTS (TGA TGA TAG) — Full Length Coat protein gene — CaMV 3' UTS | Untranslatable sense RNA | Good burley type |
| 2RC | Enh 35S — TEV 5' UTS (TGA TGA TAG) — Full Length Coat protein gene — tml 3' UTS | Untranslatable sense RNA | Good burley type |

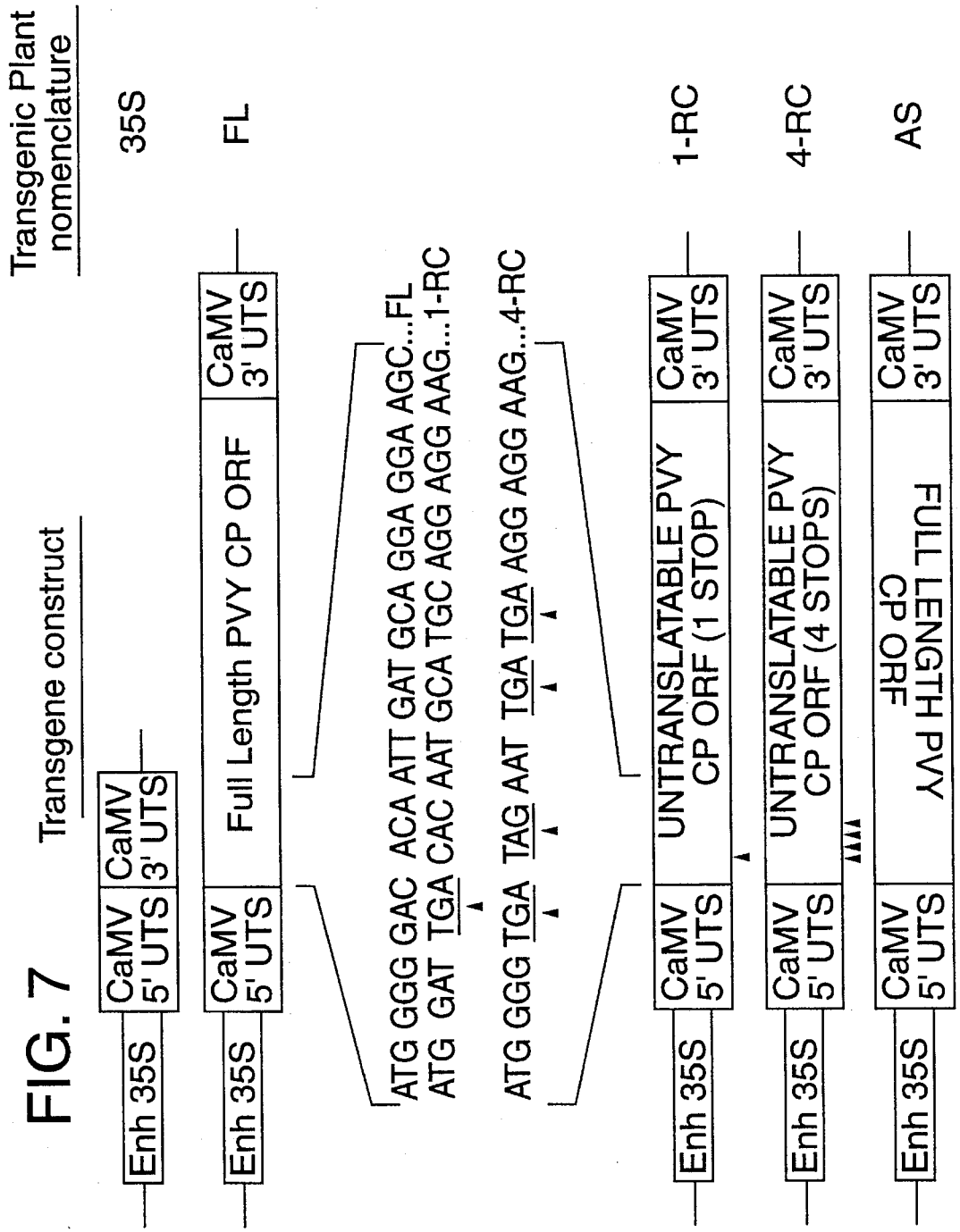

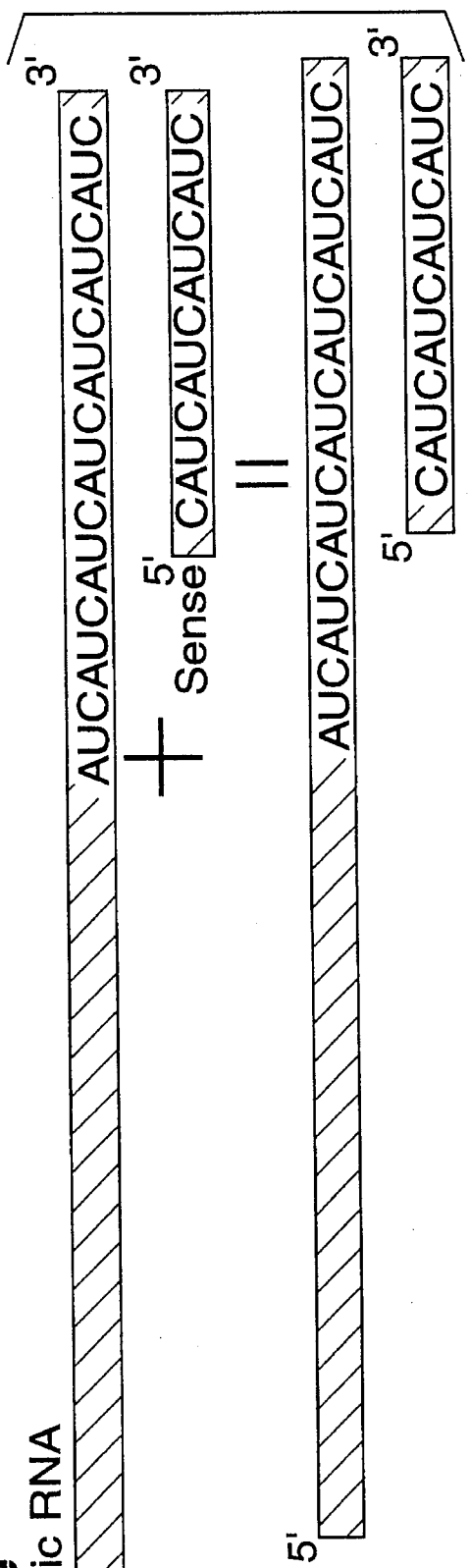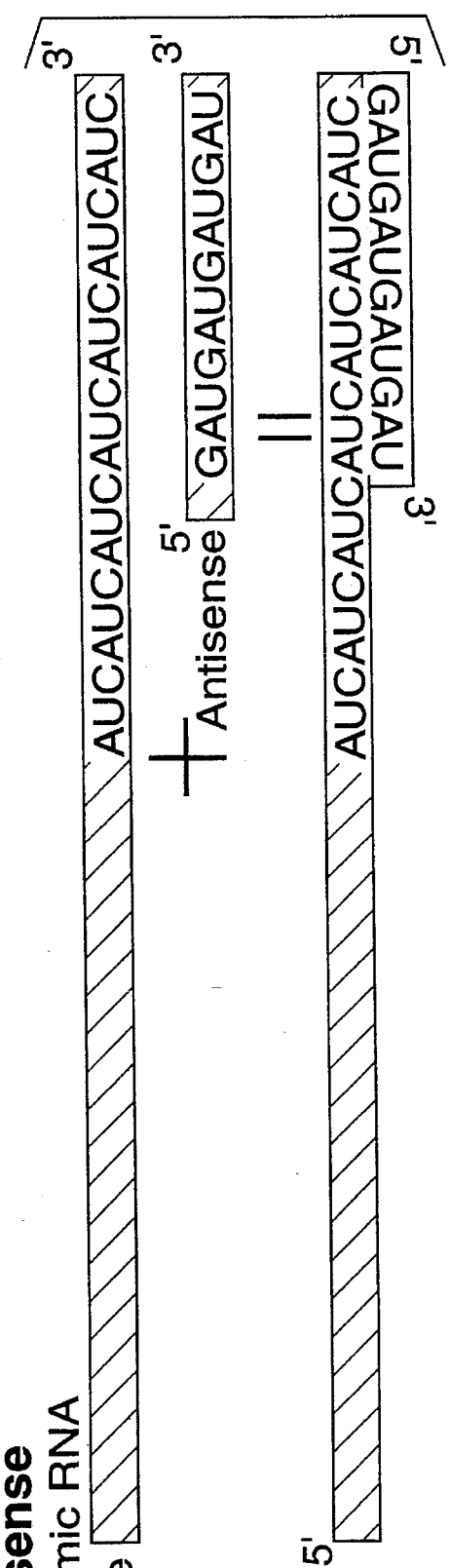

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
      ( A ) LENGTH: 9495
      ( B ) TYPE: Nucleic Acid
      ( C ) STRANDEDNESS: Single
      ( D ) TOPOLOGY: Linear ( i i ) MOLECULE TYPE:
      ( A ) DESCRIPTION: cDNA to genomic RNA ( i i i ) HYPOTHETICAL: No ( i v ) ANTI-SENSE: No ( v ) FRAGMENT TYPE: N/A ( v i ) ORIGINAL SOURCE:
      ( A ) ORGANISM: Tobacco Etch Virus (TEV)
      ( B ) STRAIN: Highly Aphid Transmitted
         ( H A T )

( v i i ) IMMEDIATE SOURCE: TEV propagated in N. tabacum Burley 49

( v i i i ) POSITION IN GENOME: N/A ( i x ) FEATURE:
( A ) NAME/KEY: Coat protein gene
( B ) LOCATION: Genomic nucleotides 8518 - 9306
( C ) IDENTIFICATION METHOD: --
( D ) OTHER INFORMATION: SEQ. ID No. 1 is the cDNA corresponding to the Tobacco Etch Virus Genome.

( x ) PUBLICATION INFORMATION:
( A ) AUTHORS: Allison et al.
( B ) TITLE: The nucleotide sequence of the coding region of Tobacco Etch Virus Genomic RNA: Evidence for the Synthesis of a Single Polyprotein
( C ) JOURNAL: Virology
( D ) VOLUME: 154
( E ) ISSUE: --
( F ) PAGES: 9-20

( x i ) SEQUENCE DESCRIPTION: SEQ ID NO: 1:

```
NAAATAACAA ATCTCAACAC AACATATACA AAACAAACGA ATCTCAAGCA ATCAAGCATT      60

CTACTTCTAT TGCAGCAATT TAAATCATTT CTTTTAAAGC AAAAGCAATT TTCTGAAAAT     120

TTTCACCATT TACGAACGAT AGCA ATG GCA CTG ATC TTT GGC ACA GTC AAC GCT    174
                           Met Ala Leu Ile Phe Gly Thr Val Asn Ala
                             1               5                  10

AAC ATC CTG AAG GAA GTG TTC GGT GGA GCT CGT ATG GCT TGC GTT ACC       222
Asn Ile Leu Lys Glu Val Phe Gly Gly Ala Arg Met Ala Cys Val Thr
                 15                  20                  25

AGC GCA CAT ATG GCT GGA GCG AAT GGA AGC ATT TTG AAG AAG GCA GAA       270
Ser Ala His Met Ala Gly Ala Asn Gly Ser Ile Leu Lys Lys Ala Glu
```

|  |  |  |  |  | 30 |  |  |  |  | 35 |  |  |  |  | 40 |  |  |
|---|---|---|---|---|---|---|---|---|---|---|---|---|---|---|---|---|---|

```
GAG  ACC  TCT  CGT  GCA  ATC  ATG  CAC  AAA  CCA  GTG  ATC  TTC  GGA  GAA  GAC       318
Glu  Thr  Ser  Arg  Ala  Ile  Met  His  Lys  Pro  Val  Ile  Phe  Gly  Glu  Asp
          45                       50                       55

TAC  ATT  ACC  GAG  GCA  GAC  TTG  CCT  TAC  ACA  CCA  CTC  CAT  TTA  GAG  GTC       366
Tyr  Ile  Thr  Glu  Ala  Asp  Leu  Pro  Tyr  Thr  Pro  Leu  His  Leu  Glu  Val
          60                       65                       70

GAT  GCT  GAA  ATG  GAG  CGG  ATG  TAT  TAT  CTT  GGT  CGT  CGC  GCG  CTC  ACC       414
Asp  Ala  Glu  Met  Glu  Arg  Met  Tyr  Tyr  Leu  Gly  Arg  Arg  Ala  Leu  Thr
75                       80                       85                       90

CAT  GGC  AAG  AGA  CGC  AAA  GTT  TCT  GTG  AAT  AAC  AAG  AGG  AAC  AGG  AGA       462
His  Gly  Lys  Arg  Arg  Lys  Val  Ser  Val  Asn  Asn  Lys  Arg  Asn  Arg  Arg
               95                       100                      105

AGG  AAA  GTG  GCC  AAA  ACG  TAC  GTG  GGG  CGT  GAT  TCC  ATT  GTT  GAG  AAG       510
Arg  Lys  Val  Ala  Lys  Thr  Tyr  Val  Gly  Arg  Asp  Ser  Ile  Val  Glu  Lys
               110                      115                      120

ATT  GTA  GTG  CCC  CAC  ACC  GAG  AGA  AAG  GTT  GAT  ACC  ACA  GCA  GCA  GTG       558
Ile  Val  Val  Pro  His  Thr  Glu  Arg  Lys  Val  Asp  Thr  Thr  Ala  Ala  Val
               125                      130                      135

GAA  GAC  ATT  TGC  AAT  GAA  GCT  ACC  ACT  CAA  CTT  GTG  CAT  AAT  AGT  ATG       606
Glu  Asp  Ile  Cys  Asn  Glu  Ala  Thr  Thr  Gln  Leu  Val  His  Asn  Ser  Met
140                      145                      150

CCA  AAG  CGT  AAG  AAG  CAG  AAA  AAC  TTC  TTG  CCC  GCC  ACT  TCA  CTA  AGT       654
Pro  Lys  Arg  Lys  Lys  Gln  Lys  Asn  Phe  Leu  Pro  Ala  Thr  Ser  Leu  Ser
155                      160                      165                      170

AAC  GTG  TAT  GCC  CAA  ACT  TGG  AGC  ATA  GTG  CGC  AAA  CGC  CAT  ATG  CAG       702
Asn  Val  Tyr  Ala  Gln  Thr  Trp  Ser  Ile  Val  Arg  Lys  Arg  His  Met  Gln
               175                      180                      185

GTG  GAG  ATC  ATT  AGC  AAG  AAG  AGC  GTC  CGA  GCG  AGG  GTC  AAG  AGA  TTT       750
Val  Glu  Ile  Ile  Ser  Lys  Lys  Ser  Val  Arg  Ala  Arg  Val  Lys  Arg  Phe
               190                      195                      200

GAG  GGC  TCG  GTG  CAA  TTG  TTC  GCA  AGT  GTG  CGT  CAC  ATG  TAT  GGC  GAG       798
Glu  Gly  Ser  Val  Gln  Leu  Phe  Ala  Ser  Val  Arg  His  Met  Tyr  Gly  Glu
               205                      210                      215

AGG  AAA  AGG  GTG  GAC  TTA  CGT  ATT  GAC  AAC  TGG  CAG  CAA  GAG  ACA  CTT       846
Arg  Lys  Arg  Val  Asp  Leu  Arg  Ile  Asp  Asn  Trp  Gln  Gln  Glu  Thr  Leu
220                      225                      230

CTA  GAC  CTT  GCT  AAA  AGA  TTT  AAG  AAT  GAG  AGA  GTG  GAT  CAA  TCG  AAG       894
Leu  Asp  Leu  Ala  Lys  Arg  Phe  Lys  Asn  Glu  Arg  Val  Asp  Gln  Ser  Lys
235                      240                      245                      250

CTC  ACT  TTT  GGT  TCA  AGT  GGC  CTA  GTT  TTG  AGG  CAA  GGC  TCG  TAC  GGA       942
Leu  Thr  Phe  Gly  Ser  Ser  Gly  Leu  Val  Leu  Arg  Gln  Gly  Ser  Tyr  Gly
               255                      260                      265

CCT  GCG  CAT  TGG  TAT  CGA  CAT  GGT  ATG  TTC  ATT  GTA  CGC  GGT  CGG  TCG       990
Pro  Ala  His  Trp  Tyr  Arg  His  Gly  Met  Phe  Ile  Val  Arg  Gly  Arg  Ser
               270                      275                      280

GAT  GGG  ATG  TTG  GTG  GAT  GCT  CGT  GCG  AAG  GTA  ACG  TTC  GCT  GTT  TGT      1038
Asp  Gly  Met  Leu  Val  Asp  Ala  Arg  Ala  Lys  Val  Thr  Phe  Ala  Val  Cys
               285                      290                      295

CAC  TCA  ATG  ACA  CAT  TAT  AGC  GAC  AAA  TCA  ATC  TCT  GAG  GCA  TTC  TTC      1086
His  Ser  Met  Thr  His  Tyr  Ser  Asp  Lys  Ser  Ile  Ser  Glu  Ala  Phe  Phe
     300                      305                      310

ATA  CCA  TAC  TCT  AAG  AAA  TTC  TTG  GAG  TTG  AGA  CCA  GAT  GGA  ATC  TCC      1134
Ile  Pro  Tyr  Ser  Lys  Lys  Phe  Leu  Glu  Leu  Arg  Pro  Asp  Gly  Ile  Ser
315                      320                      325                      330

CAT  GAG  TGT  ACA  AGA  GGA  GTA  TCA  GTT  GAG  CGG  TGC  GGT  GAG  GTG  GCT      1182
His  Glu  Cys  Thr  Arg  Gly  Val  Ser  Val  Glu  Arg  Cys  Gly  Glu  Val  Ala
                    335                      340                      345

GCA  ATC  CTG  ACA  CAA  GCA  CTT  TCA  CCG  TGT  GGT  AAG  ATC  ACA  TGC  AAA      1230
Ala  Ile  Leu  Thr  Gln  Ala  Leu  Ser  Pro  Cys  Gly  Lys  Ile  Thr  Cys  Lys
```

|     |     |     |     |     | 350 |     |     |     |     | 355 |     |     |     |     | 360 |     |      |
|-----|-----|-----|-----|-----|-----|-----|-----|-----|-----|-----|-----|-----|-----|-----|-----|-----|------|
| CGT | TGC | ATG | GTT | GAA | ACA | CCT | GAC | ATT | GTT | GAG | GGT | GAG | TCG | GGA | GAA |     | 1278 |
| Arg | Cys | Met | Val | Glu | Thr | Pro | Asp | Ile | Val | Glu | Gly | Glu | Ser | Gly | Glu |     |      |
|     |     | 365 |     |     |     | 370 |     |     |     |     | 375 |     |     |     |     |     |      |

| AGT | GTC | ACC | AAC | CAA | GGT | AAG | CTC | CTA | GCA | ATG | CTG | AAA | GAA | CAG | TAT | 1326 |
|-----|-----|-----|-----|-----|-----|-----|-----|-----|-----|-----|-----|-----|-----|-----|-----|------|
| Ser | Val | Thr | Asn | Gln | Gly | Lys | Leu | Leu | Ala | Met | Leu | Lys | Glu | Gln | Tyr |      |
|     | 380 |     |     |     |     | 385 |     |     |     |     | 390 |     |     |     |     |      |

| CCA | GAT | TTC | CCA | ATG | GCC | GAG | AAA | CTA | CTC | ACA | AGG | TTT | TTG | CAA | CAG | 1374 |
|-----|-----|-----|-----|-----|-----|-----|-----|-----|-----|-----|-----|-----|-----|-----|-----|------|
| Pro | Asp | Phe | Pro | Met | Ala | Glu | Lys | Leu | Leu | Thr | Arg | Phe | Leu | Gln | Gln |      |
| 395 |     |     |     | 400 |     |     |     |     | 405 |     |     |     |     |     | 410 |      |

| AAA | TCA | CTA | GTA | AAT | ACA | AAT | TTG | ACA | GCC | TGC | GTG | AGC | GTC | AAA | CAA | 1422 |
|-----|-----|-----|-----|-----|-----|-----|-----|-----|-----|-----|-----|-----|-----|-----|-----|------|
| Lys | Ser | Leu | Val | Asn | Thr | Asn | Leu | Thr | Ala | Cys | Val | Ser | Val | Lys | Gln |      |
|     |     |     |     | 415 |     |     |     | 420 |     |     |     |     | 425 |     |     |      |

| CTC | ATT | GGT | GAC | CGC | AAA | CAA | GCT | CCA | TTC | ACA | CAC | GTA | CTG | GCT | GTC | 1470 |
|-----|-----|-----|-----|-----|-----|-----|-----|-----|-----|-----|-----|-----|-----|-----|-----|------|
| Leu | Ile | Gly | Asp | Arg | Lys | Gln | Ala | Pro | Phe | Thr | His | Val | Leu | Ala | Val |      |
|     |     |     | 430 |     |     |     |     | 435 |     |     |     |     | 440 |     |     |      |

| AGC | GAA | ATT | CTG | TTT | AAA | GGC | AAT | AAA | CTA | ACA | GGG | GCT | GAT | CTC | GAA | 1518 |
|-----|-----|-----|-----|-----|-----|-----|-----|-----|-----|-----|-----|-----|-----|-----|-----|------|
| Ser | Glu | Ile | Leu | Phe | Lys | Gly | Asn | Lys | Leu | Thr | Gly | Ala | Asp | Leu | Glu |      |
|     |     |     | 445 |     |     |     |     | 450 |     |     |     |     | 455 |     |     |      |

| GAG | GCA | AGC | ACA | CAT | ATG | CTT | GAA | ATA | GCA | AGG | TTC | TTG | AAC | AAT | CGC | 1566 |
|-----|-----|-----|-----|-----|-----|-----|-----|-----|-----|-----|-----|-----|-----|-----|-----|------|
| Glu | Ala | Ser | Thr | His | Met | Leu | Glu | Ile | Ala | Arg | Phe | Leu | Asn | Asn | Arg |      |
|     | 460 |     |     |     |     | 465 |     |     |     |     | 470 |     |     |     |     |      |

| ACT | GAA | AAT | ATG | CGC | ATT | GGC | CAC | CTT | GGT | TCT | TTC | AGA | AAT | AAA | ATC | 1614 |
|-----|-----|-----|-----|-----|-----|-----|-----|-----|-----|-----|-----|-----|-----|-----|-----|------|
| Thr | Glu | Asn | Met | Arg | Ile | Gly | His | Leu | Gly | Ser | Phe | Arg | Asn | Lys | Ile |      |
| 475 |     |     |     |     | 480 |     |     |     |     | 485 |     |     |     |     | 490 |      |

| TCA | TCG | AAG | GCC | CAT | GTG | AAT | AAC | GCA | CTC | ATG | TGT | GAT | AAT | CAA | CTT | 1662 |
|-----|-----|-----|-----|-----|-----|-----|-----|-----|-----|-----|-----|-----|-----|-----|-----|------|
| Ser | Ser | Lys | Ala | His | Val | Asn | Asn | Ala | Leu | Met | Cys | Asp | Asn | Gln | Leu |      |
|     |     |     |     | 495 |     |     |     |     | 500 |     |     |     |     | 505 |     |      |

| GAT | CAG | AAT | GGG | AAT | TTT | ATT | TGG | GGA | CTA | AGG | GGT | GCA | CAC | GCA | AAG | 1710 |
|-----|-----|-----|-----|-----|-----|-----|-----|-----|-----|-----|-----|-----|-----|-----|-----|------|
| Asp | Gln | Asn | Gly | Asn | Phe | Ile | Trp | Gly | Leu | Arg | Gly | Ala | His | Ala | Lys |      |
|     |     |     | 510 |     |     |     |     | 515 |     |     |     |     | 520 |     |     |      |

| AGG | TTT | CTT | AAA | GGA | TTT | TTC | ACT | GAG | ATT | GAC | CCA | AAT | GAA | GGA | TAC | 1758 |
|-----|-----|-----|-----|-----|-----|-----|-----|-----|-----|-----|-----|-----|-----|-----|-----|------|
| Arg | Phe | Leu | Lys | Gly | Phe | Phe | Thr | Glu | Ile | Asp | Pro | Asn | Glu | Gly | Tyr |      |
|     |     | 525 |     |     |     |     | 530 |     |     |     |     | 535 |     |     |     |      |

| GAT | AAG | TAT | GTT | ATC | AGG | AAA | CAT | ATC | AGG | GGT | AGC | AGA | AAG | CTA | GCA | 1806 |
|-----|-----|-----|-----|-----|-----|-----|-----|-----|-----|-----|-----|-----|-----|-----|-----|------|
| Asp | Lys | Tyr | Val | Ile | Arg | Lys | His | Ile | Arg | Gly | Ser | Arg | Lys | Leu | Ala |      |
| 540 |     |     |     |     | 545 |     |     |     |     | 550 |     |     |     |     |     |      |

| ATT | GGC | AAT | TTG | ATA | ATG | TCA | ACT | GAC | TTC | CAG | ACG | CTC | AGG | CAA | CAA | 1854 |
|-----|-----|-----|-----|-----|-----|-----|-----|-----|-----|-----|-----|-----|-----|-----|-----|------|
| Ile | Gly | Asn | Leu | Ile | Met | Ser | Thr | Asp | Phe | Gln | Thr | Leu | Arg | Gln | Gln |      |
| 555 |     |     |     |     | 560 |     |     |     |     | 565 |     |     |     |     | 570 |      |

| ATT | CAA | GGC | GAA | ACT | ATT | GAG | CGT | AAA | GAA | ATT | GGG | AAT | CAC | TGC | ATT | 1902 |
|-----|-----|-----|-----|-----|-----|-----|-----|-----|-----|-----|-----|-----|-----|-----|-----|------|
| Ile | Gln | Gly | Glu | Thr | Ile | Glu | Arg | Lys | Glu | Ile | Gly | Asn | His | Cys | Ile |      |
|     |     |     |     | 575 |     |     |     |     | 580 |     |     |     |     | 585 |     |      |

| TCA | ATG | CGG | AAT | GGT | AAT | TAC | GTG | TAC | CCA | TGT | TGT | TGT | GTT | ACT | CTT | 1950 |
|-----|-----|-----|-----|-----|-----|-----|-----|-----|-----|-----|-----|-----|-----|-----|-----|------|
| Ser | Met | Arg | Asn | Gly | Asn | Tyr | Val | Tyr | Pro | Cys | Cys | Cys | Val | Thr | Leu |      |
|     |     |     | 590 |     |     |     |     | 595 |     |     |     |     | 600 |     |     |      |

| GAA | GAT | GGT | AAG | GCT | CAA | TAT | TCG | GAT | CTA | AAG | CAC | CCA | ACG | AAG | AGA | 1998 |
|-----|-----|-----|-----|-----|-----|-----|-----|-----|-----|-----|-----|-----|-----|-----|-----|------|
| Glu | Asp | Gly | Lys | Ala | Gln | Tyr | Ser | Asp | Leu | Lys | His | Pro | Thr | Lys | Arg |      |
|     |     | 605 |     |     |     |     | 610 |     |     |     |     | 615 |     |     |     |      |

| CAT | CTG | GTC | ATT | GGC | AAC | TCT | GGC | GAT | TCA | AAG | TAC | CTA | GAC | CTT | CCA | 2046 |
|-----|-----|-----|-----|-----|-----|-----|-----|-----|-----|-----|-----|-----|-----|-----|-----|------|
| His | Leu | Val | Ile | Gly | Asn | Ser | Gly | Asp | Ser | Lys | Tyr | Leu | Asp | Leu | Pro |      |
|     | 620 |     |     |     |     | 625 |     |     |     |     | 630 |     |     |     |     |      |

| GTT | CTC | AAT | GAA | GAG | AAA | ATG | TAT | ATA | GCT | AAT | GAA | GGT | TAT | TGC | TAC | 2094 |
|-----|-----|-----|-----|-----|-----|-----|-----|-----|-----|-----|-----|-----|-----|-----|-----|------|
| Val | Leu | Asn | Glu | Glu | Lys | Met | Tyr | Ile | Ala | Asn | Glu | Gly | Tyr | Cys | Tyr |      |
| 635 |     |     |     |     | 640 |     |     |     |     | 645 |     |     |     |     | 650 |      |

| ATG | AAC | ATT | TTC | TTT | GCT | CTA | CTA | GTG | AAT | GTC | AAG | GAA | GAG | GAT | GCA | 2142 |
|-----|-----|-----|-----|-----|-----|-----|-----|-----|-----|-----|-----|-----|-----|-----|-----|------|
| Met | Asn | Ile | Phe | Phe | Ala | Leu | Leu | Val | Asn | Val | Lys | Glu | Glu | Asp | Ala |      |
|     |     |     |     | 655 |     |     |     |     | 660 |     |     |     |     | 665 |     |      |

| AAG | GAC | TTC | ACC | AAG | TTT | ATA | AGG | GAC | ACA | ATT | GTT | CCA | AAG | CTT | GGA | 2190 |
|-----|-----|-----|-----|-----|-----|-----|-----|-----|-----|-----|-----|-----|-----|-----|-----|------|
| Lys | Asp | Phe | Thr | Lys | Phe | Ile | Arg | Asp | Thr | Ile | Val | Pro | Lys | Leu | Gly |      |

-continued

| | | | 670 | | | | | 675 | | | | | 680 | | | |
|---|---|---|---|---|---|---|---|---|---|---|---|---|---|---|---|---|
| GCG | TGG | CCA | ACA | ATG | CAA | GAT | GTT | GCA | ACT | GCA | TGC | TAC | TTA | CTT | TCC | 2238 |
| Ala | Trp | Pro 685 | Thr | Met | Gln | Asp | Val 690 | Ala | Thr | Ala | Cys | Tyr 695 | Leu | Leu | Ser | |
| ATT | CTT | TAC | CCA | GAT | GTC | CTG | AGA | GCT | GAA | CTA | CCC | AGA | ATT | TTG | GTT | 2286 |
| Ile | Leu | Tyr 700 | Pro | Asp | Val | Leu 705 | Arg | Ala | Glu | Leu | Pro 710 | Arg | Ile | Leu | Val | |
| GAT | CAT | GAC | AAC | AAA | ACA | ATG | CAT | GTT | TTG | GAT | TCG | TAT | GGG | TCT | AGA | 2334 |
| Asp 715 | His | Asp | Asn | Lys | Thr 720 | Met | His | Val | Leu | Asp 725 | Ser | Tyr | Gly | Ser | Arg 730 | |
| ACG | ACA | GGA | TAC | CAC | ATG | TTG | AAA | ATG | AAC | ACA | ACA | TCC | CAG | CTA | ATT | 2382 |
| Thr | Thr | Gly | Tyr | His 735 | Met | Leu | Lys | Met | Asn 740 | Thr | Thr | Ser | Gln | Leu 745 | Ile | |
| GAA | TTC | GTT | CAT | TCA | GGT | TTG | GAA | TCC | GAA | ATG | AAA | ACT | TAC | AAT | GTT | 2430 |
| Glu | Phe | Val | His | Ser 750 | Gly | Leu | Glu | Ser | Glu 755 | Met | Lys | Thr | Tyr | Asn 760 | Val | |
| GGA | GGG | ATG | AAC | CGA | GAT | GTG | GTC | ACA | CAA | GGT | GCA | ATT | GAG | ATG | TTG | 2478 |
| Gly | Gly | Met 765 | Asn | Arg | Asp | Val | Val 770 | Thr | Gln | Gly | Ala | Ile 775 | Glu | Met | Leu | |
| ATC | AAG | TCT | ATA | TAC | AAA | CCA | CAT | CTC | ATG | AAG | CAG | TTA | CTT | GAG | GAA | 2526 |
| Ile | Lys | Ser 780 | Ile | Tyr | Lys | Pro | His 785 | Leu | Met | Lys | Gln | Leu 790 | Leu | Glu | Glu | |
| GAG | CCA | TAC | ATA | ATT | GTC | CTG | GCA | ATA | GTC | TCC | CCT | TCA | ATT | TTA | ATT | 2574 |
| Glu 795 | Pro | Tyr | Ile | Ile | Val 800 | Leu | Ala | Ile | Val | Ser 805 | Pro | Ser | Ile | Leu | Ile 810 | |
| GCC | ATG | TAC | AAC | TCT | GGA | ACT | TTT | GAG | CAG | GCG | TTA | CAA | ATG | TGG | TTG | 2622 |
| Ala | Met | Tyr | Asn | Ser 815 | Gly | Thr | Phe | Glu | Gln 820 | Ala | Leu | Gln | Met | Trp 825 | Leu | |
| CCA | AAT | ACA | ATG | AGG | TTA | GCT | AAC | CTC | GCT | GCC | ATC | TTG | TCA | GCC | TTA | 2670 |
| Pro | Asn | Thr | Met 830 | Arg | Leu | Ala | Asn | Leu 835 | Ala | Ala | Ile | Leu | Ser 840 | Ala | Leu | |
| GCG | CAA | AAG | TTA | ACT | TTG | GCA | GAT | TTG | TTC | GTC | CAG | CAG | CGT | AAT | TTG | 2718 |
| Ala | Gln | Lys 845 | Leu | Thr | Leu | Ala | Asp 850 | Leu | Phe | Val | Gln | Gln 855 | Arg | Asn | Leu | |
| ATT | AAT | GAG | TAT | GCG | CAG | GTA | ATT | TTG | GAC | AAT | CTG | ATT | GAC | GGT | GTC | 2766 |
| Ile | Asn | Glu 860 | Tyr | Ala | Gln | Val | Ile 865 | Leu | Asp | Asn | Leu | Ile 870 | Asp | Gly | Val | |
| AGG | GTT | AAT | CAT | TCG | CTA | TCC | CTA | GCA | ATG | GAA | ATT | GTT | ACT | ATT | AAG | 2814 |
| Arg 875 | Val | Asn | His | Ser | Leu 880 | Ser | Leu | Ala | Met | Glu 885 | Ile | Val | Thr | Ile | Lys 890 | |
| CTG | GCC | ACC | CAA | GAG | ATG | GAC | ATG | GCG | TTG | AGG | GAA | GGT | GGC | TAT | GCT | 2862 |
| Leu | Ala | Thr | Gln | Glu 895 | Met | Asp | Met | Ala | Leu 900 | Arg | Glu | Gly | Gly | Tyr 905 | Ala | |
| GTG | ACC | TCT | GAA | AAG | GTG | CAT | GAA | ATG | TTG | GAA | AAA | AAC | TAT | GTA | AAG | 2910 |
| Val | Thr | Ser | Glu | Lys 910 | Val | His | Glu | Met | Leu 915 | Glu | Lys | Asn | Tyr | Val 920 | Lys | |
| GCT | TTG | AAG | GAT | GCA | TGG | GAC | GAA | TTA | ACT | TGG | TTG | GAA | AAA | TTC | TCC | 2958 |
| Ala | Leu | Lys 925 | Asp | Ala | Trp | Asp | Glu 930 | Leu | Thr | Trp | Leu | Glu 935 | Lys | Phe | Ser | |
| GCA | ATC | AGG | CAT | TCA | AGA | AAG | CTC | TTG | AAA | TTT | GGG | CGA | AAG | CCT | TTA | 3006 |
| Ala | Ile 940 | Arg | His | Ser | Arg | Lys 945 | Leu | Leu | Lys | Phe | Gly 950 | Arg | Lys | Pro | Leu | |
| ATC | ATG | AAA | AAC | ACC | GTA | GAT | TGC | GGC | GGA | CAT | ATA | GAC | TTG | TCT | GTG | 3054 |
| Ile | Met | Lys | Asn 955 | Thr | Val 960 | Asp | Cys | Gly | Gly | His 965 | Ile | Asp | Leu | Ser | Val 970 | |
| AAA | TCG | CTT | TTC | AAG | TTC | CAC | TTG | GAA | CTC | CTG | AAG | GGA | ACC | ATC | TCA | 3102 |
| Lys | Ser | Leu | Phe | Lys 975 | Phe | His | Leu | Glu | Leu 980 | Leu | Lys | Gly | Thr | Ile 985 | Ser | |
| AGA | GCC | GTA | AAT | GGT | GGC | GCA | AGA | AAG | GTA | AGA | GTA | GCG | AAG | AAT | GCC | 3150 |
| Arg | Ala | Val | Asn | Gly | Gly | Ala | Arg | Lys | Val | Arg | Val | Ala | Lys | Asn | Ala | |

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|         |         |         | 990     |         |         |         |         | 995     |         |         |         |         | 1000    |         |         |      |
| ATG     | ACA     | AAA     | GGG     | GTT     | TTT     | CTC     | AAA     | ATC     | TAC     | AGC     | ATG     | CTT     | CCT     | GAC     | GTC     | 3198 |
| Met     | Thr     | Lys     | Gly     | Val     | Phe     | Leu     | Lys     | Ile     | Tyr     | Ser     | Met     | Leu     | Pro     | Asp     | Val     |      |
|         |         |         | 1005    |         |         |         |         | 1010    |         |         |         |         | 1015    |         |         |      |
| TAC     | AAG     | TTT     | ATC     | ACA     | GTC     | TCG     | AGT     | GTC     | CTT     | TCC     | TTG     | TTG     | TTG     | ACA     | TTC     | 3246 |
| Tyr     | Lys     | Phe     | Ile     | Thr     | Val     | Ser     | Ser     | Val     | Leu     | Ser     | Leu     | Leu     | Leu     | Thr     | Phe     |      |
|         |         |         | 1020    |         |         |         |         | 1025    |         |         |         |         | 1030    |         |         |      |
| TTA     | TTT     | CAA     | ATT     | GAC     | TGC     | ATG     | ATA     | AGG     | GCA     | CAC     | CGA     | GAG     | GCG     | AAG     | GTT     | 3294 |
| Leu     | Phe     | Gln     | Ile     | Asp     | Cys     | Met     | Ile     | Arg     | Ala     | His     | Arg     | Glu     | Ala     | Lys     | Val     |      |
| 1035    |         |         |         |         | 1040    |         |         |         |         | 1045    |         |         |         |         | 1050    |      |
| GCT     | GCA     | CAG     | TTG     | CAG     | AAA     | GAG     | AGC     | GAG     | TGG     | GAC     | AAT     | ATC     | ATC     | AAT     | AGA     | 3342 |
| Ala     | Ala     | Gln     | Leu     | Gln     | Lys     | Glu     | Ser     | Glu     | Trp     | Asp     | Asn     | Ile     | Ile     | Asn     | Arg     |      |
|         |         |         |         | 1055    |         |         |         |         | 1060    |         |         |         |         | 1065    |         |      |
| ACT     | TTC     | CAG     | TAT     | TCT     | AAG     | CTT     | GAA     | AAT     | CCT     | ATT     | GGC     | TAT     | CGC     | TCT     | ACA     | 3390 |
| Thr     | Phe     | Gln     | Tyr     | Ser     | Lys     | Leu     | Glu     | Asn     | Pro     | Ile     | Gly     | Tyr     | Arg     | Ser     | Thr     |      |
|         |         |         | 1070    |         |         |         |         | 1075    |         |         |         |         | 1080    |         |         |      |
| GCG     | GAG     | GAA     | AGA     | CTC     | CAA     | TCA     | GAA     | CAC     | CCC     | GAG     | GCT     | TTC     | GAG     | TAC     | TAC     | 3438 |
| Ala     | Glu     | Glu     | Arg     | Leu     | Gln     | Ser     | Glu     | His     | Pro     | Glu     | Ala     | Phe     | Glu     | Tyr     | Tyr     |      |
|         |         |         |         | 1085    |         |         |         |         | 1090    |         |         |         |         | 1095    |         |      |
| AAG     | TTT     | TGC     | ATT     | GGA     | AAG     | GAA     | GAC     | CTC     | GTT     | GAA     | CAG     | GCA     | AAA     | CAA     | CCG     | 3486 |
| Lys     | Phe     | Cys     | Ile     | Gly     | Lys     | Glu     | Asp     | Leu     | Val     | Glu     | Gln     | Ala     | Lys     | Gln     | Pro     |      |
|         |         |         | 1100    |         |         |         |         | 1105    |         |         |         |         | 1110    |         |         |      |
| GAG     | ATA     | GCA     | TAC     | TTT     | GAA     | AAG     | ATT     | ATA     | GCT     | TTC     | ATC     | ACA     | CTT     | GTA     | TTA     | 3534 |
| Glu     | Ile     | Ala     | Tyr     | Phe     | Glu     | Lys     | Ile     | Ile     | Ala     | Phe     | Ile     | Thr     | Leu     | Val     | Leu     |      |
| 1115    |         |         |         |         | 1120    |         |         |         |         | 1125    |         |         |         |         | 1130    |      |
| ATG     | GCT     | TTT     | GAC     | GCT     | GAG     | CGG     | AGT     | GAT     | GGA     | GTG     | TTC     | AAG     | ATA     | CTC     | AAT     | 3582 |
| Met     | Ala     | Phe     | Asp     | Ala     | Glu     | Arg     | Ser     | Asp     | Gly     | Val     | Phe     | Lys     | Ile     | Leu     | Asn     |      |
|         |         |         |         | 1135    |         |         |         |         | 1140    |         |         |         |         | 1145    |         |      |
| AAG     | TTC     | AAA     | GGA     | ATA     | CTG     | AGC     | TCA     | ACG     | GAG     | AGG     | GAG     | ATC     | ATC     | TAC     | ACG     | 3630 |
| Lys     | Phe     | Lys     | Gly     | Ile     | Leu     | Ser     | Ser     | Thr     | Glu     | Arg     | Glu     | Ile     | Ile     | Tyr     | Thr     |      |
|         |         |         | 1150    |         |         |         |         | 1155    |         |         |         |         | 1160    |         |         |      |
| CAG     | AGT     | TTG     | GAT     | GAT     | TAC     | GTT     | ACA     | ACC     | TTT     | GAT     | GAC     | AAT     | ATG     | ACA     | ATC     | 3678 |
| Gln     | Ser     | Leu     | Asp     | Asp     | Tyr     | Val     | Thr     | Thr     | Phe     | Asp     | Asp     | Asn     | Met     | Thr     | Ile     |      |
|         |         |         | 1165    |         |         |         |         | 1170    |         |         |         |         | 1175    |         |         |      |
| AAC     | CTC     | GAG     | TTG     | AAT     | ATG     | GAT     | GAA     | CTC     | CAC     | AAG     | ACG     | AGC     | CTT     | CCT     | GGA     | 3726 |
| Asn     | Leu     | Glu     | Leu     | Asn     | Met     | Asp     | Glu     | Leu     | His     | Lys     | Thr     | Ser     | Leu     | Pro     | Gly     |      |
|         |         |         | 1180    |         |         |         |         | 1185    |         |         |         |         | 1190    |         |         |      |
| GTC     | ACT     | TTT     | AAG     | CAA     | TGG     | TGG     | AAC     | AAC     | CAA     | ATC     | AGC     | CGA     | GGC     | AAC     | GTG     | 3774 |
| Val     | Thr     | Phe     | Lys     | Gln     | Trp     | Trp     | Asn     | Asn     | Gln     | Ile     | Ser     | Arg     | Gly     | Asn     | Val     |      |
| 1195    |         |         |         |         | 1200    |         |         |         |         | 1205    |         |         |         |         | 1210    |      |
| AAG     | CCA     | CAT     | TAT     | AGA     | ACT     | GAG     | GGG     | CAC     | TTC     | ATG     | GAG     | TTT     | ACC     | AGA     | GAT     | 3822 |
| Lys     | Pro     | His     | Tyr     | Arg     | Thr     | Glu     | Gly     | His     | Phe     | Met     | Glu     | Phe     | Thr     | Arg     | Asp     |      |
|         |         |         |         | 1215    |         |         |         |         | 1220    |         |         |         |         | 1225    |         |      |
| ACT     | GCG     | GCA     | TCG     | GTT     | GCC     | AGC     | GAG     | ATA     | TCA     | CAC     | TCA     | CCC     | GCA     | AGA     | GAT     | 3870 |
| Thr     | Ala     | Ala     | Ser     | Val     | Ala     | Ser     | Glu     | Ile     | Ser     | His     | Ser     | Pro     | Ala     | Arg     | Asp     |      |
|         |         |         | 1230    |         |         |         |         | 1235    |         |         |         |         | 1240    |         |         |      |
| TTT     | CTT     | GTG     | AGA     | GGT     | GCT     | GTT     | GGA     | TCT     | GGA     | AAA     | TCC     | ACA     | GGA     | CTT     | CCA     | 3918 |
| Phe     | Leu     | Val     | Arg     | Gly     | Ala     | Val     | Gly     | Ser     | Gly     | Lys     | Ser     | Thr     | Gly     | Leu     | Pro     |      |
|         |         |         | 1245    |         |         |         |         | 1250    |         |         |         |         | 1255    |         |         |      |
| TAC     | CAT     | TTA     | TCA     | AAG     | AGA     | GGG     | AGA     | GTG     | TTA     | ATG     | CTT     | GAG     | CCT     | ACC     | AGA     | 3966 |
| Tyr     | His     | Leu     | Ser     | Lys     | Arg     | Gly     | Arg     | Val     | Leu     | Met     | Leu     | Glu     | Pro     | Thr     | Arg     |      |
|         |         |         | 1260    |         |         |         |         | 1265    |         |         |         |         | 1270    |         |         |      |
| CCA     | CTC     | ACA     | GAT     | AAC     | ATG     | CAC     | AAG     | CAA     | CTG     | AGA     | AGT     | GAA     | CCA     | TTT     | AAC     | 4014 |
| Pro     | Leu     | Thr     | Asp     | Asn     | Met     | His     | Lys     | Gln     | Leu     | Arg     | Ser     | Glu     | Pro     | Phe     | Asn     |      |
| 1275    |         |         |         |         | 1280    |         |         |         |         | 1285    |         |         |         |         | 1290    |      |
| TGC     | TTC     | CCA     | ACT     | TTG     | AGG     | ATG     | AGA     | GGG     | AAG     | TCA     | ACT     | TTT     | GGG     | TCA     | TCA     | 4062 |
| Cys     | Phe     | Pro     | Thr     | Leu     | Arg     | Met     | Arg     | Gly     | Lys     | Ser     | Thr     | Phe     | Gly     | Ser     | Ser     |      |
|         |         |         | 1295    |         |         |         |         | 1300    |         |         |         |         | 1305    |         |         |      |
| CCG     | ATC     | ACA     | GTC     | ATG     | ACT     | AGT     | GGA     | TTC     | GCT     | TTA     | CAC     | CAC     | TTT     | GCA     | CGA     | 4110 |
| Pro     | Ile     | Thr     | Val     | Met     | Thr     | Ser     | Gly     | Phe     | Ala     | Leu     | His     | His     | Phe     | Ala     | Arg     |      |

|  |  |  |  |  |  |  |  |  |  |  |  |  |  |  |  |  |
|---|---|---|---|---|---|---|---|---|---|---|---|---|---|---|---|---|
|  |  |  |  | 1310 |  |  |  | 1315 |  |  |  | 1320 |  |  |  |  |
| AAC | ATA | GCT | GAG | GTA | AAA | ACA | TAC | GAT | TTT | GTC | ATA | ATT | GAT | GAA | TGT | 4158 |
| Asn | Ile | Ala | Glu | Val | Lys | Thr | Tyr | Asp | Phe | Val | Ile | Ile | Asp | Glu | Cys |  |
|  |  |  | 1325 |  |  |  |  | 1330 |  |  |  |  | 1335 |  |  |  |
| CAT | GTG | AAT | GAT | GCT | TCT | GCT | ATA | GCG | TTT | AGG | AAT | CTA | CTG | TTT | GAA | 4206 |
| His | Val | Asn | Asp | Ala | Ser | Ala | Ile | Ala | Phe | Arg | Asn | Leu | Leu | Phe | Glu |  |
|  | 1340 |  |  |  |  | 1345 |  |  |  |  | 1350 |  |  |  |  |  |
| CAT | GAA | TTT | GAA | GGA | AAA | GTC | CTC | AAA | GTG | TCA | GCC | ACA | CCA | CCA | GGT | 4254 |
| His | Glu | Phe | Glu | Gly | Lys | Val | Leu | Lys | Val | Ser | Ala | Thr | Pro | Pro | Gly |  |
| 1355 |  |  |  |  | 1360 |  |  |  |  | 1365 |  |  |  |  | 1370 |  |
| AGA | GAA | GTT | GAA | TTT | ACA | ACT | CAG | TTT | CCC | GTG | AAA | CTC | AAG | ATA | GAA | 4302 |
| Arg | Glu | Val | Glu | Phe | Thr | Thr | Gln | Phe | Pro | Val | Lys | Leu | Lys | Ile | Glu |  |
|  |  |  |  | 1375 |  |  |  |  | 1380 |  |  |  |  | 1385 |  |  |
| GAG | GCT | CTT | AGC | TTT | CAG | GAA | TTT | GTA | AGT | TTA | CAA | GGG | ACA | GGT | GCC | 4350 |
| Glu | Ala | Leu | Ser | Phe | Gln | Glu | Phe | Val | Ser | Leu | Gln | Gly | Thr | Gly | Ala |  |
|  |  |  | 1390 |  |  |  |  | 1395 |  |  |  |  | 1400 |  |  |  |
| AAC | GCC | GAT | GTG | ATT | AGT | TGT | GGC | GAC | AAC | ATA | CTA | GTA | TAT | GTT | GCT | 4398 |
| Asn | Ala | Asp | Val | Ile | Ser | Cys | Gly | Asp | Asn | Ile | Leu | Val | Tyr | Val | Ala |  |
|  |  |  | 1405 |  |  |  |  | 1410 |  |  |  |  | 1415 |  |  |  |
| AGC | TAC | AAT | GAT | GTT | GAT | AGT | CTT | GGC | AAG | CTC | CTT | GTG | CAA | AAG | GGA | 4446 |
| Ser | Tyr | Asn | Asp | Val | Asp | Ser | Leu | Gly | Lys | Leu | Leu | Val | Gln | Lys | Gly |  |
|  |  | 1420 |  |  |  |  | 1425 |  |  |  |  | 1430 |  |  |  |  |
| TAC | AAA | GTG | TCG | AAG | ATT | GAT | GGA | AGA | ACA | ATG | AAG | AGT | GGA | GGA | ACT | 4494 |
| Tyr | Lys | Val | Ser | Lys | Ile | Asp | Gly | Arg | Thr | Met | Lys | Ser | Gly | Gly | Thr |  |
| 1435 |  |  |  |  | 1440 |  |  |  |  | 1445 |  |  |  |  | 1450 |  |
| GAA | ATA | ATC | ACT | GAA | GGT | ACT | TCA | GTG | AAA | AAG | CAT | TTC | ATA | GTC | GCA | 4542 |
| Glu | Ile | Ile | Thr | Glu | Gly | Thr | Ser | Val | Lys | Lys | His | Phe | Ile | Val | Ala |  |
|  |  |  |  | 1455 |  |  |  |  | 1460 |  |  |  |  | 1465 |  |  |
| ACT | AAC | ATT | ATT | GAG | AAT | GGT | GTA | ACC | ATT | GAC | ATT | GAT | GTA | GTT | GTG | 4590 |
| Thr | Asn | Ile | Ile | Glu | Asn | Gly | Val | Thr | Ile | Asp | Ile | Asp | Val | Val | Val |  |
|  |  |  | 1470 |  |  |  |  | 1475 |  |  |  |  | 1480 |  |  |  |
| GAT | TTT | GGG | ACT | AAG | GTT | GTA | CCA | GTT | TTG | GAT | GTG | GAC | AAT | AGA | GCG | 4638 |
| Asp | Phe | Gly | Thr | Lys | Val | Val | Pro | Val | Leu | Asp | Val | Asp | Asn | Arg | Ala |  |
|  |  |  | 1481 |  |  |  |  | 1490 |  |  |  |  | 1495 |  |  |  |
| GTG | CAG | TAC | AAC | AAA | ACT | GTG | GTG | AGT | TAT | GGG | GAG | CGC | ATC | CAA | AAA | 4686 |
| Val | Gln | Tyr | Asn | Lys | Thr | Val | Val | Ser | Tyr | Gly | Glu | Arg | Ile | Gln | Lys |  |
|  |  |  | 1500 |  |  |  |  | 1505 |  |  |  |  | 1510 |  |  |  |
| CTC | GGT | AGA | GTT | GGG | CGA | CAC | AAG | GAA | GGA | GTA | GCA | CTT | CGA | ATT | GGC | 4734 |
| Leu | Gly | Arg | Val | Gly | Arg | His | Lys | Glu | Gly | Val | Ala | Leu | Arg | Ile | Gly |  |
| 1515 |  |  |  |  | 1520 |  |  |  |  | 1525 |  |  |  |  | 1530 |  |
| CAA | ACA | AAT | AAA | ACA | CTG | GTT | GAA | ATT | CCA | GAA | ATG | GTT | GCC | ACT | GAA | 4782 |
| Gln | Thr | Asn | Lys | Thr | Leu | Val | Glu | Ile | Pro | Glu | Met | Val | Ala | Thr | Glu |  |
|  |  |  |  | 1535 |  |  |  |  | 1540 |  |  |  |  | 1545 |  |  |
| GCT | GCC | TTT | CTA | TGC | TTC | ATG | TAC | AAT | TTG | CCA | GTG | ACA | ACA | CAG | AGT | 4830 |
| Ala | Ala | Phe | Leu | Cys | Phe | Met | Tyr | Asn | Leu | Pro | Val | Thr | Thr | Gln | Ser |  |
|  |  |  | 1550 |  |  |  |  | 1555 |  |  |  |  | 1560 |  |  |  |
| GTT | TCA | ACC | ACA | CTG | CTG | GAA | AAT | GCC | ACA | TTA | TTA | CAA | GCT | AGA | ACT | 4878 |
| Val | Ser | Thr | Thr | Leu | Leu | Glu | Asn | Ala | Thr | Leu | Leu | Gln | Ala | Arg | Thr |  |
|  |  |  | 1565 |  |  |  |  | 1570 |  |  |  |  | 1575 |  |  |  |
| ATG | GCA | CAG | TTT | GAG | CTA | TCA | TAT | TTT | TAC | ACA | ATT | AAT | TTT | GTG | CGA | 4926 |
| Met | Ala | Gln | Phe | Glu | Leu | Ser | Tyr | Phe | Tyr | Thr | Ile | Asn | Phe | Val | Arg |  |
|  |  |  | 1580 |  |  |  |  | 1585 |  |  |  |  | 1590 |  |  |  |
| TTT | GAT | GGT | AGT | ATG | CAT | CCA | GTC | ATA | CAT | GAC | AAG | CTG | AAG | CGC | TTT | 4974 |
| Phe | Asp | Gly | Ser | Met | His | Pro | Val | Ile | His | Asp | Lys | Leu | Lys | Arg | Phe |  |
| 1595 |  |  |  |  | 1600 |  |  |  |  | 1605 |  |  |  |  | 1610 |  |
| AAG | CTA | CAC | ACT | TGT | GAG | ACA | TTC | CTC | AAT | AAG | TTG | GCG | ATC | CCA | AAT | 5022 |
| Lys | Leu | His | Thr | Cys | Glu | Thr | Phe | Leu | Asn | Lys | Leu | Ala | Ile | Pro | Asn |  |
|  |  |  |  | 1615 |  |  |  |  | 1620 |  |  |  |  | 1625 |  |  |
| AAA | GGC | TTA | TCC | TCT | TGG | CTT | ACG | AGT | GGA | GAG | TAT | AAG | CGA | CTT | GGT | 5070 |
| Lys | Gly | Leu | Ser | Ser | Trp | Leu | Thr | Ser | Gly | Glu | Tyr | Lys | Arg | Leu | Gly |  |

|  |  |  |
|---|---|---|
| 1630 | 1635 | 1640 |

```
TAC  ATA  GCA  GAG  GAT  GCT  GGC  ATA  AGA  ATC  CCA  TTC  GTG  TGC  AAA  GAA      5118
Tyr  Ile  Ala  Glu  Asp  Ala  Gly  Ile  Arg  Ile  Pro  Phe  Val  Cys  Lys  Glu
          1645                     1650                     1655

ATT  CCA  GAC  TCC  TTG  CAT  GAG  GAA  ATT  TGG  CAC  ATT  GTA  GTC  GCC  CAT      5166
Ile  Pro  Asp  Ser  Leu  His  Glu  Glu  Ile  Trp  His  Ile  Val  Val  Ala  His
          1660                     1665                     1670

AAA  GGT  GAC  TCG  GGT  ATT  GGG  AGG  CTC  ACT  AGC  GTA  CAG  GCA  GCA  AAG      5214
Lys  Gly  Asp  Ser  Gly  Ile  Gly  Arg  Leu  Thr  Ser  Val  Gln  Ala  Ala  Lys
1675                1680                     1685                     1690

GTT  GTT  TAT  ACT  CTG  CAA  ACG  GAT  GTG  CAC  TCA  ATT  GCG  AGG  ACT  CTA      5262
Val  Val  Tyr  Thr  Leu  Gln  Thr  Asp  Val  His  Ser  Ile  Ala  Arg  Thr  Leu
                    1695                     1700                     1705

GCA  TGC  ATC  AAT  AGA  CGC  ATA  GCA  GAT  GAA  CAA  ATG  AAG  CAG  AGT  CAT      5310
Ala  Cys  Ile  Asn  Arg  Arg  Ile  Ala  Asp  Glu  Gln  Met  Lys  Gln  Ser  His
                    1710                     1715                     1720

TTT  GAA  GCC  GCA  ACT  GGG  AGA  GCA  TTT  TCC  TTC  ACA  AAT  TAC  TCA  ATA      5358
Phe  Glu  Ala  Ala  Thr  Gly  Arg  Ala  Phe  Ser  Phe  Thr  Asn  Tyr  Ser  Ile
               1725                     1730                     1735

CAA  AGC  ATA  TTT  GAC  ACG  CTG  AAA  GCA  AAT  TAT  GCT  ACA  AAG  CAT  ACG      5406
Gln  Ser  Ile  Phe  Asp  Thr  Leu  Lys  Ala  Asn  Tyr  Ala  Thr  Lys  His  Thr
          1740                     1745                     1750

AAA  GAA  AAT  ATT  GCA  GTG  CTT  CAG  CAG  GCA  AAA  GAT  CAA  TTG  CTA  GAG      5454
Lys  Glu  Asn  Ile  Ala  Val  Leu  Gln  Gln  Ala  Lys  Asp  Gln  Leu  Leu  Glu
1755                1760                     1765                     1770

TTT  TCG  AAC  CTA  GCA  AAG  GAT  CAA  GAT  GTC  ACG  GGT  ATC  ATC  CAA  GAC      5502
Phe  Ser  Asn  Leu  Ala  Lys  Asp  Gln  Asp  Val  Thr  Gly  Ile  Ile  Gln  Asp
                    1775                     1780                     1785

TTC  AAT  CAC  CTG  GAA  ACT  ATC  TAT  CTC  CAA  TCA  GAT  AGC  GAA  GTG  GCT      5550
Phe  Asn  His  Leu  Glu  Thr  Ile  Tyr  Leu  Gln  Ser  Asp  Ser  Glu  Val  Ala
                    1790                     1795                     1800

AAG  CAT  CTG  AAG  CTT  AAA  AGT  CAC  TGG  AAT  AAA  AGC  CAA  ATC  ACT  AGG      5598
Lys  His  Leu  Lys  Leu  Lys  Ser  His  Trp  Asn  Lys  Ser  Gln  Ile  Thr  Arg
          1805                     1810                     1815

GAC  ATC  ATA  ATA  GCT  TTG  TCT  GTG  TTA  ATT  GGT  GGT  GGA  TGG  ATG  CTT      5646
Asp  Ile  Ile  Ile  Ala  Leu  Ser  Val  Leu  Ile  Gly  Gly  Gly  Trp  Met  Leu
1820                1825                     1830

GCA  ACG  TAC  TTC  AAG  GAC  AAG  TTC  AAT  GAA  CCA  GTC  TAT  TTC  CAA  GGG      5694
Ala  Thr  Tyr  Phe  Lys  Asp  Lys  Phe  Asn  Glu  Pro  Val  Tyr  Phe  Gln  Gly
1835                1840                     1845                     1850

AAG  AAG  AAT  CAG  AAG  CAC  AAG  CTT  AAG  ATG  AGA  GAG  GCG  CGT  GGG  GCT      5742
Lys  Lys  Asn  Gln  Lys  His  Lys  Leu  Lys  Met  Arg  Glu  Ala  Arg  Gly  Ala
                    1855                     1860                     1865

AGA  GGG  CAA  TAT  GAG  GTT  GCA  GCG  GAG  CCA  GAG  GCG  CTA  GAA  CAT  TAC      5790
Arg  Gly  Gln  Tyr  Glu  Val  Ala  Ala  Glu  Pro  Glu  Ala  Leu  Glu  His  Tyr
               1870                     1875                     1880

TTT  GGA  AGC  GCA  TAT  AAT  AAC  AAA  GGA  AAG  CGC  AAG  GGC  ACC  ACG  AGA      5838
Phe  Gly  Ser  Ala  Tyr  Asn  Asn  Lys  Gly  Lys  Arg  Lys  Gly  Thr  Thr  Arg
          1885                     1890                     1895

GGA  ATG  GGT  GCA  AAG  TCT  CGG  AAA  TTC  ATA  AAC  ATG  TAT  GGG  TTT  GAT      5886
Gly  Met  Gly  Ala  Lys  Ser  Arg  Lys  Phe  Ile  Asn  Met  Tyr  Gly  Phe  Asp
1900                     1905                     1910

CCA  ACT  GAT  TTT  TCA  TAC  ATT  AGG  TTT  GTG  GAT  CCA  TTG  ACA  GGT  CAC      5934
Pro  Thr  Asp  Phe  Ser  Tyr  Ile  Arg  Phe  Val  Asp  Pro  Leu  Thr  Gly  His
1915                     1920                     1925                     1930

ACT  ATT  GAT  GAG  TCC  ACA  AAC  GCA  CCT  ATT  GAT  TTA  GTG  CAG  CAT  GAG      5982
Thr  Ile  Asp  Glu  Ser  Thr  Asn  Ala  Pro  Ile  Asp  Leu  Val  Gln  His  Glu
                    1935                     1940                     1945

TTT  GGA  AAG  GTT  AGA  ACA  CGC  ATG  TTA  ATT  GAC  GAT  GAG  ATA  GAG  CCT      6030
Phe  Gly  Lys  Val  Arg  Thr  Arg  Met  Leu  Ile  Asp  Asp  Glu  Ile  Glu  Pro
```

|  |  |  |  |  |  |  |  |  |  |  |  |  |  |  |  |
|---|---|---|---|---|---|---|---|---|---|---|---|---|---|---|---|
| | | | | 1950 | | | | | 1955 | | | | | 1960 | |
| CAA | AGT | CTT | AGC | ACC | CAC | ACC | ACA | ATC | CAT | GCT | TAT | TTG | GTG | AAT | AGT | 6078
| Gln | Ser | Leu | Ser | Thr | His | Thr | Thr | Ile | His | Ala | Tyr | Leu | Val | Asn | Ser |
| | | 1965 | | | | 1970 | | | | | 1975 | | | | |
| GGC | ACG | AAG | AAA | GTT | CTT | AAG | GTT | GAT | TTA | ACA | CCA | CAC | TCG | TCG | CTA | 6126
| Gly | Thr | Lys | Lys | Val | Leu | Lys | Val | Asp | Leu | Thr | Pro | His | Ser | Ser | Leu |
| | 1980 | | | | 1985 | | | | | 1990 | | | | | |
| CGT | GCG | AGT | GAG | AAA | TCA | ACA | GCA | ATA | ATG | GGA | TTT | CCT | GAA | AGG | GAG | 6174
| Arg | Ala | Ser | Glu | Lys | Ser | Thr | Ala | Ile | Met | Gly | Phe | Pro | Glu | Arg | Glu |
| 1995 | | | | | 2000 | | | | | 2005 | | | | | 2010 |
| AAT | GAA | TTG | CGT | CAA | ACC | GGC | ATG | GCA | GTG | CCA | GTG | GCT | TAT | GAT | CAA | 6222
| Asn | Glu | Leu | Arg | Gln | Thr | Gly | Met | Ala | Val | Pro | Val | Ala | Tyr | Asp | Gln |
| | | | 2015 | | | | | 2020 | | | | | 2025 | | |
| TTG | CCA | CCA | AAG | AAT | GAG | GAC | TTG | ACG | TTT | GAA | GGA | GAA | AGC | TTG | TTT | 6270
| Leu | Pro | Pro | Lys | Asn | Glu | Asp | Leu | Thr | Phe | Glu | Gly | Glu | Ser | Leu | Phe |
| | | 2030 | | | | | 2035 | | | | | 2040 | | | |
| AAG | GGA | CCA | CGT | GAT | TAC | AAC | CCG | ATA | TCG | AGC | ACC | ATT | TGT | CAT | TTG | 6318
| Lys | Gly | Pro | Arg | Asp | Tyr | Asn | Pro | Ile | Ser | Ser | Thr | Ile | Cys | His | Leu |
| | | 2045 | | | | | 2050 | | | | | 2055 | | | |
| ACG | AAT | GAA | TCT | GAT | GGG | CAC | ACA | ACA | TCG | TTG | TAT | GGT | ATT | GGA | TTT | 6366
| Thr | Asn | Glu | Ser | Asp | Gly | His | Thr | Thr | Ser | Leu | Tyr | Gly | Ile | Gly | Phe |
| 2060 | | | | | 2065 | | | | | 2070 | | | | | |
| GGT | CCC | TTC | ATC | ATT | ACA | AAC | AAG | CAC | TTG | TTT | AGA | AGA | AAT | AAT | GGA | 6414
| Gly | Pro | Phe | Ile | Ile | Thr | Asn | Lys | His | Leu | Phe | Arg | Arg | Asn | Asn | Gly |
| 2075 | | | | | 2080 | | | | | 2085 | | | | | 2090 |
| ACA | CTG | TTG | GTC | CAA | TCA | CTA | CAT | GGT | GTA | TTC | AAG | GTC | AAG | AAC | ACC | 6462
| Thr | Leu | Leu | Val | Gln | Ser | Leu | His | Gly | Val | Phe | Lys | Val | Lys | Asn | Thr |
| | | | | 2095 | | | | | 2100 | | | | | 2105 | |
| ACG | ACT | TTG | CAA | CAA | CAC | CTC | ATT | GAT | GGG | AGG | GAC | ATG | ATA | ATT | ATT | 6510
| Thr | Thr | Leu | Gln | Gln | His | Leu | Ile | Asp | Gly | Arg | Asp | Met | Ile | Ile | Ile |
| | | | 2110 | | | | | 2115 | | | | | 2120 | | |
| CGC | ATG | CCT | AAG | GAT | TTC | CCA | CCA | TTT | CCT | CAA | AAG | CTG | AAA | TTT | AGA | 6558
| Arg | Met | Pro | Lys | Asp | Phe | Pro | Pro | Phe | Pro | Gln | Lys | Leu | Lys | Phe | Arg |
| | | 2125 | | | | | 2130 | | | | | 2135 | | | |
| GAG | CCA | CAA | AGG | GAA | GAG | CGC | ATA | TGT | CTT | GTG | ACA | ACC | AAC | TTC | CAA | 6606
| Glu | Pro | Gln | Arg | Glu | Glu | Arg | Ile | Cys | Leu | Val | Thr | Thr | Asn | Phe | Gln |
| | 2140 | | | | | 2145 | | | | | 2150 | | | | |
| ACT | AAG | AGC | ATG | TCT | AGC | ATG | GTG | TCA | GAC | ACT | AGT | TGC | ACA | TTC | CCT | 6654
| Thr | Lys | Ser | Met | Ser | Ser | Met | Val | Ser | Asp | Thr | Ser | Cys | Thr | Phe | Pro |
| 2155 | | | | | 2160 | | | | | 2165 | | | | | 2170 |
| TCA | TCT | GAT | GGC | ATA | TTC | TGG | AAG | CAT | TGG | ATT | CAA | ACC | AAG | GAT | GGG | 6702
| Ser | Ser | Asp | Gly | Ile | Phe | Trp | Lys | His | Trp | Ile | Gln | Thr | Lys | Asp | Gly |
| | | | | 2175 | | | | | 2180 | | | | | 2185 | |
| CAG | TGT | GGC | AGT | CCA | TTA | GTA | TCA | ACT | AGA | GAT | GGG | TTC | ATT | GTT | GGT | 6750
| Gln | Cys | Gly | Ser | Pro | Leu | Val | Ser | Thr | Arg | Asp | Gly | Phe | Ile | Val | Gly |
| | | | 2190 | | | | | 2195 | | | | | 2200 | | |
| ATA | CAC | TCA | GCA | TCG | AAT | TTC | ACC | AAC | ACA | AAC | AAT | TAT | TTC | ACA | AGC | 6798
| Ile | His | Ser | Ala | Ser | Asn | Phe | Thr | Asn | Thr | Asn | Asn | Tyr | Phe | Thr | Ser |
| | | 2205 | | | | | 2210 | | | | | 2215 | | | |
| GTG | CCG | AAA | AAC | TTC | ATG | GAA | TTG | TTG | ACA | AAT | CAG | GAG | GCG | CAG | CAG | 6846
| Val | Pro | Lys | Asn | Phe | Met | Glu | Leu | Leu | Thr | Asn | Gln | Glu | Ala | Gln | Gln |
| | 2220 | | | | | 2225 | | | | | 2230 | | | | |
| TGG | GTT | AGT | GGT | TGG | CGA | TTA | AAT | GCT | GAC | TCA | GTA | TTG | TGG | GGG | GGC | 6894
| Trp | Val | Ser | Gly | Trp | Arg | Leu | Asn | Ala | Asp | Ser | Val | Leu | Trp | Gly | Gly |
| 2235 | | | | | 2240 | | | | | 2245 | | | | | 2250 |
| CAT | AAA | GTT | TTC | ATG | AGC | AAA | CCT | GAA | GAG | CCT | TTT | CAG | CCA | GTT | AAG | 6942
| His | Lys | Val | Phe | Met | Ser | Lys | Pro | Glu | Glu | Pro | Phe | Gln | Pro | Val | Lys |
| | | | | 2255 | | | | | 2260 | | | | | 2265 | |
| GAA | GCG | ACT | CAA | CTC | ATG | AAT | GAA | TTG | GTG | TAC | TCG | CAA | GGG | GAG | AAG | 6990
| Glu | Ala | Thr | Gln | Leu | Met | Asn | Glu | Leu | Val | Tyr | Ser | Gln | Gly | Glu | Lys |

|  |  |
|---|---|
| 2270 2275 2280 | |
| AGG AAA TGG GTC GTG GAA GCA CTG TCA GGG AAC TTG AGG CCA GTG GCT<br>Arg Lys Trp Val Val Glu Ala Leu Ser Gly Asn Leu Arg Pro Val Ala<br>     2285               2290              2295 | 7038 |
| GAG TGT CCC AGT CAG TTA GTC ACA AAG CAT GTG GTT AAA GGA AAG TGT<br>Glu Cys Pro Ser Gln Leu Val Thr Lys His Val Val Lys Gly Lys Cys<br>2300              2305              2310 | 7086 |
| CCC CTC TTT GAG CTC TAC TTG CAG TTG AAT CCA GAA AAG GAA GCA TAT<br>Pro Leu Phe Glu Leu Tyr Leu Gln Leu Asn Pro Glu Lys Glu Ala Tyr<br>2315              2320              2325              2330 | 7134 |
| TTT AAA CCG ATG ATG GGA GCA TAT AAG CCA AGT CGA CTT AAT AGA GAG<br>Phe Lys Pro Met Met Gly Ala Tyr Lys Pro Ser Arg Leu Asn Arg Glu<br>               2335              2340              2345 | 7182 |
| GCG TTC CTC AAG GAC ATT CTA AAA TAT GCT AGT GAA ATT GAG ATT GGG<br>Ala Phe Leu Lys Asp Ile Leu Lys Tyr Ala Ser Glu Ile Glu Ile Gly<br>               2350              2355              2360 | 7230 |
| AAT GTG GAT TGT GAC TTG CTG GAG CTT GCA ATA AGC ATG CTC GTC ACA<br>Asn Val Asp Cys Asp Leu Leu Glu Leu Ala Ile Ser Met Leu Val Thr<br>               2365              2370              2375 | 7278 |
| AAG CTC AAG GCG TTA GGA TTC CCA ACT GTG AAC TAC ATC ACT GAC CCA<br>Lys Leu Lys Ala Leu Gly Phe Pro Thr Val Asn Tyr Ile Thr Asp Pro<br>     2380              2385              2390 | 7326 |
| GAG GAA ATT TTT AGT GCA TTG AAT ATG AAA GCA GCT ATG GGA GCA CTA<br>Glu Glu Ile Phe Ser Ala Leu Asn Met Lys Ala Ala Met Gly Ala Leu<br>2395              2400              2405              2410 | 7374 |
| TAC AAA GGC AAG AAG AAA GAA GCT CTC AGC GAG CTC ACA CTA GAT GAG<br>Tyr Lys Gly Lys Lys Lys Glu Ala Leu Ser Glu Leu Thr Leu Asp Glu<br>               2415              2420              2425 | 7422 |
| CAG GAG GCA ATG CTC AAA GCA AGT TGC CTG CGA CTG TAT ACG GGA AAG<br>Gln Glu Ala Met Leu Lys Ala Ser Cys Leu Arg Leu Tyr Thr Gly Lys<br>               2430              2435              2440 | 7470 |
| TTG GGA ATT TGG AAT GGC TCA TTG AAA GCA GAG TTG CGT CCA ATT GAG<br>Leu Gly Ile Trp Asn Gly Ser Leu Lys Ala Glu Leu Arg Pro Ile Glu<br>               2445              2450              2455 | 7518 |
| AAG GTT GAA AAC AAC AAA ACG CGA ACT TTC ACA GCA GCA CCA ATA GAC<br>Lys Val Glu Asn Asn Lys Thr Arg Thr Phe Thr Ala Ala Pro Ile Asp<br>     2460              2465              2470 | 7566 |
| ACT CTT CTT GCT GGT AAA GTT TGC GTG GAT GAT TTC AAC AAT CAA TTT<br>Thr Leu Leu Ala Gly Lys Val Cys Val Asp Asp Phe Asn Asn Gln Phe<br>2475              2480              2485              2490 | 7614 |
| TAT GAT CTC AAC ATA AAG GCA CCA TGG ACA GTT GGT ATG ACT AAG TTT<br>Tyr Asp Leu Asn Ile Lys Ala Pro Trp Thr Val Gly Met Thr Lys Phe<br>               2495              2500              2505 | 7662 |
| TAT CAG GGG TGG AAT GAA TTG ATG GAG GCT TTA CCA AGT GGG TGG GTG<br>Tyr Gln Gly Trp Asn Glu Leu Met Glu Ala Leu Pro Ser Gly Trp Val<br>               2510              2515              2520 | 7710 |
| TAT TGT GAC GCT GAT GGT TCG CAA TTC GAC AGT TCC TTG ACT CCA TTC<br>Tyr Cys Asp Ala Asp Gly Ser Gln Phe Asp Ser Ser Leu Thr Pro Phe<br>     2525              2530              2535 | 7758 |
| CTC ATT AAT GCT GTA TTG AAA GTG CGA CTT GCC TTC ATG GAG GAA TGG<br>Leu Ile Asn Ala Val Leu Lys Val Arg Leu Ala Phe Met Glu Glu Trp<br>     2540              2545              2550 | 7806 |
| GAT ATT GGT GAG CAA ATG CTG CGA AAT TTG TAC ACT GAG ATA GTG TAT<br>Asp Ile Gly Glu Gln Met Leu Arg Asn Leu Tyr Thr Glu Ile Val Tyr<br>2555              2560              2565              2570 | 7854 |
| ACA CCA ATC CTC ACA CCG GAT GGT ACT ATC ATT AAG AAG CAT AAA GGC<br>Thr Pro Ile Leu Thr Pro Asp Gly Thr Ile Ile Lys Lys His Lys Gly<br>               2575              2580              2585 | 7902 |
| AAC AAT AGC GGG CAA CCT TCA ACA GTG GTG GAC AAC ACA CTC ATG GTC<br>Asn Asn Ser Gly Gln Pro Ser Thr Val Val Asp Asn Thr Leu Met Val | 7950 |

-continued

|  |  |  |  |  |  |  |  |  |  |  |  |  |  |  |  |  |
|---|---|---|---|---|---|---|---|---|---|---|---|---|---|---|---|---|
|  |  |  |  |  | 2590 |  |  |  |  | 2595 |  |  |  |  | 2600 |  |
| ATT | ATT | GCA | ATG | TTA | TAC | ACA | TGT | GAG | AAG | TGT | GGA | ATC | AAC | AAG | GAA | 7998 |
| Ile | Ile | Ala | Met | Leu | Tyr | Thr | Cys | Glu | Lys | Cys | Gly | Ile | Asn | Lys | Glu |  |
|  |  |  |  | 2605 |  |  |  | 2610 |  |  |  | 2615 |  |  |  |  |
| GAG | ATT | GTG | TAT | TAC | GTC | AAT | GGC | GAT | GAC | CTA | TTG | ATT | GCC | ATT | CAC | 8046 |
| Glu | Ile | Val | Tyr | Tyr | Val | Asn | Gly | Asp | Asp | Leu | Leu | Ile | Ala | Ile | His |  |
|  | 2620 |  |  |  |  | 2625 |  |  |  |  | 2630 |  |  |  |  |  |
| CCA | GAT | AAA | GCT | GAG | AGG | TTG | AGT | AGA | TTC | AAA | GAA | TCT | TTC | GGA | GAG | 8094 |
| Pro | Asp | Lys | Ala | Glu | Arg | Leu | Ser | Arg | Phe | Lys | Glu | Ser | Phe | Gly | Glu |  |
| 2635 |  |  |  |  | 2640 |  |  |  |  | 2645 |  |  |  |  | 2650 |  |
| TTG | GGC | CTG | AAA | TAT | GAA | TTT | GAC | TGT | ACC | ACC | AGG | GAC | AAG | ACA | CAG | 8142 |
| Leu | Gly | Leu | Lys | Tyr | Glu | Phe | Asp | Cys | Thr | Thr | Arg | Asp | Lys | Thr | Gln |  |
|  |  |  |  | 2655 |  |  |  | 2660 |  |  |  | 2665 |  |  |  |  |
| TTG | TGG | TTC | ATG | TCA | CAC | AGG | GCT | TTG | GAG | AGG | GAT | GGC | ATG | TAT | ATA | 8190 |
| Leu | Trp | Phe | Met | Ser | His | Arg | Ala | Leu | Glu | Arg | Asp | Gly | Met | Tyr | Ile |  |
|  |  |  | 2670 |  |  |  |  | 2675 |  |  |  |  | 2680 |  |  |  |
| CCA | AAG | CTA | GAA | GAA | GAA | AGG | ATT | GTT | TCT | ATT | TTG | GAA | TGG | GAC | AGA | 8238 |
| Pro | Lys | Leu | Glu | Glu | Glu | Arg | Ile | Val | Ser | Ile | Leu | Glu | Trp | Asp | Arg |  |
|  |  | 2685 |  |  |  |  | 2690 |  |  |  |  | 2695 |  |  |  |  |
| TCC | AAA | GAG | CCG | TCA | CAT | AGG | CTT | GAA | GCC | ATC | TGT | GCA | TCA | ATG | ATT | 8286 |
| Ser | Lys | Glu | Pro | Ser | His | Arg | Leu | Glu | Ala | Ile | Cys | Ala | Ser | Met | Ile |  |
| 2700 |  |  |  |  | 2705 |  |  |  |  | 2710 |  |  |  |  |  |  |
| GAA | GCA | TGG | GGT | TAT | GAC | AAG | CTG | GTT | GAA | GAA | ATC | CGC | AAT | TTC | TAT | 8334 |
| Glu | Ala | Trp | Gly | Tyr | Asp | Lys | Leu | Val | Glu | Glu | Ile | Arg | Asn | Phe | Tyr |  |
| 2715 |  |  |  |  | 2720 |  |  |  |  | 2725 |  |  |  |  | 2730 |  |
| GCA | TGG | GTT | TTG | GAA | CAA | GCG | CCG | TAT | TCA | CAG | CTT | GCA | GAA | GAA | GGA | 8382 |
| Ala | Trp | Val | Leu | Glu | Gln | Ala | Pro | Tyr | Ser | Gln | Leu | Ala | Glu | Glu | Gly |  |
|  |  |  |  | 2735 |  |  |  | 2740 |  |  |  | 2745 |  |  |  |  |
| AAG | GCG | CCA | TAT | CTG | GCT | GAG | ACT | GCG | CTT | AAG | TTT | TTG | TAC | ACA | TCT | 8430 |
| Lys | Ala | Pro | Tyr | Leu | Ala | Glu | Thr | Ala | Leu | Lys | Phe | Leu | Tyr | Thr | Ser |  |
|  |  |  | 2750 |  |  |  |  | 2755 |  |  |  |  | 2760 |  |  |  |
| CAG | CAC | GGA | ACA | AAC | TCT | GAG | ATA | GAA | GAG | TAT | TTA | AAA | GTG | TTG | TAT | 8478 |
| Gln | His | Gly | Thr | Asn | Ser | Glu | Ile | Glu | Glu | Tyr | Leu | Lys | Val | Leu | Tyr |  |
|  |  | 2765 |  |  |  |  | 2770 |  |  |  |  | 2775 |  |  |  |  |
| GAT | TAC | GAT | ATT | CCA | ACG | ACT | GAG | AAT | CTT | TAT | TTT | CAG | AGT | GGC | ACT | 8526 |
| Asp | Tyr | Asp | Ile | Pro | Thr | Thr | Glu | Asn | Leu | Tyr | Phe | Gln | Ser | Gly | Thr |  |
|  |  | 2780 |  |  |  |  | 2785 |  |  |  |  | 2790 |  |  |  |  |
| GTG | GAT | GCT | GGT | GCT | GAC | GCT | GGT | AAG | AAG | AAA | GAT | CAA | AAG | GAT | GAT | 8574 |
| Val | Asp | Ala | Gly | Ala | Asp | Ala | Gly | Lys | Lys | Lys | Asp | Gln | Lys | Asp | Asp |  |
| 2795 |  |  |  |  | 2800 |  |  |  |  | 2805 |  |  |  |  | 2810 |  |
| AAA | GTC | GCT | GAG | CAG | GCT | TCA | AAG | GAT | AGG | GAT | GTT | AAT | GCT | GGA | ACT | 8622 |
| Lys | Val | Ala | Glu | Gln | Ala | Ser | Lys | Asp | Arg | Asp | Val | Asn | Ala | Gly | Thr |  |
|  |  |  |  | 2815 |  |  |  | 2820 |  |  |  | 2825 |  |  |  |  |
| TCA | GGA | ACA | TTC | TCA | GTT | CCA | CGA | ATA | AAT | GCT | ATG | GCC | ACA | AAA | CTT | 8670 |
| Ser | Gly | Thr | Phe | Ser | Val | Pro | Arg | Ile | Asn | Ala | Met | Ala | Thr | Lys | Leu |  |
|  |  |  | 2830 |  |  |  |  | 2835 |  |  |  |  | 2840 |  |  |  |
| CAA | TAT | CCA | AGG | ATG | AGG | GGA | GAG | GTG | GTT | GTA | AAC | TTG | AAT | CAC | CTT | 8718 |
| Gln | Tyr | Pro | Arg | Met | Arg | Gly | Glu | Val | Val | Val | Asn | Leu | Asn | His | Leu |  |
|  |  | 2845 |  |  |  |  | 2850 |  |  |  |  | 2855 |  |  |  |  |
| TTA | GGA | TAC | AAG | CCA | CAG | CAA | ATT | GAT | TTG | TCA | AAT | GCT | CGA | GCC | ACA | 8766 |
| Leu | Gly | Tyr | Lys | Pro | Gln | Gln | Ile | Asp | Leu | Ser | Asn | Ala | Arg | Ala | Thr |  |
|  | 2860 |  |  |  |  | 2865 |  |  |  |  | 2870 |  |  |  |  |  |
| CAT | GAG | CAG | TTT | GCC | GCG | TGG | CAT | CAG | GCA | GTG | ATG | ACA | GCC | TAT | GGA | 8814 |
| His | Glu | Gln | Phe | Ala | Ala | Trp | His | Gln | Ala | Val | Met | Thr | Ala | Tyr | Gly |  |
| 2875 |  |  |  |  | 2880 |  |  |  |  | 2885 |  |  |  |  | 2890 |  |
| GTG | AAT | GAA | GAG | CAA | ATG | AAA | ATA | TTG | CTA | AAT | GGA | TTT | ATG | GTG | TGG | 8862 |
| Val | Asn | Glu | Glu | Gln | Met | Lys | Ile | Leu | Leu | Asn | Gly | Phe | Met | Val | Trp |  |
|  |  |  |  | 2895 |  |  |  | 2900 |  |  |  | 2905 |  |  |  |  |
| TGC | ATA | GAA | AAT | GGG | ACT | TCC | CCA | AAT | TTG | AAC | GGA | ACT | TGG | GTT | ATG | 8910 |
| Cys | Ile | Glu | Asn | Gly | Thr | Ser | Pro | Asn | Leu | Asn | Gly | Thr | Trp | Val | Met |  |

|  |  |  |  |  |  |  |  |  |  |  |  |  |  |  |  |
|---|---|---|---|---|---|---|---|---|---|---|---|---|---|---|---|
|  |  |  |  | 2910 |  |  |  |  | 2915 |  |  |  |  | 2920 |  |
| ATG | GAT | GGT | GAG | GAT | CAA | GTT | TCA | TAC | CCG | CTG | AAA | CCA | ATG | GTT | GAA | 8958 |
| Met | Asp | Gly | Glu | Asp | Gln | Val | Ser | Tyr | Pro | Leu | Lys | Pro | Met | Val | Glu |  |
|  |  | 2925 |  |  |  |  | 2930 |  |  |  |  | 2935 |  |  |  |
| AAC | GCG | CAG | CCA | ACA | CTG | AGG | CAA | ATT | ATG | ACA | CAC | TTC | AGT | GAC | CTG | 9006 |
| Asn | Ala | Gln | Pro | Thr | Leu | Arg | Gln | Ile | Met | Thr | His | Phe | Ser | Asp | Leu |  |
|  | 2940 |  |  |  |  | 2945 |  |  |  |  | 2950 |  |  |  |  |  |
| GCT | GAA | GCG | TAT | ATT | GAG | ATG | AGG | AAT | AGG | GAG | CGA | CCA | TAC | ATG | CCT | 9054 |
| Ala | Glu | Ala | Tyr | Ile | Glu | Met | Arg | Asn | Arg | Glu | Arg | Pro | Tyr | Met | Pro |  |
| 2955 |  |  |  |  | 2960 |  |  |  |  | 2965 |  |  |  |  | 2970 |  |
| AGG | TAT | GGT | CTA | CAG | AGA | AAC | ATT | ACA | GAC | ATG | AGT | TTG | TCA | CGC | TAT | 9102 |
| Arg | Tyr | Gly | Leu | Gln | Arg | Asn | Ile | Thr | Asp | Met | Ser | Leu | Ser | Arg | Tyr |  |
|  |  |  |  | 2975 |  |  |  |  | 2980 |  |  |  |  | 2985 |  |  |
| GCG | TTC | GAC | TTC | TAT | GAG | CTA | ACT | TCA | AAA | ACA | CCT | GTT | AGA | GCG | AGG | 9150 |
| Ala | Phe | Asp | Phe | Tyr | Glu | Leu | Thr | Ser | Lys | Thr | Pro | Val | Arg | Ala | Arg |  |
|  |  |  | 2990 |  |  |  |  | 2995 |  |  |  |  | 3000 |  |  |  |
| GAG | GCG | CAT | ATG | CAA | ATG | AAA | GCT | GCT | GCA | GTA | CGA | AAC | AGT | GGA | ACT | 9198 |
| Glu | Ala | His | Met | Gln | Met | Lys | Ala | Ala | Ala | Val | Arg | Asn | Ser | Gly | Thr |  |
|  |  |  | 3005 |  |  |  |  | 3010 |  |  |  |  | 3015 |  |  |  |
| AGG | TTA | TTT | GGT | CTT | GAT | GGC | AAC | GTG | GGT | ACT | GCA | GAG | GAA | GAC | ACT | 9246 |
| Arg | Leu | Phe | Gly | Leu | Asp | Gly | Asn | Val | Gly | Thr | Ala | Glu | Glu | Asp | Thr |  |
|  | 3020 |  |  |  |  | 3025 |  |  |  |  | 3030 |  |  |  |  |  |
| GAA | CGG | CAC | ACA | GCG | CAC | GAT | GTG | AAC | CGT | AAC | ATG | CAC | ACA | CTA | TTA | 9294 |
| Glu | Arg | His | Thr | Ala | His | Asp | Val | Asn | Arg | Asn | Met | His | Thr | Leu | Leu |  |
| 3035 |  |  |  |  | 3040 |  |  |  |  | 3045 |  |  |  |  | 3050 |  |
| GGG | GTC | CGC | CAG | TGA | TAGTTTCTGC | | GTGTCTTTGC | | TTTCCGCTTT | | TAAGCTTATT | | | | | 9349 |
| Gly | Val | Arg | Gln |  |  |  |  |  |  |  |  |  |  |  |  |  |

GTAATATATA TGAATAGCTA TTCACAGTGG GACTTGGTCT TGTGTTGAAT AGTATCTTAT 9409

ATATTTTAAT ATGTCTTATT AGTCTCATTA CTTAGGCGAA CGACAAAGTG AGGTCACCTC 9469

GGTCTAATTC TCCTATGTAG TGCGAG 9495

( 2 ) INFORMATION FOR SEQ ID NO: 2:

( i ) SEQUENCE CHARACTERISTICS:
        ( A ) LENGTH: 792
        ( B ) TYPE: Nucleic Acid
        ( C ) STRANDEDNESS: Double
        ( D ) TOPOLOGY: Circular ( i i ) MOLECULE TYPE: cDNA to genomic RNA ( i i i ) HYPOTHETICAL: No ( i v ) ANTI-SENSE: No ( v ) FRAGMENT TYPE: N/A ( v i ) ORIGINAL SOURCE:
        ( A ) ORGANISM: Tobacco Etch Virus
        ( B ) STRAIN: Highly Aphid Transmitted
        ( C ) INDIVIDUAL ISOLATE: N/A ( v i i ) IMMEDIATE SOURCE:
        ( A ) LIBRARY: No
        ( B ) CLONE: pTC:FL ( v i i i ) POSITION IN GENOME: N/A ( i x ) FEATURE:
        ( A ) NAME/KEY: Mutations (AGT→ATG) introduced into
            nucleotides corresponding to genomic nucleotides
            8518-8520 of SEQ ID No. 1, to create initiating
            methionine codon.
        ( B ) LOCATION: Nucleotides 1-3 of SEQ ID No. 2
        ( C ) IDENTIFICATION METHOD: --
        ( D ) OTHER INFORMATION: SEQ ID NO: 2 is the
            modified Tobacco Etch Virus coat protein gene present in pTC:FL.

(x) PUBLICATION INFORMATION:
    (A) AUTHORS: Allison et al.
    (B) TITLE: The nucleotide sequence of the
         coding region of Tobacco Etch Virus
         Genomic RNA: Evidence for the Synthesis
         of a Single Polyprotein
    (C) JOURNAL: Virology
    (D) VOLUME: 154
    (E) ISSUE: --
    (F) PAGES: 9-20
    (A) AUTHORS: Lindbo and Dougherty
    (B) TITLE: Untranslatable Transcripts of the
         tobacco etch virus coat protein gene
         sequence can interfere with tobacco etch
         virus replication in Transgenic Plants and
         Protoplasts
    (C) JOURNAL: Virology
    (D) VOLUME: 189
    (E) ISSUE: --
    (F) PAGES: 725-733

(xi) SEQUENCE DESCRIPTION: SEQ ID NO: 2:

```
                                                                ATG GGC ACT        9
                                                                Met Gly Thr
                                                                 1

GTG GAT GCT GGT GCT GAC GCT GGT AAG AAG AAA GAT CAA AAG GAT GAT   57
Val Asp Ala Gly Ala Asp Ala Gly Lys Lys Lys Asp Gln Lys Asp Asp
          5              10                  15

AAA GTC GCT GAG CAG GCT TCA AAG GAT AGG GAT GTT AAT GCT GGA ACT  105
Lys Val Ala Glu Gln Ala Ser Lys Asp Arg Asp Val Asn Ala Gly Thr
 20              25                  30                      35

TCA GGA ACA TTC TCA GTT CCA CGA ATA AAT GCT ATG GCC ACA AAA CTT  153
Ser Gly Thr Phe Ser Val Pro Arg Ile Asn Ala Met Ala Thr Lys Leu
                 40                  45                  50

CAA TAT CCA AGG ATG AGG GGA GAG GTG GTT GTA AAC TTG AAT CAC CTT  201
Gln Tyr Pro Arg Met Arg Gly Glu Val Val Val Asn Leu Asn His Leu
             55                  60                  65

TTA GGA TAC AAG CCA CAG CAA ATT GAT TTG TCA AAT GCT CGA GCC ACA  249
Leu Gly Tyr Lys Pro Gln Gln Ile Asp Leu Ser Asn Ala Arg Ala Thr
         70                  75                  80

CAT GAG CAG TTT GCC GCG TGG CAT CAG GCA GTG ATG ACA GCC TAT GGA  297
His Glu Gln Phe Ala Ala Trp His Gln Ala Val Met Thr Ala Tyr Gly
     85                  90                  95

GTG AAT GAA GAG CAA ATG AAA ATA TTG CTA AAT GGA TTT ATG GTG TGG  345
Val Asn Glu Glu Gln Met Lys Ile Leu Leu Asn Gly Phe Met Val Trp
100             105                 110                 115

TGC ATA GAA AAT GGG ACT TCC CCA AAT TTG AAC GGA ACT TGG GTT ATG  393
Cys Ile Glu Asn Gly Thr Ser Pro Asn Leu Asn Gly Thr Trp Val Met
                120                 125                 130

ATG GAT GGT GAG GAT CAA GTT TCA TAC CCG CTG AAA CCA ATG GTT GAA  441
Met Asp Gly Glu Asp Gln Val Ser Tyr Pro Leu Lys Pro Met Val Glu
            135                 140                 145

AAC GCG CAG CCA ACA CTG AGG CAA ATT ATG ACA CAC TTC AGT GAC CTG  489
Asn Ala Gln Pro Thr Leu Arg Gln Ile Met Thr His Phe Ser Asp Leu
        150                 155                 160

GCT GAA GCG TAT ATT GAG ATG AGG AAT AGG GAG CGA CCA TAC ATG CCT  537
Ala Glu Ala Tyr Ile Glu Met Arg Asn Arg Glu Arg Pro Tyr Met Pro
    165                 170                 175

AGG TAT GGT CTA CAG AGA AAC ATT ACA GAC ATG AGT TTG TCA CGC TAT  585
Arg Tyr Gly Leu Gln Arg Asn Ile Thr Asp Met Ser Leu Ser Arg Tyr
180                 185                 190                 195

GCG TTC GAC TTC TAT GAG CTA ACT TCA AAA ACA CCT GTT AGA GCG AGG  633
Ala Phe Asp Phe Tyr Glu Leu Thr Ser Lys Thr Pro Val Arg Ala Arg
                200                 205                 210
```

| | | | | | | | | | | | | | | | |
|---|---|---|---|---|---|---|---|---|---|---|---|---|---|---|---|
| GAG | GCG | CAT | ATG | CAA | ATG | AAA | GCT | GCT | GCA | GTA | CGA | AAC | AGT | GGA | ACT |
| Glu | Ala | His | Met | Gln | Met | Lys | Ala | Ala | Ala | Val | Arg | Asn | Ser | Gly | Thr |
| | | | 215 | | | | | 220 | | | | | 225 | | |

681

| | | | | | | | | | | | | | | | |
|---|---|---|---|---|---|---|---|---|---|---|---|---|---|---|---|
| AGG | TTA | TTT | GGT | CTT | GAT | GGC | AAC | GTG | GGT | ACT | GCA | GAG | GAA | GAC | ACT |
| Arg | Leu | Phe | Gly | Leu | Asp | Gly | Asn | Val | Gly | Thr | Ala | Glu | Glu | Asp | Thr |
| | | 230 | | | | | 235 | | | | | 240 | | | |

729

| | | | | | | | | | | | | | | | |
|---|---|---|---|---|---|---|---|---|---|---|---|---|---|---|---|
| GAA | CGG | CAC | ACA | GCG | CAC | GAT | GTG | AAC | CGT | AAC | ATG | CAC | ACA | CTA | TTA |
| Glu | Arg | His | Thr | Ala | His | Asp | Val | Asn | Arg | Asn | Met | His | Thr | Leu | Leu |
| | 245 | | | | | 250 | | | | | 255 | | | | |

777

| | | | |
|---|---|---|---|
| GGG | GTC | CGC | CAG | TGA |
| Gly | Val | Arg | Gln |
| 260 | | | |

792

( 2 ) INFORMATION FOR SEQ ID NO: 3:

( i ) SEQUENCE CHARACTERISTICS:
        ( A ) LENGTH: 793
        ( B ) TYPE: Nucleic Acid
        ( C ) STRANDEDNESS: Double
        ( D ) TOPOLOGY: Circular ( i i ) MOLECULE TYPE: cDNA to genomic RNA ( i i i ) HYPOTHETICAL: No ( i v ) ANTI-SENSE: No ( v ) FRAGMENT TYPE: N/A ( v i ) ORIGINAL SOURCE:
        ( A ) ORGANISM: Tobacco Etch Virus
        ( B ) STRAIN: Highly Aphid Transmitted
        ( C ) INDIVIDUAL ISOLATE: N/A ( v i i ) IMMEDIATE SOURCE:
        ( A ) LIBRARY: No
        ( B ) CLONE: pTC:RC ( v i i i ) POSITION IN GENOME: N/A ( i x ) FEATURE:
        ( A ) NAME/KEY: Mutation of AGT—GGC (Ser—
            Gly) to ATG—GCC (Met—Ser)
        ( B ) LOCATION: Nucleotides 1-6 of SEQ ID
            NO. 3 (corresponding to nucleotides
            8518-8523 of SEQ ID NO. 1)
        ( A ) NAME/KEY: Frameshift mutation ( i n s e r t i o n   o f   T ) producing stop codon
        ( B ) LOCATION: Nucleotide 13 of SEQ ID No.
            3 (corresponding to position between
            nucleotides 8529 and 8530 of SEQ. ID
            No. 1)
        ( D ) OTHER INFORMATION: SEQ ID No: 3 is
            the modified Tobacco Etch Virus coat
            protein gene present in pTC:RC.

( x ) PUBLICATION INFORMATION:
        ( A ) AUTHORS: J. A. Lindbo and W. G.
            Dougherty
        ( B ) TITLE: Pathogen-Derived Resistance to
            a Potyvirus: Immune and Resistant
            Phenotypes in Transgenic Tobacco
            Expressing Altered Forms of
            a Potyvirus Coat Protein Nucleotide
            Sequence
        ( C ) JOURNAL: Molecular Plant- Microbe
            Interactions
        ( D ) VOLUME: 5
        ( E ) ISSUE: 2
        ( F ) PAGES: 144-153
        ( A ) AUTHORS: J. A. Lindbo and W. G.
            Dougherty
        ( B ) TITLE: Untranslatable Transcripts of
            the Tobacco Etch Virus Coat Protein Gene Sequence Can Interfere with
Tobacco Etch Virus Replication in
Transgenic Plants and Protoplasts
(C) JOURNAL: Virology
(D) VOLUME: 189
(E) ISSUE: --
(F) PAGES: 725-733

(xi) SEQUENCE DESCRIPTION: SEQ ID NO: 3:

```
                                               ATG GCC ACT                   9
                                               Met Ser Thr

GTG TGA TGA TGGTGCTAGC GCTGGTAAGA AGAAAGATCA AAAGGATGAT                      58
Val

AAAGTCGCTG AGCAGGCTTC AAAGGATAGG GATGTTAATG CTGGAACTTC                      108

AGGAACATTC TCAGTTCCAC GAATAAATGC TATGGCCACA AAACTTCAAT                      158

ATCCAAGGAT GAGGGGAGAG GTGGTTGTAA ACTTGAATCA CCTTTTAGGA                      208

TACAAGCCAC AGCAAATTGA TTTGTCAAAT GCTCGAGCCA CACATGAGCA                      258

GTTTGCCGCG TGGCATCAGG CAGTGATGAC AGCCTATGGA GTGAATGAAG                      308

AGCAAATGAA AATATTGCTA AATGGATTTA TGGTGTGGTG CATAGAAAAT                      358

GGGACTTCCC CAAATTTGAA CGGAACTTGG GTTATGATGG ATGGTGAGGA                      408

TCAAGTTTCA TACCCGCTGA ACCAATGGT  TGAAAACGCG CAGCCAACAC                      458

TGAGGCAAAT TATGACACAC TTCAGTGACC TGGCTGAAGC GTATATTGAG                      508

ATGAGGAATA GGGAGCGACC ATACATGCCT AGGTATGGTC TACAGAGAAA                      558

CATTACAGAC ATGAGTTTGT CACGCTATGC GTTCGACTTC TATGAGCTAA                      608

CTTCAAAAAC ACCTGTTAGA GCGAGGGAGG CGCATATGCA AATGAAAGCT                      658

GCTGCAGTAC GAAACAGTGG AACTAGGTTA TTTGGTCTTG ATGGCAACGT                      708

GGGTACTGCA GAGGAAGACA CTGAACGGCA CACAGCGCAC GATGTGAACC                      758

GTAACATGCA CACACTATTA GGGGTCCGCC AGTGA                                      793
```

(2) INFORMATION FOR SEQ ID NO:4:

(i) SEQUENCE CHARACTERISTICS:
(A) LENGTH: 792
(B) TYPE: Nucleic acid
(C) STRANDEDNESS: Double
(D) TOPOLOGY: Circular (ii) MOLECULE TYPE: cDNA to genomic RNA (iii) HYPOTHETICAL: No (iv) ANTI-SENSE: Yes (v) FRAGMENT TYPE: N/A (vi) ORIGINAL SOURCE:
(A) ORGANISM: Tobacco Etch Virus
(B) STRAIN: Highly Aphid Transmitted
(C) INDIVIDUAL ISOLATE: N/A (vii) IMMEDIATE SOURCE:
(A) LIBRARY: No
(B) CLONE: pTC:AS (viii) POSITION IN GENOME: N/A (ix) FEATURE:
(A) NAME/KEY: --
(B) LOCATION: --
(C) IDENTIFICATION METHOD: --
(D) OTHER INFORMATION: SEQ ID No. 4 is the
modified Tobacco Etch Virus Coat protein gene present in pTC:AS. It is the
inverse complement of SEQ ID No. 2.

( x ) PUBLICATION INFORMATION:
  ( A ) AUTHORS: J. A. Lindbo and W. G.
    Dougherty
  ( B ) TITLE: Untranslatable Transcripts of
    the Tobacco Etch Virus Coat Protein Gene
    Sequence Can Interfere with Tobacco Etch Virus
    Replication in Transgenic Plants
    and Protoplasts
  ( C ) JOURNAL: Virology
  ( D ) VOLUME: 189
  ( E ) ISSUE: --
  ( F ) PAGES: 725-733
  ( A ) AUTHORS: J. A. Lindbo and W. G.
    Dougherty
  ( B ) TITLE: Pathogen-Derived Resistance to a
    Potyvirus: Immune and Resistant
    Phenotypes in Transgenic Tobacco
    Expressing Altered Forms of
    a Potyvirus Coat Protein Nucleotide
    Sequence
  ( C ) JOURNAL: Molecular Plant- Microbe
    Interactions
  ( D ) VOLUME: 5
  ( E ) ISSUE: 2
  ( F ) PAGES: 144-153

( x i ) SEQUENCE DESCRIPTION: SEQ ID NO: 4:

| | | | | | | |
|---|---|---|---|---|---|---|
| TCACTGGCGG | ACCCCTAATA | GTGTGTGCAT | GTTACGGTTC | ACATCGTGCG | CTGTGTGCCG | 60 |
| TTCAGTGTCT | TCCTCTGCAG | TACCCACGTT | GCCATCAAGA | CCAAATAACC | TAGTTCCACT | 120 |
| GTTTCGTACT | GCAGCAGCTT | TCATTTGCAT | ATGCGCCTCC | CTCGCTCTAA | CAGGTGTTTT | 180 |
| TGAAGTTAGC | TCATAGAAGT | CGAACGCATA | GCGTGACAAA | CTCATGTCTG | TAATGTTTCT | 240 |
| CTGTAGACCA | TACCTAGGCA | TGTATGGTCG | CTCCCTATTC | CTCATCTCAA | TATACGCTTC | 300 |
| AGCCAGGTCA | CTGAAGTGTG | TCATAATTTG | CCTCAGTGTT | GGCTGCGCGT | TTTCAACCAT | 360 |
| TGGTTTCAGC | GGGTATGAAA | CTTGATCCTC | ACCATCCATC | ATAACCCAAG | TTCCGTTCAA | 420 |
| ATTTGGGGAA | GTCCCATTTT | CTATGCACCA | CACCATAAAT | CCATTTAGCA | ATATTTTCAT | 480 |
| TTGCTCTTCA | TTCACTCCAT | AGGCTGTCAT | CACTGCCTGA | TGCCACGCGG | CAAACTGCTC | 540 |
| ATGTGTGGCT | CGAGCATTTG | ACAAATCAAT | TTGCTGTGGC | TTGTATCCTA | AAAGGTGATT | 600 |
| CAAGTTTACA | ACCACCTCTC | CCCTCATCCT | TGGATATTGA | AGTTTTGTGG | CCATAGCATT | 660 |
| TATTCGTGGA | ACTGAGAATG | TTCCTGAAGT | TCCAGCATTA | ACATCCCTAT | CCTTTGAAGC | 720 |
| CTGCTCAGCG | ACTTTATCAT | CCTTTTGATC | TTTCTTCTTA | CCAGCGTCAG | CACCAGCATC | 780 |
| CACAGTGCCC | AT | | | | | 792 |

PRODUCTION OF VIRUS RESISTANT PLANTS

This invention was made with government support under Grant No. DE-FG06-89-ER14047 from the Department of Energy, Grant No. DMB 89-02610 from the National Science Foundation and Grant No. 92-37303-7893, from the U.S. Department of Agriculture. The U.S. government has certain rights in this invention.

CROSS REFERENCE TO RELATED APPLICATION

This application is a continuation-in-part of application Ser. No. 07/838,509, filed Feb. 19, 1992, now abandoned.

FIELD OF THE INVENTION

This invention is directed generally to methods for producing virus resistant plants. The methods involve transforming plants with nucleic acid encoding a plus-sense untranslatable RNA molecule.

BACKGROUND OF THE INVENTION

The scientific art of plant breeding is aimed at the development of plants with new or modified traits. Plant breeding involves two main phases—the creation of genotypic variability and the selection of plants with particularly desired genotypes. Today, the penumbra of plant breeding encompasses both traditional methods of producing genotypic variability (crossing two plant lines to introduce traits from one to the other) and newer methods of genetic engineering. It is to such genetic engineering techniques that the present invention is directed.

Genetic engineering provides plant breeders with new tools with which to manipulate plant genomes. Rather than move large segments of plant genomes from one line to another by crossing related plant species, plant breeders can now introduce individually characterized genes into a particular plant line by genetic engineering. This technique not only provides a level of specificity not previously available, it also facilitates the transfer of genes into plants from completely unrelated plant species and indeed from viruses, bacteria, and animals.

Genetic engineering offers the hope of modifying many plant characteristics, including crop yield, stress tolerance and pathogen resistance. The regulation of gene expression is a key aspect of genetic engineering, and it is to this issue that the present invention is directed.

Plant viruses are responsible for major losses in worldwide crop production. Much effort is directed towards the development of new plant varieties which exhibit increased resistance to viral infection. Until recently such efforts were primarily based on the traditional plant breeding approach, however this approach is often limited by a lack of sources of resistance within the crop species. The advent of modern molecular biology techniques has facilitated the development of new methods of rendering plant varieties resistant to virus attack that are not limited by a requirement for preexisting resistance genes within a species.

Molecular Approaches

Many of these molecular approaches are based on the theory of pathogen derived resistance (Sanford and Johnston, 1985). This theory predicts that a "normal" host (plant)—pathogen (virus) relationship can be disrupted if the host organism expresses essential pathogen derived genes. It has been proposed that host organisms expressing pathogen gene products in excess amounts, at an inappropriate developmental stage, or in a dysfunctional form may disrupt the normal replicative cycle of the pathogen and result in an attenuated or aborted infection of the host.

Two approaches typify this pathogen derived resistance: coat protein mediated resistance and antisense RNA expression. Coat protein mediated resistance involves the production of transgenic plants expressing the coat protein gene of a particular virus. These plants may show an increased resistance to infection by that virus type. Coat protein mediated resistance has been demonstrated for several virus groups. While the mechanism of this resistance is not yet fully understood, it has been suggested that the presence of the plant synthesized coat protein prevents the removal of the protein coat (uncoating) of an invading virus and/or virus movement within the infected plant, leading to resistance. A major concern with this approach is the possible interaction between the viral coat protein expressed in the plant and other viral nucleic acids, which could potentially produce new strains of virus.

Antisense RNA technology involves the production of an RNA molecule that is complementary to the messenger RNA molecule of a target gene; the antisense RNA can potentially block all expression of the targeted gene. In the anti-virus context, plants are made to express an antisense RNA molecule corresponding to a viral RNA (that is, the antisense RNA is an RNA molecule which is complementary to a plus sense RNA species encoded by an infecting virus). Such plants may show a slightly decreased susceptibility to infection by that virus. Such a complementary RNA molecule is termed antisense RNA. It is thought that the plant encoded antisense RNA binds to the viral RNA and thus inhibits its function. This approach has only met with very limited success.

Potyviruses

The Potato Virus Y, or potyvirus, family represents a large number of plant viral pathogens which collectively can infect most crop species including both monocotyledonous and dicotyledonous plants. Potyvirus infection can induce a variety of symptoms including leaf mottling, seed and fruit distortion and can severely compromise crop yield and/or quality (Hollings and Brunt, 1981).

Potyviruses comprise a large family of aphid transmitted plant viruses that are members of the picornavirus superfamily (Goldbach, 1987). In general, potyviruses are flexous rod-shaped viruses with a single-strand plus sense RNA genome of circa 10,000 nucleotides which has a viral encoded protein linked to the 5' end and a 3' polyadenylate region. A single open reading frame codes for a polyprotein of approximately 350 kDa which is proteolytically processed into mature viral gene products. Nine individual gene products are released from the polyprotein by three proteinases which are part of the polyprotein (Riechmann et al., 1992).

The potyvirus RNA genome is encapsidated by approximately 2,000 copies of a coat protein monomer to form a virion. This capsid protein is encoded by the sequence present at the 3' end of the large open reading frame.

Potyviruses can be transmitted by aphids and in some instances can also be transmitted in the seeds of infected plants. Replication of the viral RNA is thought to occur in the cytoplasm of infected plant cells after uncoating. The replication mechanism involves both translation of the plus sense RNA to yield viral gene products (which include a replicase and a proteinase) and also the synthesis of a minus sense RNA strand. This minus sense strand then acts as a template for the synthesis of many plus sense genomes which are subsequently encapsidated in coat protein to yield infectious mature "virions," thus completing the replicative cycle of the virus.

Experiments have been reported in which transgenic plants expressing the coat protein gene of a potyvirus show a reduced susceptibility to virus infection (Lawson et al. 1990; Ling et al. 1991; Stark and Beachy 1989).

It is an object of the present invention to provide new methods of regulating gene expression that can be used to produce plants with a reduced susceptibility to virus infection.

SUMMARY OF THE INVENTION

The present invention includes methods and compositions for producing virus resistant transgenic plants. The invention is based in part on the discovery that an untranslatable RNA molecule can interfere with the expression of a virus gene that is homologous to the untranslatable RNA molecule. The invention is demonstrated by the production of plants that express a gene encoding an untranslatable RNA species. The untranslatable RNA species corresponds to the sense-strand (or "plus sense") RNA encoded by a target virus gene, the expression of which is to be suppressed.

In particular, the invention is illustrated by Examples describing the use of untranslatable plus sense RNA molecules in the production of plants with a reduced susceptibility to virus infection. Essentially, this is achieved by transforming a plant with a DNA sequence that encodes a plus-sense RNA molecule that is homologous to an RNA molecule required for replication of a target plant virus. A key feature of the invention is that the DNA sequence is selected such that the encoded RNA molecule cannot be translated by the plant cell ribosomes, i.e. the plus-sense RNA molecule is untranslatable. Expression of the DNA sequence within the plant causes the production of the untranslatable plus-sense RNA molecule in the plant cells. In turn, this untranslatable plus-sense RNA molecule inhibits replication of the target virus within the plant: the plant is thus rendered resistant to infection by the target virus.

One aspect of the present invention is thus the use of untranslatable plus sense RNA to produce virus resistant plants. As such, the invention provides an alternative and novel approach to rendering plants resistant to virus infection.

In one illustrative example, plants are transformed with a gene construct engineered to express an untranslatable form of the plus sense RNA which encodes the coat protein of the potyvirus Tobacco Etch Virus (TEV). Tobacco plants transformed with this gene construct accumulate the untranslatable plus sense RNA but do not produce detectable levels of the coat protein. It is shown that these plants are resistant to TEV infection. It is also shown that tobacco cells expressing this untranslatable plus sense RNA do not support TEV replication, unlike either control tobacco cells or tobacco cells which are engineered to express the plus sense translatable RNA, both of which support TEV replication and accumulate TEV coat protein.

A mechanism by which untranslatable RNA is proposed to suppress the expression of a target gene is presented. In light of the proposed mechanism and the following discussion and Examples, it will be apparent that the utility of the present invention is not limited to the production of virus resistant plants.

DESCRIPTION OF DRAWINGS

FIG. 1 is a diagram showing the normal course of gene expression for a hypothetical gene X.

FIG. 2 is a diagram illustrating the concept of using untranslatable plus-sense RNA to suppress the expression of hypothetical gene X.

FIG. 3 is a schematic representation of the construction of pTC:FL, utilized in construction of transformation vectors for the invention. Restriction endonuclease sites were introduced into pTL 37/8595 at positions A, B and C in the diagram. Following these nucleotide changes the mutated pTL 37/8595 was digested with the restriction enzyme NcoI, the DNA fragment delineated by the restriction enzyme sites at B and C was removed, and the plasmid relegated to generate pTC:FL. pTC:FL contains the Tobacco Etch Virus (TEV) coat protein nucleotide sequence flanked by BamHI restriction sites and the TEV 5' and 3' untranslated sequences (UTS). T7 and SP6 promoters are also shown. Abbreviations used in this diagram are as follows: T7, T7 RNA polymerase promoter sequence; SP6, SP6 RNA polymerase promoter sequence; ori, origin of replication; M13 ori, bacteriophage M13 single-stranded origin of replication; amp$^r$, β-lactamase gene. The solid black area represents TEV genome cDNA nucleotides 144 to 200 and the striped area represents a portion of the TEV NIb gene (TEV nt 8462–8517). The region marked TEV CP gene is the cDNA of TEV nt 8518–9309.

FIG. 4 is a schematic representation of the various transgenes used in the Examples set forth herein. The left hand column shows the designations used for the plant lines transformed with particular transgenes. The second column shows the transgene constructs. The third column shows the products produced by expression of the various transgene constructs in plants. The fourth column shows the field phenotypes of plant transformed with particular transgene constructs. Nomenclature and abbreviations are as described in the text and in Whitty et al. (1994), which is herein incorporated by reference.

FIGS. 5A and 5B are graphic representations of the appearance of systemic symptoms in plants infected with TEV showing responses of control plants and transformed plants generated as described in Example 1. FIG. 5A represents results obtained by mechanically inoculating ten B49 (wild type) plants and ten R2 plants of transgenic plant lines 35S #4, FL #3, FL #24, homozygous for the inserted TEV gene, with TEV infected plant sap. FIG. 5B represents results obtained by mechanically inoculating 20 B49 plants and 20 R2 plants of lines AS #3 and RC #7 directly with a TEV suspension.

FIG. 6 is a diagram showing the essential differences between the RC constructs described in Example 1 and the 2RC constructs described in Example II. The main difference lies in the sequences which constitute the 5' and 3' UTR.

FIG. 7 is a diagrammatic representation of the various potyvirus Y (PVY) transgene constructs introduced into potato and tobacco as described in Examples IV and V.

FIG. 8 Illustrates the fundamental difference between untranslatable plus-sense RNA and antisense RNA, using a hypothetical gene sequence.

SEQUENCE LISTINGS

Nucleotide and amino acid sequences are set forth in the accompanying "Sequence Listing." Sequence ID No. 1 sets forth the nucleotide sequence of the cDNA corresponding to the Tobacco Etch Virus genome. Sequence ID No. 2 sets forth the nucleotide sequence of the modified Tobacco Etch Virus coat protein gene present in clone pTC:FL and the amino acid sequence of the protein encoded by this gene. Sequence ID No. 3 sets forth the nucleotide sequence of the modified Tobacco Etch Virus coat protein gene present in clone pTC:RC and the amino acid sequence of the protein encoded by this gene. Sequence ID No. 4 sets forth the nucleotide sequence of the modified Tobacco Etch Virus coat protein gene present in clone pTC:AS and the amino acid sequence of the protein encoded by this gene.

DETAILED DESCRIPTION

Definitions and abbreviations

Susceptible plant: A plant that supports viral replication and displays virus-induced symptoms.

Resistent plant: A plant wherein virus-induced symptoms are attenuated and virus replication is attenuated.

Plus sense RNA (also termed sense-strand RNA or sense RNA): An RNA molecule that can serve directly as messenger RNA, i.e. that can be translated by ribosomes.

Minus sense RNA (also termed antisense RNA): RNA that is complementary to plus sense RNA.

$R_0$ generation: Primary transformants.

$R_1$ generation: Progeny of primary transformants.

$R_2$ generation: Second generation progeny of $R_0$ generation (i.e., progeny of $R_1$, generation).

TEV: Tobacco Etch Virus.

PVY: Potyvirus Y

GENERAL DESCRIPTION

The present invention provides a new and effective method for suppressing the expression of a target gene. In particular, the invention is directed at suppressing the expression of virus genes in plants in order to produce virus resistant plants.

Figure 1:
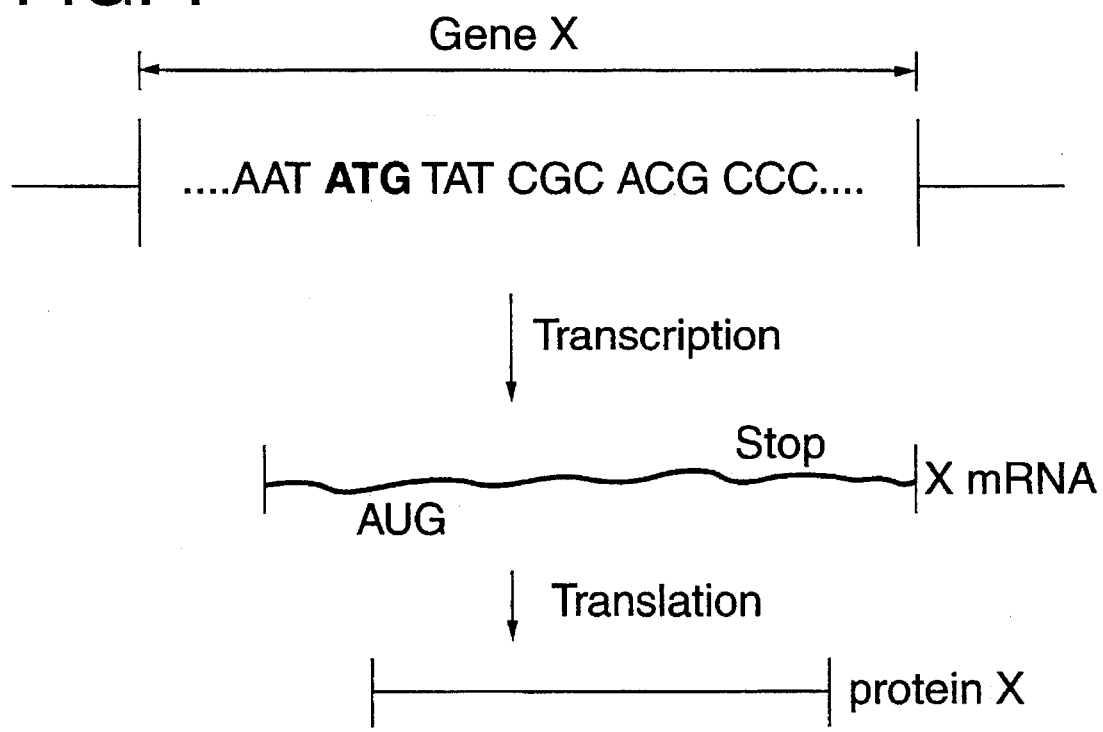

A central feature of the invention is the discovery that an untranslatable plus-sense RNA sequence is highly effective in suppressing the expression of a corresponding homologous gene. The basic principle of the invention is shown schematically in FIGS. 1 and 2. FIG. 1 illustrates the normal course of gene expression for hypothetical gene X. The DNA sequence that includes gene X is transcribed by DNA dependent RNA polymerass II, to produce a corresponding messenger RNA sequence (X mRNA). In turn, X mRNA is translated by ribosomes, starting at the AUG translation initiation codon, to produce protein X.

Figure 2:
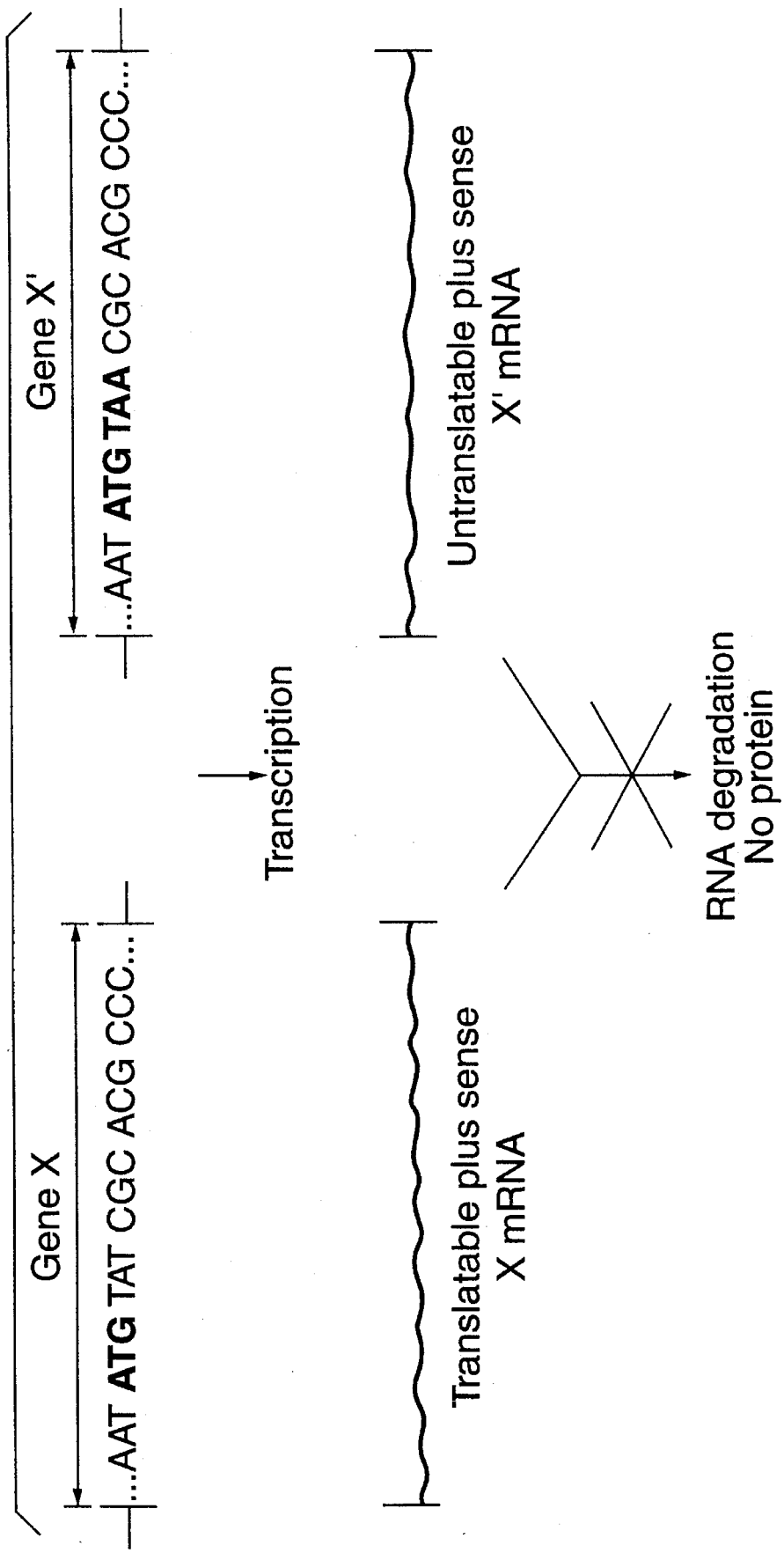

FIG. 2 illustrates the use of untranslatable plus sense RNA to suppress expression of gene X. Essentially, the target cell containing gene X is transformed with a DNA sequence (X') that is homologous to gene X, except that the sequence has been modified to render the X' RNA molecule untranslatable. In this example the modification that renders the X' RNA untranslatable is the insertion of a translation stop codon (TAA) that signals termination of translation, immediately after the translation initiation codon in the X' DNA sequence. The presence of both X mRNA and X' mRNA within the cell leads to the suppression of expression of gene X: production of protein X is inhibited and therefore the function performed by protein X is absent from the cell.

The working Examples provided below relate to the suppression of virus genes in plants. That is, in the Examples, gene X is a virus gene and the host cell is a plant cell being infected by the virus; the untranslatable plus-sense RNA is effective in inhibiting replication of the virus and thus rendering the plants resistant to virus infection.

Practicing the present invention requires the manipulation of DNA sequences using molecular biological techniques. DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR. Details of these techniques are provided in standard laboratory manuals such as Sambrook et al. (1989), herein incorporated by reference, and Ausubel et al. (1992), herein incorporated by reference.

Suppression of a target virus gene using the method provided by this invention will be carried out using the concept of expressing, in a host cell, an untranslatable plus sense RNA that is homologous to the target gene. In a preferred embodiment of the invention, the untranslatable plus-sense RNA is encoded by a DNA molecule that is introduced into the genome of the host cell. For clarity, the DNA molecule that encodes the untranslatable plus-sense RNA will be referred to in the following discussion as the "untranslatable DNA sequence".

Application of the present invention will require selection of particular parameters and conditions, depending on factors such as the sequence of the target gene to be suppressed, the type of cell in which the suppression is to occur and the normal timing of expression of the target gene. Variations in these factors will affect the selection of the introduced DNA sequence that encodes the untranslatable plus-sense RNA, the regulatory sequences linked to the DNA sequence to be introduced, the type of transformation vector to be used and the method of transformation to be used.

Selection of the untranslatable DNA sequence

A key aspect of the present invention is the selection of the untranslatable DNA sequence, i.e. the selection of a DNA sequence that encodes an untranslatable plus-sense RNA molecule that is homologous to the target virus gene to be suppressed. The untranslatable DNA sequence will be homologous to the target virus gene sequence, and thus knowledge of the target gene sequence is a prerequisite to practicing this invention.

According to the present invention, a DNA molecule homologous to the target virus gene is manipulated so as to render the RNA molecule encoded by the DNA molecule untranslatable. The molecule may be rendered untranslatable by several different means. A preferred means of rendering the RNA molecule untranslatable is to introduce into the DNA molecule one or more premature "stop" codons. A stop codon is a codon of the genetic code that signals ribosomes to terminate translation of a messenger RNA molecule. There are three stop codons in the genetic code: TAA, TAG and TGA as illustrated in Table 1 below.

TABLE 1

| First Position (5' end) | Second Position | | | | Third Position (3' end) |
|---|---|---|---|---|---|
| | T | C | A | G | |
| T | Phe | Ser | Tyr | Cys | T |
| | Phe | Ser | Tyr | Cys | C |
| | Leu | Ser | STOP (och) | STOP | A |

TABLE 1-continued

The Genetic Code

| First Position (5' end) | Second Position | | | | Third Position (3' end) |
|---|---|---|---|---|---|
| | T | C | A | G | |
| C | Leu | Ser | STOP (amb) | Trp | G |
| | Leu | Pro | His | Arg | T |
| | Leu | Pro | His | Arg | C |
| | Leu | Pro | Gln | Arg | A |
| | Leu | Pro | Gln | Arg | G |
| A | Ile | Thr | Asn | Ser | T |
| | Ile | Thr | Asn | Ser | C |
| | Ile | Thr | Lys | Arg | A |
| | Met | Thr | Lys | Arg | G |
| G | Val | Ala | Asp | Gly | T |
| | Val | Ala | Asp | Gly | C |
| | Val | Ala | Glu | Gly | A |
| | Val (Met) | Ala | Glu | Gly | G |

"STOP (och)" stands for the ochre termination triplet, and "STOP (amb)" for the amber. ATG is the most common initiator codon; GTG usually codes for valine, but it can also code for methionine to initiate an mRNA chain.

One or more stop codons can be inserted into the DNA sequence or, alternatively, the sequence can be mutated to convert an existing triplet codon that codes for an amino acid into a stop codon. For example, the hypothetical gene sequence:

... CTT AAC TGG TCC ...

would normally be translated by ribosomes to produce the polypeptide:

... Leu Asn Trp Ser ...

This sequence can be rendered untranslatable by introduction of a stop codon, such as TAA, into the sequence. For example:

... CTT TAA AAC TGG TCC ...

This modified sequence encodes:

... Leu STOP

Alternatively, substitution of the ninth nucleotide, guanosine (G), by the nucleotide adenosine (A) will result in the creation of a premature stop codon, rendering the sequence untranslatable:

... CTT AAC TGA TCC ...

which encodes:

... Leu Asn STOP

Alternatively, the addition of one or more bases into the sequence (except multiples of three bases) can be used to displace the reading frame of the DNA sequence which can also have the effect of rendering the RNA molecule untranslatable. For example, the introduction of a single nucleotide (G) into the first codon creates a new reading frame containing a premature stop codon:

... CTG TAA CTG GTC C ...

which encodes:

... Leu STOP

One or more of the above approaches may be used to render the RNA molecule encoded by the DNA molecule untranslatable. It will be appreciated that a very large number of sequence changes can be made, the precise nature of which will depend on the actual sequence being manipulated, to render the sequence untranslatable. In preferred embodiments, more than one stop codon will be introduced into the DNA sequence in order to render it untranslatable. Preferably, the stop codons introduced into the DNA sequence to render the corresponding RNA untranslatable will be introduced at the beginning of the coding region of the DNA molecule. Preferably, one or more stop codons will be introduced within 200 nucleotides of the translation initiation ATG codon, more preferably within 50 nucleotides and most preferably within 10 nucleotides. However, these preferences will vary with the length of the DNA molecule itself. Moreover, it will be apparent that any mutation that renders the RNA molecule untranslatable may be effective in this invention, regardless of its position relative to the initiation ATG codon.

An alternative and less preferred means of rendering the encoded RNA molecule untranslatable is to remove the translation initiation codon (usually ATG) from the DNA sequence. This method is less preferred as the ribosomes may be able to use another ATG codon elsewhere in the DNA sequence to initiate translation. Removal of the initiation ATG is therefore best used in conjunction with the insertion of premature stop codons into the sequence.

Many standard DNA mutagenesis techniques are available to modify DNA sequences in the ways described above including, for example, M13 primer mutagenesis. Details of such techniques are provided in Sambrook et al. (1989), chapter 15, herein incorporated by reference, and in Ausubel et al. (1992), chapter 8. herein incorporated by reference.

A proposed mechanism for the suppression of a target virus gene by the introduction into the cell of a DNA molecule encoding an untranslatable plus sense RNA molecule homologous to the target gene involves the activity of an inducible, cytoplasmic-based, cellular activity that degrades specific kNA sequences. This mechanism would require the RNA molecule encoded by the target DNA sequence and the plus sense untranslatable RNA molecule encoded by the introduced DNA sequence to be sufficiently similar such that each is recognized by the RNA sequence specific cellular system. This means that the target DNA sequence and the DNA sequence encoding the untranslatable plus sense RNA molecule must share some sequence identity.

In the Examples presented below, the DNA sequence encoding the untranslatable RNA molecule is derived directly from the target virus nucleotide sequence and differs primarily only by the presence of premature stop codons inserted by mutagenesis. Thus, in these examples, the DNA molecule encoding the untranslatable plus sense RNA molecule is over 90 percent homologous to the target DNA sequence. However, it is anticipated that the present invention can be practiced using introduced DNA molecules encoding plus sense untranslatable RNA molecules wherein the introduced DNA molecules is less than 90 percent homologous to the target DNA molecule. That is, it is anticipated that the DNA molecule encoding the untranslatable plus sense RNA molecule will be effective when it shares at least 80% sequence homology with the target DNA sequence. In a more preferred embodiment, the DNA molecule encoding the untranslatable plus sense RNA molecule will share at least 85% homology to the target DNA molecule.

Although the examples provided below describe constructs in which the DNA molecule encoding the untranslatable RNA molecule corresponds to the full length of the target DNA molecule, it is anticipated that substantially less than the full length of the target DNA molecule can be used in the introduced untranslatable DNA molecule. For example, it is anticipated that, under some circumstances, a DNA molecule encoding a plus sense untranslatable RNA molecule wherein the DNA molecule corresponds to a portion of the target DNA molecule will be effective. The rationale for this concept is that the RNA sequence specific cellular activity that recognizes the over expression of a particular RNA sequence may recognize specific, short regions of a target RNA sequence. Thus, the DNA sequence encoding the untranslatable plus sense RNA molecule would be effective in suppressing expression of the target gene provided the encoded untranslatable plus sense RNA molecule contained the target gene RNA sequence recognized by the RNA sequence specific cellular activity. Accordingly, it is anticipated that relatively short regions of the target DNA molecule may be used to produce the DNA molecule encoding the untranslatable plus sense RNA.

In preferred embodiments, the introduced DNA sequence will be at least 50–100 nucleotides in length, although longer sequences, such as 100–250 nucleotides are preferred. In more preferred embodiments, a sequence of greater than 500 nucleotides would be used, depending on the size of the target gene. In embodiments where such shorter sequences (i.e. less than 250 nucleotides) are utilized, it is anticipated that the introduced DNA sequence will share a high degree of homology with the target gene sequence, preferably at least 80%.

Hence, the present invention is a method of suppressing the expression of a virus gene in a plant cell comprising transforming the plant cell with a nucleic acid molecule that is homologous to the virus gene and wherein the nucleic acid molecule encodes an untranslatable plus-sense RNA molecule. In one embodiment of the invention, the nucleic acid molecule used in this method comprises at least one contiguous nucleic acid sequence of at least 50 nucleotides in length that is at least 80% homologous to the virus gene. In a more preferred embodiment, the nucleic acid molecule comprises at least one contiguous nucleic acid sequence of at least 100 nucleotides in length that is at least 80% homologous to the virus gene. In a yet more preferred embodiment, the nucleic acid molecule comprises at least one contiguous nucleic acid sequence of at least 250 nucleotides in length that is at least 85% homologous to the virus gene.

The present invention is not limited to the suppression of a single target virus gene. That is, it is possible to suppress the expression of multiple genes using a single introduced DNA molecule that contains untranslatable plus sense RNA sequences corresponding to several genes expressed in the target cell. This approach could be used to enhance resistance to a single virus or to produce resistance to multiple viruses in a single plant. As illustrated in the examples below, the replication of an invading virus in plant cells can be halted by the introduction of a DNA molecule encoding an untranslatable plus sense RNA molecule homologous to a virus gene essential to replication of the virus. This approach allows the production of transgenic plants resistant to the virus. An elevated level of virus resistance may be produced by introducing into the plant cells a DNA sequence that encodes plus-sense untranslatable RNA molecules corresponding to more than one gene required for virus replication.

It will be appreciated that the efficacy of the present invention depends on the transcription of the introduced DNA sequence. Transcription of a DNA sequence into messenger RNA is preferably arranged by including a promoter region at the 5' end of the introduced DNA sequence, together with regulatory sequences at the 3' end of the DNA sequence. Many promoter sequences and 3' regulatory sequences have now been identified in a wide range of viral, bacterial, fungal, plant and animal genes. One option for suitable promoter sequences and 3' regulatory sequences are the native sequences present in the target gene (gene X in the above hypothetical). These regulatory sequences may be particularly suitable as they would result in coordinate expression of the target gene and the introduced DNA sequence encoding the untranslatable plus sense RNA (gene X'). The selection of suitable promoter and 3' regulatory sequences is within the skill of the artisan. After selecting and incorporating regulatory DNA sequences, the untranslatable DNA molecule will be incorporated into a suitable vector for transformation into the host cell. The selection of regulatory sequences, as well as the selection of a suitable transformation vector will depend on the type of host cell into which the untranslatable DNA sequence is to be introduced and the transformation method selected. Vectors suitable for transforming plant cells (derived from either monocotyledonous or dicotyledonous plants) are described below. Transformation of both monocotyledonous and dicotyledonous plant cells is now routine and the selection of the most appropriate transformation technique will be determined by the practitioner.

A number of promoters which are active in plant cells have been described in the literature. Promoters which are known or are found to cause transcription of RNA in plant cells can be used when the present invention is applied to suppress gene expression in plants. Such promoters may be obtained from plants or viruses and include, but are not limited to, the CaMV 35S promoter. It is preferred that the particular promoter selected should be capable of causing sufficient expression to result in the production of an effective amount of untranslatable plus sense RNA to suppress expression of the target gene. The amount of untranslatable plus sense RNA needed to suppress expression of the target gene may vary with the target gene, its expression levels and the plant type. Accordingly, while the 35S promoter is preferred in the Examples presented below, it should be understood that this promoter may not be the optimal one for all embodiments of the present invention in plants. Furthermore, the promoters used in the DNA constructs of the invention may be modified, if desired, to affect their control characteristics. DNA sequences have been identified which confer regulatory specificity on promoter regions. For example, the small subunit of the ribulose bis-phosphate carboxylase (ss RUBISCO) gene is expressed in plant leaves but not in root tissues. A sequence motif that represses the expression of the ss RUBISCO gene in the absence of light, to create a promoter which is active in leaves but not in root tissue, has been identified. This and/or other regulatory sequence motifs may be ligated to promoters such as the CaMV 35S promoter to modify the expression patterns of a gene. Chimeric promoters so constructed may be used as described herein. For purposes of this description, the phrase "CaMV 35S promoter" will therefore include all promoters derived by means of ligation with operator regions, random or controlled mutagenesis, as well as tandem or multiple copies of enhancer elements, and the like.

The 3' nontranslated region of genes which are known or are found to function as polyadenylation sites for RNA in plant cells can be used in the present invention. Such 3' nontranslated regions include, but are not limited to, the 3' transcribed, nontranslated region of the CaMV 35S gene and the 3' transcribed, nontranslated regions containing the polyadenylation signals of the tumor-inducing (TI) genes of Agrobacterium, such as the tumor morphology large (tml) gene. For purposes of this description, the phrase "CaMV 35S 3' nontranslated region" will therefore include all such appropriate 3' nontranslated regions.

A DNA construct in accordance with the present invention is introduced, via a suitable vector and transformation method as described below, into plant cells and plants transformed with the introduced DNA are regenerated. Various methods exist for transforming plant cells and thereby generating transgenic plants. Methods which are known or are found to be suitable for creating stably transformed plants can be used in this invention. The choice of method will vary with the type of plant to be transformed; those skilled in the art will recognize the suitability of particular methods for given plant types. Suitable methods may include, but are not limited to: electroporation of plant protoplasts; liposome mediated transformation; polyethylene mediated transformation; transformation using viruses; microinjection of plant cells; microprojectile bombardment of plant cells and *Agrobacterium tumefaciens* (AT) mediated transformation.

In an embodiment of the current invention, the DNA sequences comprising the CaMV 35S promoter and CaMV 35S nontranslated 3' region and the mutated cDNA encoding an untranslatable plus sense RNA derived from the TEV coat protein gene are combined in a single cloning vector. This vector is subsequently transformed into AT cells and the resultant cells are used to transform cultured tobacco cells.

Vectors suitable for the AT mediated transformation of plants with the DNA of the invention are disclosed in the Examples. It will be obvious to one skilled in the art that a range of suitable vectors is available, including those disclosed by Bevan (1984), Herrera-Estrella et al. (1983), and EPO publication 12,516 (Schilperoort et al.). Suitable vectors are available on a commercial basis from Clontech (Palo Alto, Calif.) and Pharmacia LKB (Pleasant Hill, Calif.) and other sources.

Use of untranslatable RNA to suppress virus gene expression in plants

Illustrative of the present invention is the use of the disclosed method to suppress virus gene expression in plants and thereby to produce plants with a reduced susceptibility to virus infection. Plants resistant to a variety of virus types can be produced by this method; in the examples discussed below, plants are rendered resistant to potyvirus infection, and in particular to infection by Tobacco Etch Virus (TEV).

In described embodiments of the present invention, an untranslatable plus sense RNA molecule is encoded by a DNA molecule introduced into a plant cell. The DNA molecule comprises a DNA sequence homologous to a plant virus gene and DNA from heterologous sources. The DNA from heterologous sources includes elements controlling the expression of the virus-homologous DNA sequence. The sequence of the virus-homologous DNA is selected such that the RNA molecule transcribed from it is untranslatable. The presence of this untranslatable plus sense RNA within the cells of the transformed plant reduces the susceptibility of the plant to viral infection.

The DNA constructs of the disclosed embodiment contain, in double-stranded DNA form, a portion of a cDNA version of the single-stranded RNA genome of TEV. In potyviruses, including TEV, the viral genome includes genes encoding the coat protein, a replicase enzyme and a proteinase. One disclosed embodiment utilizes the region of the genome encoding the coat protein gene. In considering the present invention and the evidence for the proposed mechanism by which an untranslatable plus sense RNA molecule can inhibit viral replication, those skilled in the art will recognize that other portions of a potyvirus genome could be substituted for the coat protein gene. Furthermore, it will be apparent that suitable genomic portions are not limited to complete gene sequences.

Transformed plants are then assessed for resistance to the virus. The assessment of resistance or reduced susceptibility may be manifest in different ways dependant on the particular virus type and plant type. Those skilled in the art will realize that a comparison of symptom development on a number of inoculated untransformed plants with symptom development on similarly inoculated transformed plants will provide a preferred method of determining the effects of transformation with the specified DNA molecule on plant resistance. Symptoms of infection include, but are not limited to leaf mottling, chlorosis and etching. Plants showing increased viral resistance may be recognized by delay in appearance of such symptoms or attenuation or total lack of such symptoms.

To test plants for virus resistance, plants are preferably exposed to the virus at a concentration within a range where the rate of disease development correlates linearly with virus concentration. Methods of virus inoculation are well known in the art and are reviewed in Kado and Agrawai (1972). One such method includes abrading a leaf surface with an aqueous suspension containing virus and an abrasive material such as carborundum. Alternatively, the virus suspension can be directly inoculated into leaf veins, or insect vectors may be employed. The virus suspension may comprise purified virus or sap from virus infected plants.

Notwithstanding the variable parameters described above, the selection of which is within the skill of the ordinary artisan, application of the disclosed method to suppress the expression of a target gene will involve the central concept of expressing an untranslatable plus-sense RNA molecule that is homologous to the target gene to be suppressed.

The following Examples describe illustrative applications of the invention. In these Examples, conventional molecular biology and biochemistry techniques are employed unless otherwise stipulated. Conventional techniques for use in practicing the present invention, such as isolation of DNA, restriction enzyme digestion of DNA, ligation of DNA molecules, vector construction, DNA sequencing and transformation, are described in Sambrook et al. (1989) *Molecular Cloning, A Laboratory Manual* (2d Ed.), Cold Spring Harbor Laboratory Press, Cold Spring Harbor, N.Y.; and Ausubel et al. (1992) *Current Protocols in Molecular Biology*, Greene Publishing and Wiley Interscience, New York, hereby incorporated by reference. Reagents and materials were purchased from commercial sources.

EXAMPLE I

Production of plants showing reduced susceptibility to TEV infection using RC constructs

1.1 Construction of a gene encoding untranslatable plus sense RNA molecule

The Highly Aphid Transmissible (HAT) isolate of Tobacco Etch Virus (TEV) was obtained from Dr. Tom Pirone (University of Kentucky) and maintained in *Nicotiana tabacum* (Burley 21). The virus was purified from *Nicotiana tabacum* (Burley 21) 20 to 30 days following inoculation. Viral purification and RNA isolation procedures have been described (Dougherty and Hiebert (1980a). Complementary DNA (cDNA) was synthesized, made double-stranded and inserted into the bacterial plasmid pBR322 as described by Allison et al. (1985a, 1985b, 1986), herein incorporated by reference. cDNA synthesis was accomplished as follows: Purified viral RNA primed with oligo(dT$_{12-18}$) served as a template for single-strand CDNA synthesis by reverse transcriptase. Following the addition of homopolymeric tracts of deoxycytidine 5' monophosphate, second-strand synthesis, primed with oligo(dG$_{12-18}$), was completed with DNA polymerase I. SalI and EcoRI linkers were ligated to the double-stranded cDNA and inserted into the bacterial plasmid pBR322 (Kurtz and Nicodemus 1981). The resulting cDNA clones were screened by colony hybridization (Hanahan and Meselson 1980) with oligo(dT$_{12-18}$) primed, $^{32}$P-labeled single-stranded TEV cDNA. Plasmid DNA was isolated from colonies which hybridized with the probe, and the SalI/EcoRI cDNA inserts were sized by electrophoresis in a 0.8% (w/v) agarose gel using a horizontal water-cooled gel apparatus.

The SalI/EcoRI inserts from the recombinant molecules were isolated from an agarose gel with NA45 membrane (Schleicher & Schuell, Keene, N. H.) according to the manufacturer's protocol. The following restriction enzymes were used either alone or in combination to digest the isolated cDNA insert: HindIII, XhoI, AluI, HaeIII, RsaI, Sau3A, and TaqI. Restriction enzyme digestion products were inserted into the DNA of an appropriate M13 bacteriophage (Messing 1983) selected for the presence of corresponding polylinker restriction sites, and their nucleotide sequences were determined by dideoxy chain termination.

Figure 3:
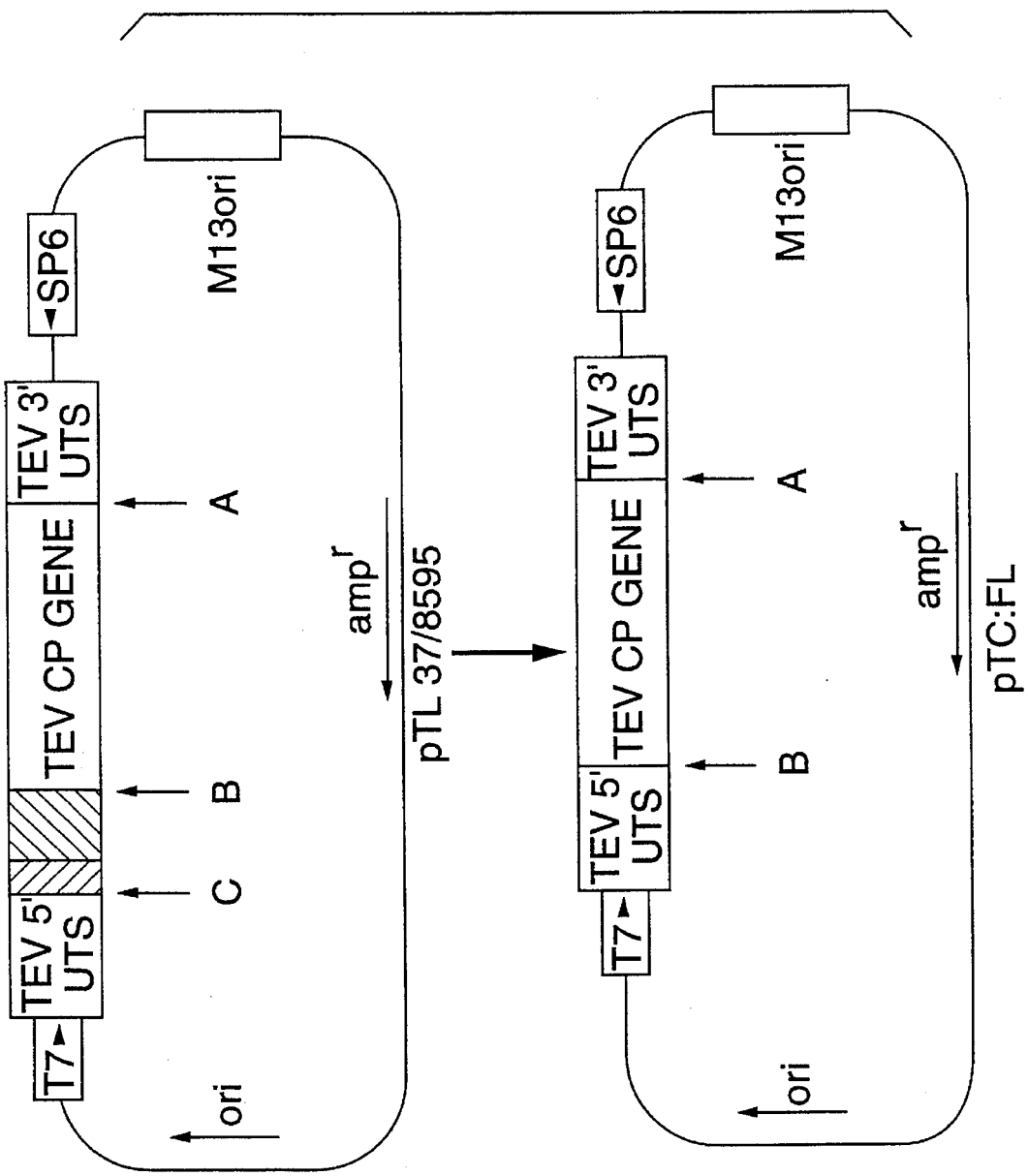

Plasmid pTL 37/8595 (Carrington and Dougherty 1987; Carrington et al. 1987, herein incorporated by reference) contains a cDNA copy of the genomic sequence of HAT TEV corresponding to nucleotides (nt) 1–200 and nt 8462–9495 (FIG. 3). (Numbering of the TEV genome nucleotides is according to that presented in Allison et al. 1986, herein incorporated by reference. The TEV genome sequence is set forth as SEQ I.D. No. 1 in the accompanying sequence listing.) The first and last codons of the coat protein (CP) coding region in the TEV genome are nt 8518–8520 (encoding the amino acid serine) and 9307–9309 (opal stop codon) respectively. pTL 37/8595 was subject to in vitro site-directed mutagenesis as described by Taylor et al. (1985a, 1985b). In all cases, nucleotide changes were confirmed by dideoxy-nucleotide sequencing (Sanger et al. 1977).

TEV nt 9312–9317 were first mutated (FIG. 3) to generate a BamHI restriction site (GGATCC). TEV nt 8516–8521 were then altered to generate an NcoI site (CCATGG), changing the first codon of the TEV CP coding region from AGT (Ser), to ATG (Met). A single oligonucleotide was then used to mutate TEV nt 133–138 to a BamHI restriction site (GGATCC), nt 142 to a deoxyadenylate residue and nt 143–148 to an NcoI restriction site (CCATGG). These mutations generated an NcoI site centered on the first codon of the TEV ORF and in a good translational start context as described by Kozak (1984). Digestion of the resulting plasmid with the restriction enzyme NcoI; removing TEV nt #143–200/8462–8516, and religation generated plasmid pTC:FL. pTC:FL contained the TEV CP gene flanked by BamHI restriction sites and TEV 5' and 3' untranslated sequences (see FIG. 3).

Plasmid pTC:RC (RNA Control, producing untranslatable plus sense RNA) was generated by insertion of a single deoxythymidylate residue after TEV nt 8529, and point mutations of TEV nt 8522 (G to C), 8534 (C to A), 8542 (G to A), and 8543 (A to G) to create a frameshift mutation immediately followed by three stop codons. An NheI restriction site (GCTAGC) was simultaneously generated, for screening identification purposes, at nt 8539–8544.

All plasmids described above were linearized with HindIII, transcribed with T7 RNA polymerase (Melton et al. 1984), and translated in a rabbit reticulocyte lysate containing $^{35}$S Methionine (Dougherty and Hiebert 1980a). Radiolabeled translation products were analyzed by electrophoretic separation on a 12.5% acrylamide gel containing SDS (Laemmli 1970) and detected by autoradiography. Transcripts of plasmid pTC:RC produced no detectable protein products, while transcripts from pTC:FL produced TEV coat protein of the expected sizes.

Additionally, the full length TEV CP open reading frame of pTC:FL was inserted in the reverse orientation to make the antisense (AS) construct pTC:AS.

The nucleotide sequences of the modified coat protein genes in clones pTC:FL, pTC:RC and pTC:AS are set forth in the accompanying Sequence Listing as Seq. I.D. Nos. 2, 3 and 4, respectively.

1.2 Production of plant transformation vector

The various forms of the CP nucleotide sequence were then inserted as BamHI cassettes into the plant expression vector pPEV. FIG. 4 illustrates diagrammatically various aspects of the transgene sequences utilized in this and the following Examples. The vector pPEV is part of a binary vector system for *Agrobacterium tumefaciens* mediated plant cell transformation. Plasmid pPEV was constructed from the plasmids pCGN 2113 (Calgene), pCIB 710 and pCIB 200 (Ciba Geigy Corp.). pCGN 2113 contains the "enhanced" Cauliflower Mosaic Virus (CaMV) 35S promoter (CaMV sequences –941 to 90/–363 to +2, relative to the transcription start site) in a pUC derived plasmid backbone. pCIB 710 has been described (Rothstein et al. 1987) and pCIB 200 is a derivative of the wide host range plasmid pTJS 75 (Schmidhauser and Helinski 1985) which contains left and right *A. tumefaciens* T37 DNA borders, the plant selectable NOS/NPT II chimeric gene from the plasmid Bin 6 (Bevan 1984) and part of a pUC polylinker. The small EcoRI-EcoRV DNA fragment of pCIB 710 (Rothstein et al. 1987) was ligated into EcoRI-EcoRV digested pCGN 2113. This regenerated the enhanced CaMV 35S promoter (Kay et al. 1987) of pCGN 2113 and introduced the CaMV 35S 5' and 3' untranslated sequences into pCGN 2113. The CaMV 35S promoter/terminator cassette of the resulting plasmid was isolated as an EcoRI-XbaI DNA fragment and ligated into EcoRI-XbaI digested pCIB 200 to generate pPEV. CP nucleotide sequences from pTC:FL, pTC:RC, and pTC:AS were cloned as BamHI cassettes into BamHI digested pPEV and orientation of inserts confirmed by digestion with appropriate restriction endonucleases.

1.3 Transformation and Regeneration of Tobacco pPEV plasmids containing TEV CP ORFs were mobilized from *E. coli* HB101 into *A. tumefaciens* A136 containing plasmid pCIB 542 (Ciba Geigy), using the helper plasmid pRK 2013 in *E. coli* HB101 and the tri-parental mating system of Ditta et al. (1980). Plasmid pCIB 542 supplied vir functions necessary for T-DNA transfer.

Leaf discs of *Nicotiana tabacum* cv Burley 49 were transformed and whole plants regenerated according to Horsch et al. (1985). Transformed tissue was selected by culturing callus on MS plates (Murashige and Skoog 1962) containing 1 µg/ml 6-benzylaminopurine (Sigma Corp.), 01 µg/ml α-naphthaleneacetic acid (Sigma Corp.), 050 µg/ml carbenicillin and 100 µg/ml Kanamycin sulfate (Sigma Corp.). Shoots were rooted on MS plates containing 500 µg/ml carbenicillin and 100 µg/ml kanamycin sulfate, and plantlets were transplanted into soil and transferred directly into the greenhouse approximately 2–3 weeks after rooting.

R0, R1 and R2 generation plants were screened by western and/or northern blot analyses. R2 seed (ca. 100 seeds per R2 plant) was screened for the kanamycin-resistant phenotype (kan$^r$) by surface sterilizing seed in 10% bleach for 5 min., washing twice in sterile water and germinating on MS plates containing 100 µg/ml kanamycin sulfate. R2 seed lines which were 100% kanamycin resistant were screened by western blot analysis for expression of TEV coat protein. The transgenic plant lines generated, the transgenes introduced into these lines, the expected products and the nomenclature assigned to these lines are shown in FIG. 4.

1.4 Molecular Analyses of Transgenic Plants

Transgenic tobacco plants were analyzed by western and northern blot analyses to determine the nature of protein and RNA products produced respectively. Total RNA samples isolated from the various transgenic lines were analyzed in northern blot hybridization studies. Total nucleic acids were isolated from tissue and RNA precipitated with LiCl as described by Verwoerd et al. (1989). RNAs were electrophoretically separated on 1.2% agarose gels containing 6% (v/v) formaldehyde and transferred to nitrocellulose. Prehybridization and hybridization conditions were as described in Sambrook et al. (1989). Strand specific riboprobes were generated from SP6 or T7 DNA dependent RNA polymerase transcription reactions of pTL 37/8595 linearized with the restriction enzymes Asp718 (Boehringer Mannheim, Indianapolis, Ind.) or HindIII, respectively, using α-labelled $^{32}$P-CTP ribonucleotide and suggested procedures (Promega, Madison, Wis.).

An RNA transcript of approximately 1,100 nt was expected with all transgenic plant lines. Such a TEV CP transcript was detected in CP expressing plant lines by using a minus sense riboprobe containing the TEV CP sequence. A similar transcript was detected in AS plants by using a plus sense riboprobe containing the TEV CP sequence. The transcript in the RC line, while detected with a minus sense riboprobe, may have migrated as a slightly larger (ca 1,100–1,200 nt) RNA species, possibly due to termination at an alternately selected site and/or a longer poly-A tail on the transcript. Differing levels of CP transcript accumulation were observed among different transgenic plant lines. Transgenic plant lines expressing the coat protein of TEV were identified by western blot analysis using polyclonal antisera to TEV CP. Tissue samples of regenerated plants were ground in 10 volumes of 2× Laemmli (Tris-glicine) runner buffer (Laemmli 1970) and clarified by centrifugation in a microcentrifuge for 10 min. at 10,000×g. Protein concentration was estimated by the dye binding procedure of Bradford (1976) using BSA as a standard. Protein samples (50 µg total protein) were separated on a 12.5% polyacrylamide gel containing SDS and subjected to the immunoblot transfer procedures described by Towbin et al. (1979). Anti-TEV coat protein polyclonal primary antibodies, alkaline phosphatase conjugated secondary antibodies and the chromogenic substrates NBT (para-nitro blue tetrazolium chloride) and BCIP (5-bromo-4-chloro-3-indoyl phosphate para-toluidine salt) were used to detect bound antigen.

Coat protein products produced in FL plants were stable and accumulated to different levels in individual transgenic plant lines. It was estimated by western blot analysis that between 0.01% to 0.001% of total extracted protein was TEV CP.

1.5 Assessment of Resistance to TEV

Eight-week-old (circa 15 cm tall) R1 and R2 plants were inoculated with either purified virus preparations or infected plant sap. Inoculum was applied with sterile, pre-moistened cotton swabs. Infected plant sap inoculum was prepared by grinding TEV-infected *N. tabacum* Burley 21 leaf tissue (2 weeks postinoculation) in carborundum and 50 mM sodium phosphate buffer (pH 7.8) at a ratio of 1 gm:02 gm:10 mls, respectively, and filtering the homogenate through cheesecloth. TEV virons were purified as described by Dougherty and Hiebert (1980b). One leaf per plant was dusted lightly with carborundum (320 grit) and inoculated at two interveinal locations with 50 µl (total) of inoculum. Inoculated plants were examined daily and the appearance and severity of systemic symptoms recorded. Symptoms on any leaf above the inoculated leaf were considered to be systemic.

Figure 5A:
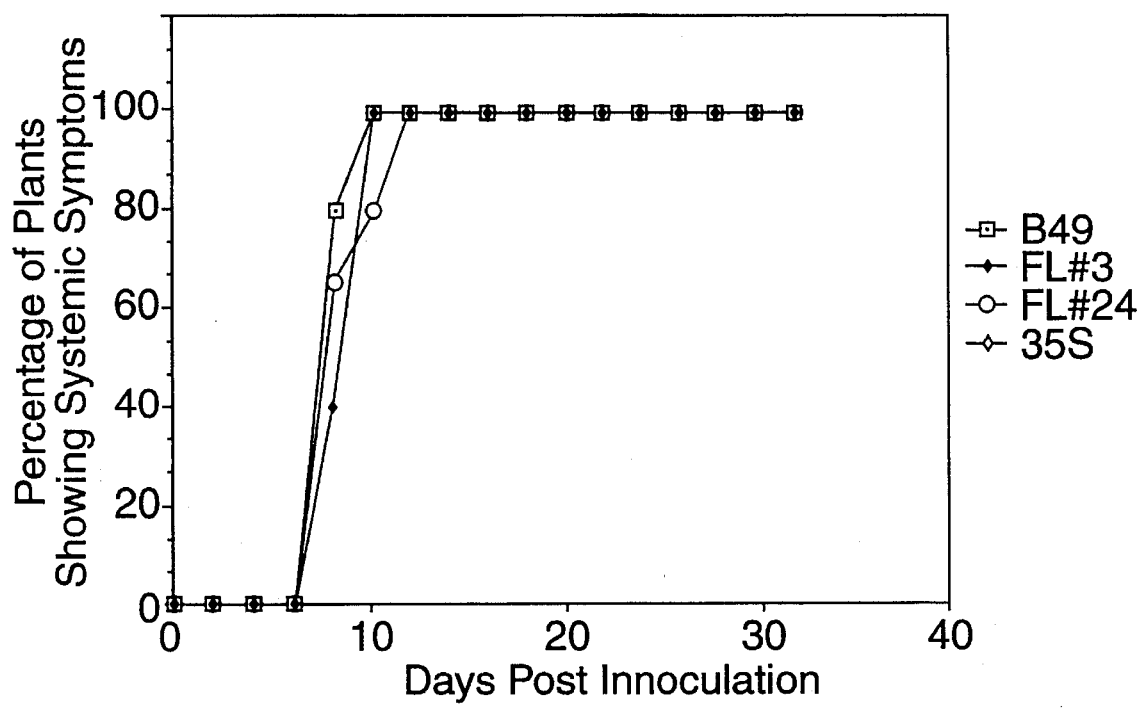

Typically, inoculation of Burley 49 plants with TEV (either purified virus or plant sap) resulted in severe chlorosis and mosaic and mottle on systemically infected leaves approximately 6–7 days after inoculation. Severe etching of the leaf followed within a few days. It was observed that transgenic plants containing only the CaMV promoter and 5' and 3' untranslated sequences (i.e., 35S plant line) responded to challenge inoculation in a manner similar to wild type Burley 49, developing extensive chlorosis and etching at the same rate (FIG. 5A). FL Plant lines which expressed TEV CP showed little or no delay in the appearance of symptoms when inoculated with infected plant sap. However, FL transgenic plants did show a slight attenuation of symptoms and eventually (2–4 weeks after initial appearance of symptoms), younger leaf tissue emerged devoid of symptoms and virus as demonstrated by back inoculation experiments. Typically chlorosis and etching on older systemic leaves was limited.

Ten independently transformed RC lines and seven independently transformed AS lines were obtained. Progeny from three of the RC lines, including line RC #7 and from one of the AS lines, including AS #3, showed an altered response to viral infection relative to control plants. All of these lines were verified to be transformed and were producing expected RNA products. A possible explanation for the variation in observed phenotype is the previously noted "position effect" whereby the expression of genes from identical DNA sequences integrated at different locations within the genome show varying patterns of tissue specificity.

Ten R2 expressing plants of the FL expressing line were inoculated with infected plant sap, and 20 R2 plants of lines AS #3 and RC #7 were inoculated with 50 µl of a 5 µg/ml solution of purified TEV. Identical results to those obtained by purified TEV inoculation were obtained when AS #3 and RC #7 R2 plants were inoculated with TEV-infected plant sap, as described above.

R2 generation transgenic AS#3 tobacco plants which were homozygous for the AS transgene showed altered symptomology when infected with TEV: small chlorotic lesions form on the leaves of these plants in a non-uniform manner. In contrast, R2 generation RC#7 plants remain asymptomatic after inoculation with TEV, and TEV has never been detected in or recovered from these plants.

Plants from TEV resistant RC lines showed no increased resistance, relative to untransformed controls, to infection by two other members of the potyvirus family, namely Tobacco Vein Mottling Virus and Potato Virus Y, or to other virus types.

1.6 Analysis of TEV Replication in Protoplasts Derived from Transgenic Plant Lines In an attempt to explain the results obtained when AS and RC transgenic plants were challenged with TEV, it was sought to determine if all of the transgenic plant lines would support virus replication at a level comparable to Burley 49. Accumulation of viral encoded proteins was used as an indirect indicator of viral replication. Protoplasts were derived from leaf tissue of homozygous CP expressing plants and electroporated according to the procedure of Luciano et al. (1987) with TEV RNA.

Protoplasts were prepared from transgenic plants and electroporated according to the procedure of Luciano et al. (1987). Protoplasts ($1\times10^6$) were resuspended in 450 µl electroporation buffer (330 mM mannitol, 1 mM $KPO_4$ pH 7.0, 150 mM KCl) and electroporated using a BTX Transfector 300 (BTX San Diego, Calif.) (950 micro Farads, 130-volt pulse amplitude, 3.5 mm electrode gap) in the presence or absence of 6 µg of purified TEV RNA. After electroporation, protoplasts were incubated for 96 hours in incubation medium as described in Luciano et al. (1987). Protoplasts were extracted in 2× Laemmli (Trisglycine) running buffer, and $5\times10^4$ extracted protoplasts were then subjected to western blot analysis as described above. Protoplast viability was measured by dye exclusion as described in Luciano et al. (1987). All electroporated protoplast samples had equivalent viability counts. The results indicated that protoplasts from all FL plant lines supported virus replication at levels comparable to wild type Burley 49 protoplasts. Transfected protoplasts derived from AS #3 plants supported TEV replication, albeit at a reduced level. Protoplasts derived from RC #5 transgenic plant leaf tissue did not support TEV replication at a detectable level. These results, and those presented in the whole plant inoculation series, suggested AS and RC plants interfere with TEV replication via different mechanisms.

1.7 Discussion of Data

This Example indicates that varying degrees of protection from TEV infection can be achieved by overexpression of coat protein and by expression of an antisense RNA. The current invention which comprises the expression of an untranslatable plus-sense RNA molecule provides protection against TEV infection that is more effective than either of these two methods. Plants of line RC #7, transformed with the disclosed DNA molecule encoding an untranslatable plus sense RNA derived from the TEV coat protein gene, were asymptomatic and appear to be completely protected from virus infection. The disclosed invention therefore represents a new and effective way of generating potyvirus resistant germplasm.

Tobacco protoplasts derived from plants expressing the antisense RNA supported a reduced level of TEV replication compared to control cells derived from untransformed plants. In contrast, tobacco protoplasts derived from plants of line RC #7, expressing the untranslatable plus sense RNA did not support detectable TEV replication. This suggests that the untranslatable plus sense RNA was more effective at blocking TEV replication in the cells of those transformed plants tested.

EXAMPLE II

Production of plants with enhanced vital resistance using 2RC constructs 2.1 Summary The foregoing example describes the production of virus resistant tobacco by transforming progenitor plants with a DNA sequence encoding an untranslatable plus sense RNA molecule derived from a single region of the TEV genome, the coat protein gene. In the experiments described below, plants were transformed with a DNA molecule encoding an untranslatable plus-sense RNA molecule derived from two regions of the TEV genome, the coat protein gene and the 5' untranslated region (UTR) of TEV. These lines are referred to as 2RC lines. These 2RC lines are shown to exhibit enhanced resistance compared with the RC lines described in the preceding example. While 30% of the RC lines were highly resistant and the remaining RC lines were susceptible, all of the 2RC lines showed some level of resistance. Resistance in these 2RC lines appears to be more effective overall; the 2RC lines displayed either a highly resistant phenotype or a "recovery" phenotype after inoculation with TEV.

Figure 6:
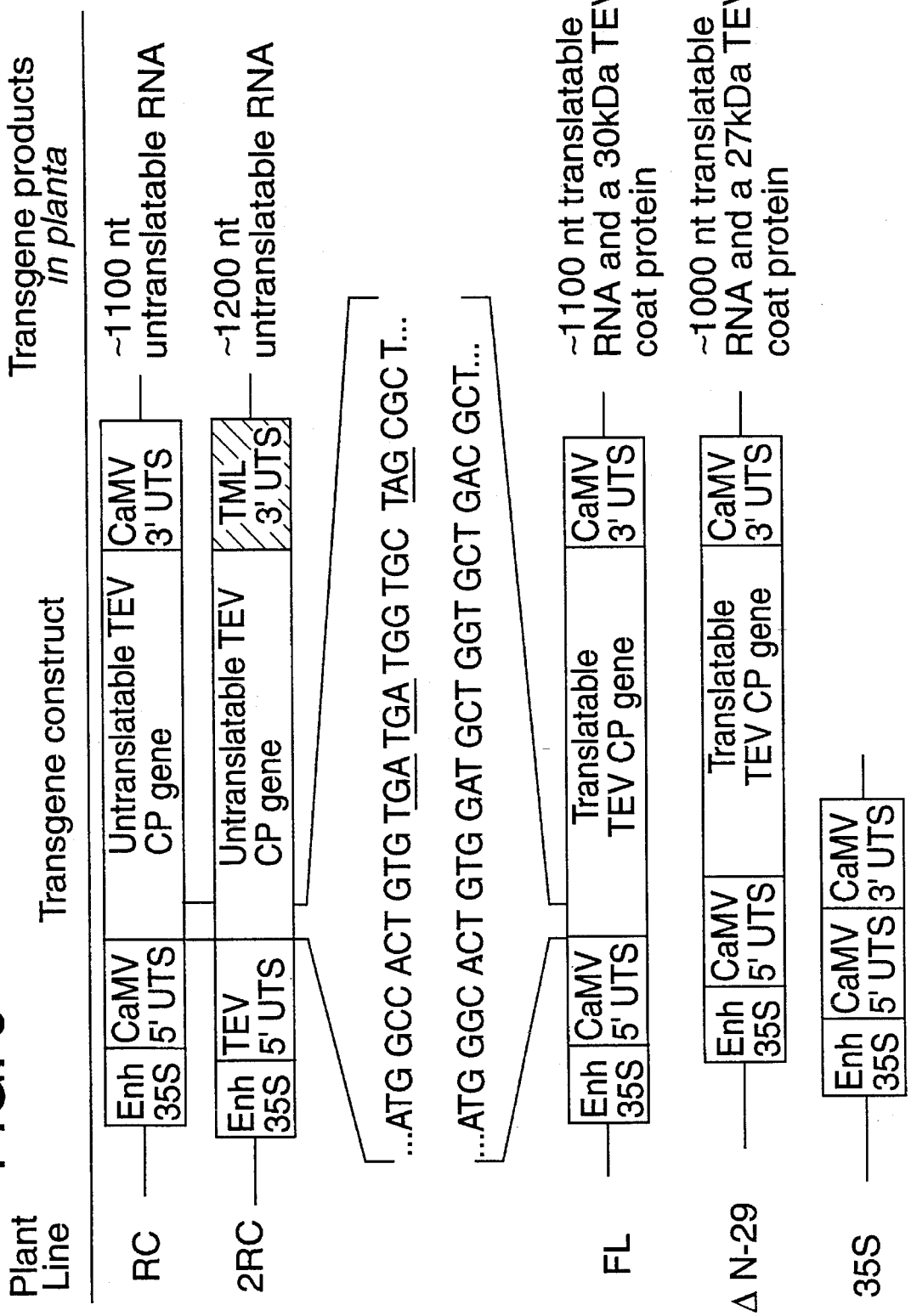

2.2 Materials and Methods Construction of DNA Molecules and Generation of Transgenic plants The DNA molecules used to produce the 2RC tobacco lines utilized the same untranslatable version of the TEV coat protein gene as described for RC constructs above. However, whereas in the RC constructs, the 5' and 3' UTRs were derived from cauliflower mosaic virus (CaMV), the 2RC constructs utilized the 5' UTR from TEV and the 3' tumor morphology large (tml) UTR from *Agrobacterium tumefaciens*. Comparisons of the RC and 2RC constructs are shown in FIGS. 4 and 6. Transgenic *Nicotiana tabacum* cv. Burley 49 (Burley 49) plants were generated by *Agrobacterium tumefaciens*-mediated leaf disc transformation procedures as described above.

Kanamycin resistance analysis

Transgenic seeds were screened for kanamycin resistance by germinating seeds on agar plates containing kanamycin sulfate (Lindbo and Dougherty 1992b). Generally 100 to 200 seeds per transgenic seed sample were analyzed.

Analysis of RNA in transgenic plants

Total RNA was isolated from transgenic plants by LiCl precipitation (Voerwood et al., 1989). Denaturing RNA gels and northern gel blotting were performed using standard techniques as described in Lindbo and Dougherty (1992a, 1992b). Northern blots were hybridized with strand specific [$^{32}$P]-labeled RNA probes generated from SP6/T7-based cell-free transcription reactions of a plasmid containing a cDNA copy of the TEV CP gene (Lindbo and Dougherty 1992a, 1992b). The amount of radioactivity in the 1200 nucleotide RNA band was estimated by densitometric analysis of exposed X-ray films with a Zeineh soft laser scanning densitometer (model SL-DNA; Biomed Instruments Inc., Fullerton, Calif.).

Analysis of Genomic DNA in transgenic plants

Plant genomic DNA was extracted as described by Rogers and Bendich (1988). Genomic DNA was digested with a restriction enzyme that cut the DNA at a single site within the transferred DNA. Southern blotting procedures were performed as described in Sambrook et al. (1989). Southern blots were probed with $\alpha$-$^{32}$P dCTP-labeled TEV CP DNA fragments. CP DNA probes were synthesized by the random prime method of Feinberg and Vogelstein (1984) using a random prime extension labeling kit (DuPont).

Plant inoculation experiments

Plants were mechanically inoculated with a 1:10 dilution of virus-infected plant sap (Lindbo and Dougherty, 1992a). Typically, the plants were observed daily for 45 days.

ELISA

A double antibody sandwich enzyme linked immunosorbent assay (DAS-ELISA) (Converse and Martin, 1990), was used to detect TEV CP in plant extracts.

Plant grafting experiments

Most grafting experiments used a cleft graft. Rootstocks were prepared by removing the shoot of the rootstock above at least two healthy basal leaves. When recovered plant tissue was used as rootstock, the shoot was removed above at least two asymptomatic (fully recovered) leaves. A vertical cut, three to four cm long, was then made in the center of the stm. Scions were prepared by removing leaves larger than 4 cm in length and trimming the base of the scion to a wedge. The cambia of stock and scion were aligned along the lengths of the cuts, secured with paraffin film (parafilm) and covered with a polyethylene base for 7 days. Rootstock or scion were typically inoculated 10 to 14 days later. In total, 152 grafted plants containing 2RC-6.13 tissue were examined in seven different studies during 1992 and 1993.

Nuclear run-off assays

Isolation of nuclei from transgenic plant tissue and in vitro labeling of run-off transcripts were as described by Cox and Goldberg (1988) except DEPC was omitted from the extraction buffer. Transcripts from nuclei of recovered or unchallenged transgenic plant tissues were labeled with $\alpha$-$^{32}$P CTP (3000 μCi/mmol). Labeled transcripts were isolated by the following modification of the protocol of Cox and Goldberg (1988): after DNase and proteinase K treatment of the in vitro labeling reaction, the reaction mix was extracted with phenol:chloroform (1:1). Transcripts were precipitated twice with 0.4 volumes of 5M ammonium acetate and 2.5 volumes of EtOH. The final pellet was resuspended in 200–300 μl ddH$_2$O. The amount of $^{32}$P-CTP incorporated per labeling reaction was estimated by precipitation of labeled RNA onto DE81 filters (Sambrook et al. 1989) and counting the sample in a liquid scintillation counter.

Labeled run-off transcripts were hybridized to specific DNA sequences bound to nitrocellulose filters. Duplicate nitrocellulose filter dot blots were prepared onto which 5 μg of linearized plasmid DNAs were spotted. Plasmid DNAs spotted contained sequences corresponding to: 1) a cDNA copy of the TEV CP gene (pRC-RC1); 2) an actin gene from Arabidopsis (pACT-4); 3) a ubiquitin gene from tomato; 4) and a cyclophilin gene from tomato. The ubiquitin and cyclophilin sequences were inserted into pUC-118 as a 250 and 480 bp PCR generated product respectively. Additionally, pUC-118 plasmid DNA was spotted. Following prehybridization (Sambrook et al., 1989), one filter was hybridized with labeled runoff transcripts from nuclei from unchallenged tissue and the other filter with labeled transcripts from nuclei of recovered transgenic plant tissue. Approximately 1 to 10×10$^6$ cpm/ml hybridization solution were used on each filter. Blots were hybridized overnight at 45°–55° C., and then washed twice in 2× SSC at room temp for 5 min, and washed two times in 0.2× SSC at 45°–50° C. for 60 min. Washed nitrocellulose filters were air-dried and exposed to Kodak X-Omat film with an intensifying screen. After autoradiography, the nitrocellulose dot blots were excised with a cork borer and the radiolabeled RNAs bound to the individual DNA samples, were quantitated in a liquid scintillation counter.

2.3 Results

Putative R1 generation transgenic plants initially were screened for transgene expression (by RNA dot blot analysis) and for kanamycin resistance (data not shown). Selected R1 generation plants were self-fertilized. R2 generation seeds were collected and screened for the kanamycin resistance phenotype. Plants from R2 seed samples which displayed 100% kanamycin resistance were selected for further study. The general growth characteristics of the transgenic 2RC lines were indistinguishable from the untransformed Burley 49 plants in greenhouse studies.

Molecular genetic analysis of 2RC lines

Total RNA was extracted and analyzed in northern gel and slot blot hybridization studies. The expected 1200 nucleotide transgene transcript was readily detected in all 2RC transgenic plants and it was apparent that steady state accumulation of transcript differed among transgenic plant lines (Table 2).

TABLE 2

Transgene copy number and expression in transgenic plants

| Plant line[a] | Transgene expression[b] pg CP RNA/μg total RNA | Estimated gene copy number[c] |
|---|---|---|
| 2RC-3.3 | 2.3 | 2 |
| 2RC-4.4 | 3.3 | 1 |
| 2RC-5.2 | 8.5 | 3 |
| 2RC-6.13 | 3.2 | 3/4 |
| 2RC-8.10 | 3.2 | 1 |
| 2RC-8.11 | 5.8 | 2/3 |
| 2RC-8.13 | 2.6 | 2/3 |
| RC-7 | 3.8 | 3 |
| Burley 49 | 0.0 | 0 |

[a]Plant line nomenclature indicates transgene being expressed. 2RC and RC lines express an untranslatable version of the TEV CP that differ in the 5' and 3' untranslated sequences (UTS). Burley 49 is the untransformed tobacco germplasm.
[b]Transgene expression level was estimated by slot blot hybridization analysis of total RNA extracts hybridized with TEV CP specific probes.
[c]Transgene copy number was determined by Southern hybridization of purified genomic DNA digested with a restriction enzyme that cuts the DNA at a single site adjacent to the TEV CP sequence. Gene copy number was estimated based on slot blot hybridization studies.

One possible explanation of the difference between transcript accumulation in the various 2RC lines is a variation in the number of copies of transgene in each line. However, this explanation was ruled out by Southern hybridization experiments—although multiple copies of the transgene were found in most of the transgenic plant lines (Table 1), there was no apparent correlation between transgene copy number and steady state accumulation of the 2RC transcript.

Response of 2RC lines to virus infection Transgenic 2RC plants were screened for virus resistance via mechanical inoculation (Table 3). Most inoculation series examined transgenic plants challenged with either TEV- or PVY-infected plant sap. After inoculation, plants were observed daily for the appearance of virus-induced symptoms. Three different TEV-resistance phenotypes were observed: (1) complete resistance and no detectable TEV, (2) the ability to 'recover' from TEV infection, or (3) the sporadic formation of large chlorotic 'blotches' on a few leaves (Table 3). All 2RC lines displayed some resistance to TEV; however, the response to TEV infection was uniform in only two transgenic lines. Line 2RC-6.13 was completely resistant to TEV and typical TEV systemic symptoms were never observed. Line 2RC-8.10 consistently recovered from TEV infection. In these plants, an apparently normal TEV infection was initially established and systemic symptoms developed. However, approximately two to five weeks after inoculation, each emerging apical leaf displayed fewer virus induced symptoms than the leaf before. In these leaves, virus infected tissue was distinctly localized to chlorotic interveinal regions of the leaf. Eventually new leaves emerged devoid of virus-induced symptoms. Infectious particles or virus-encoded proteins could not be detected by back inoculation or DAS-ELISA (data not shown) suggesting that recovered tissue was virus-free. The recovered 2RC tissue was similar to recovered tissue described for transgenic lines [FL and ΔN29] that accumulated different forms of the TEV coat protein (Lindbo et al. 1993b).

The remaining transgenic plant lines displayed a mixture of responses in spite of the observation that all displayed kan$^r$. Inoculation of lines 2RC-1.8, 2RC-3.3, and 2RC-8.13 with TEV always resulted in a high proportion of plants that were completely resistant to TEV infection. However, with line 2RC-8.13, one or two plants per experiment were consistently observed to display pronounced chlorotic 'blotches' on non-inoculated leaves. Lines 2RC-4.4, -5.2 and 2RC-8.11 predominately displayed a recovery phenotype when inoculated with TEV; however, some of the plants were susceptible while others were completely resistant to TEV infection (Table 3).

TABLE 3

Response of transgenic plants to Tobacco Etch Virus infection

| Plant line[a] | % Kan[r] | Susceptible | Recovery Phenotype | Other | Extreme Resistance |
|---|---|---|---|---|---|
| Burley 49 | 0 | 100 | | | |
| RC-7 | 100 | | | | 100 |
| 2RC-1.8 | 100 | | 25 | | 75 |
| 2RC-3.3 | 100 | 17 | | | 83 |
| 2RC-4.4 | 100 | | 97 | | 3 |
| 2RC-5.2 | 100 | | 58 | | 42 |
| 2RC-6.13 | 100 | | | | 100 |
| 2RC-8.10 | 100 | | 100 | | |
| 2RC-8.11 | 100 | 9 | 79 | | 12 |
| 2RC-8.13 | 100 | | | 6 | 94 |

[a] Plant line nomenclature is as in FIG. 4. Burley 49 is the untransformed tobacco tissue and RC and 2RC lines represent transgenic tobacco plants expressing an untranslatable form of the Tobacco Etch Virus (TEV) coat protein gene.
[b] TEV phenotype refers to the symptomatic responsees the various lines display after inoculation with TEV. The percentage of plants which showed a particular symptom is presented. The results are an average of 3 different experiments in which 10 or 20 plants were inoculated.
Susceptible: typical TEV-induced symptoms identical to symptoms on TEV-infected untransformed Burley 49 tissue.
Recovery phenotype: plant initially displayed typical systemic symptoms associated with TEV infection but 2 to 5 weeks later, newly emerging leaves displayed fewer symptoms. This trend continued until new leaf tissue was completely devoid of symptoms and virus.
Other: irregular chlorotic spots, 1 to 3 cm in diameter, appeared on uninoculated leaf tissue. There were 1 to 4 spots per leaf but not all leaves had this symptom.
Extreme resistance: generally, no symptoms were observed. In some inoculation studies numerous (>100) small chlorotic local lesions formed on a few non-inoculated leaves. These lesions were approximately 0.5 to 1.0 mm in diameter, appeared in a temporal fashion for approximately 1 week, and then could not be observed. Infectious TEV could not be detected in this tissue in back inoculation studies to *N. tabacum* Burley 21 or in ELISA.

All transgenic plant lines tested displayed wild-type sensitivities to PVY and to cucumber mosaic virus. Typical necrotic local lesions formed when the 2RC lines were inoculated with tobacco mosaic virus (data not shown).

Grafting studies

Grafting studies were performed to address three issues: the durability of the resistance, whether virus could move through the highly resistant tissue and whether a highly resistant line could induce resistance in a susceptible transgenic line (perhaps with a translocatable signal).

Scions and rootstocks of the highly resistant 2RC-6.13 transgenic line were grafted in a variety of combinations to susceptible untransformed Burley 49, RC-1.9, RC-9 (Lindbo and Dougherty 1992b), and plants which showed the recovery phenotype (RC-4.4 and FL-3.3). Inoculation of the susceptible portion of the grafted plant consistently results in TEV infection and typical symptom induction, while the 2RC-6.13 tissue remained free of TEV symptoms. This result was consistent regardless of the type of graft made. In addition to visually monitoring the plants, selected tissue was back inoculated to Burley 21 tobacco plants. Virus could be readily recovered from all tissue displaying virus symptoms, but in only one instance was virus recovered from 2RC-6.13 tissue. TEV-encoded proteins also could not be detected in DAS-ELISA analysis of any 2RC-6.13 transgenic tissue used in these grafted plant studies (data not shown). The interstem graft studies demonstrated that TEV could move through 2RC-6.13 tissue however this tissue never displayed typical TEV symptoms. Grafting transgenic scions expressing a translatable (FL-3.3) or an untranslatable (RC-4.4) version of the TEV CP RNA, both of which recover from TEV infection, or a scion expressing an untranslatable RNA (RC-1.8) that was susceptible to TEV, on 2RC-6.13 rootstock failed to convert the susceptible or recovery phenotype to the highly resistant phenotype.

Analysis of transgene RNA levels

As only an untranslatable RNA is expressed in 2RC plants, transgene steady-state RNA levels were examined in reference to the resistance phenotype. Total RNA was extracted from uninfected leaf tissue of 30 cm tall transgenic plants and quantitated in slot blot hybridization studies. No obvious correlation between 2RC RNA transcript accumulation and resistance to TEV was noted.

Steady state levels of transgene RNA transcripts were also measured in various recovered transgenic plant leaf tissue of lines 2RC-4.4 and 2RC-8.11 because they usually displayed the recovery phenotype after infection with TEV. Total RNA was extracted from TEV-recovered transgenic plant tissue and from the equivalent leaf of an unchallenged transgenic plant of the same developmental age and analyzed by northern hybridization procedures. Laser densitometer scanning of autoradiograms was used to estimate the differences in steady state transgene RNA levels. The results of this analysis revealed that steady state transgene RNA levels were reduced approximately 5 to 8 fold in TEV-recovered 2RC transgenic plant tissue.

The TEV 2RC transgenes were examined in nuclear run-on studies to determine if there was a difference in transcription rates that could account for the observed 5 to 8 fold reduction in RNA steady state levels. No differences were detected and transcription rates were the same for transgenes found in unchallenged or TEV-recovered plant leaf tissue.

2.4 Discussion

Response to eight different 2RC transgenic tobacco lines to infection by TEV were characterized. Phenotypically, most 2RC transgenic plant lines responded to TEV challenge with an extreme resistance or a recovery phenotype. Highly resistant 2RC lines generally accumulated less transgene transcript than susceptible RC lines or FL or 2RC lines that would eventually display a recovery phenotype. Transgene transcript accumulation also decreased significantly in leaf tissue displaying the recovery phenotype compared to unchallenged plant tissue of the same line. However, the reduction in the steady state level of transgene transcript did not appear to be a transcriptionally controlled event. A similar observation was with transgenic plants expressing a translatable version of the TEV coat protein (FL and ΔN-29 lines) and showing the recovery phenotype (data not shown). Therefore, low or decreasing steady state levels of transgene transcript appear to correlate with resistance to TEV.

2.5 Possible Mechanism

One possible mechanism for the ability of untranslatable plus sense RNA to inhibit viral multiplication is an association of the untranslatable plus sense RNA molecule with the minus sense TEV RNA replicative intermediate, producing inhibition of viral replication. However, the biochemical analysis of transgene expression during recovery and the unlikely prospect that two RNA molecules, a 1200 nucleotide 2RC plus sense transcript and the 10,000 nucleotide TEV minus sense genomic RNA would hybridize with each other would not appear to support such a mechanism.

While not wishing to be bound by speculation, it is suggested that the highly resistant and recovery phenotypes of the 2RC lines can be accommodated by the following working model. This model suggests the existence of an inducible, cytoplasmic-based, cellular activity that degrades specific RNA sequences. In transgenic plants displaying the recovery phenotype, this RNA degradation system is activated only after virus infection and by the additive level of transgene RNA and viral RNA present. In contrast, the highly resistant lines may have the activity fully induced by the transgene transcript. The failure of a rootstock from a highly resistant line to induce a scion from a susceptible line in grafting studies suggests the activity is a programmed cell response not induced via a diffusible signaling molecule as is the case with systemically acquired resistance (Kuc 1982; Ward et al., 1991). Once the antiviral system is activated, it is absolute in its efficacy against TEV, yet it is not effective against the closely related virus PVY.

The proposed mechanism described above may be common to most eukaryotic cells. Exploitation of this cellular process may thus be an effective way to program cells to eliminate or diminish the level of particular RNA molecules in the cell. These RNA molecules may be exogenous or viral in nature and, as demonstrated, exploitation of this system is an effective way to generate virus resistant plants. Alternatively, endogenous or cellular RNA molecules may also be targeted and activation of this RNA degradation system may be an effective way to generate plants defective in a particular phenotype.

EXAMPLE III

Field assessment of virus resistant plants 3.1 Summary

*Nicotiana tabacum* cv. Burley 49 germplasm, transformed with various mutated versions of the tobacco etch virus (TEV) coat protein gene, was tested under field conditions for tolerance and/or resistance to TEV. A total of 24 independent transgenic lines and eight different mutated versions of the TEV CP gene were examined. The test was conducted at the same field location for two successive years. Transgenic plants expressing a mRNA which was translated into a full length TEV coat protein became infected when challenged with TEV but 3 to 4 weeks later recovered from TEV infection. The same response was displayed by plants containing a gene lacking the codons for the amino terminal 29 amino acids of the TEV coat protein. Plants containing a gene which expressed an antisense RNA version of the TEV coat protein sequence displayed little tolerance to TEV. A similar response to TEV was noted with plants containing only gene regulatory sequences and no TEV-derived sequences, or plants with no foreign gene sequences at all (Burley 49). Selected plants expressing untranslatable versions of the TEV coat protein mRNA never became infected with TEV and displayed a very high level of resistance. This confirms the efficacy of untranslatable plus-sense RNA in conferring virus resistance under field conditions.

3.2 Materials and Methods

Transgenic plant germplasm

*Nicotiana tabacum* cv. Burley 49 was selected for transformation because of the severe reaction this germplasm displays when inoculated with TEV. The construction of the transgenes, transformation procedures and other characteristics of these transgenic lines have been described above and are also set forth in Lindbo and Dougherty (1992) which is herein incorporated by reference. The various transgenes (and their nomenclature) expressed in plants examined in this field study are described in FIG. 4.

Field plot design

In 1992, seeds of 16 different entries were sown on a commercial potting mix. When plants reached a height of 5 to 8 cm, they were transferred to styrofoam trays in a greenhouse float system and grown to transplanting size. Prior to transplanting, each entry was inoculated (as described below) with a local isolate of TEV. Plants were transplanted with a commercial transplanter cm apart in rows that were 125 cm apart. Each sub-plot consisted of 10 plants.

A split plot design, with time of inoculation being the main plots and entries being the sub-plots, was used with four replications in a complete block arrangement. There were three main plots consisting of inoculation at transplanting, inoculation when plants were 40 cm high, and a control or no inoculation. In 1993, a similar design was followed with two exceptions: 24 entries were examined and the inoculation when plants were 40 cm high was omitted. Since TEV spread to uninoculated plants quickly and uniformly, inoculation when plants were 40 cm in height was not necessary.

Inoculum preparation and procedure

The TEV isolate used was obtained from tobacco grown in a commercial Florida field. Inoculum was prepared using systemically infected leaves from Burley 21 plants. Infected leaves were homogenized in 0.1M borate buffer (pH 7.6) (1 g tissue/2 ml of buffer) and the homogenate clarified by expressing through cheesecloth. One gram of 600 mesh carborundum was added to each 100 ml of inoculum and was stored in a polyethylene bottle in an ice bath and used within 24 h of preparation. Inoculations were made at transplanting by water soaking a small area on two leaves per plant with inoculum. Inoculum soaking was effected with a Thayer and Chandler Model E airbrush was a 500 ml reservoir. Inoculum was propelled using carbon dioxide at a pressure of 60 pounds per square inch. A young leaf, 8–10 cm in length, near the top of the plant and the next oldest leaf were inoculated on each plant. The inoculated area of each leaf was about 2 cm from the tip of the leaf on the abaxial surface of the leaf and centered over the mid-vein. The orifice to leaf distance of the airbrush was about 1 cm, and resulted in rapid water soaking of an area of about 1.5 cm in diameter.

Plant Evaluation

The tobacco was grown using standard cultural practices for Burley tobacco. Pesticides applied broadcast and preplant incorporated included the herbicides, pendimethalin and pebulate, the insecticide, chlorpyrifos, and the fungicide, metalaxyl. The fumigant nematicide, dichloropropene, was injected in the row at bedding in 1992 and was broadcast by the plow-down method in 1993. Also in 1993, the nematicide, fenamiphos, was applied as a preplant incorporated treatment. The two nematicides were used because nematodes were expected to be at a high population, and increasing the rate of the fumigant nematicide would increase the risk of phytotoxicity. The insecticide acephate was included in the transplant water. The only foliar-applied pesticide was acephate and it was applied as needed. All pesticides were applied at labeled rates. A 6-6-18 fertilizer was applied in three or four applications. Irrigation was applied as needed by overhead sprinklers.

Plants were visually monitored for symptoms associated with TEV infection. Additionally, double diffusion immunoassays (Gooding et al., 1970; Purcifull and Batchelor, 1977) and inclusion body analyses (Christie and Edwardson, 1977) were performed on the test entries. Plant morphology was also noted, and near the end of each growing season, green weight was obtained from three representative plants from each plot. Each of the three plants were serologically assayed enzyme-linked immunosorbent assay (ELISA) for TEV and PVY. Of the seven plants remaining after mass determination, four were examined four weeks later for root diseases that may have affected above ground weight determination. Although some root galling was observed, it occurred on all entries and was not believed to be of sufficient severity to affect plant growth prior to weight determinations.

3.3 Results
Description and plant evaluation of entries

Sixteen different entries was assessed in 1992. Plant growth and morphology correlated with the transgene expressed. Transgenic plants expressing either a ΔC118 version of the TEV coat protein were stunted slightly, and the leaves were typical of Burley tobacco. Transgenic plants expressing the RC or 2RC untranslatable version of the TEV coat protein gene generally possessed a morphology typical of a Burley tobacco plant. Other lines could not be evaluated for plant type as virus infection resulted in severe stunting.

Assessment of virus resistance

Different transgenic lines responded to virus infection in a line-specific manner. The formation of symptoms and the presence of a suspected viral infection was confirmed by cytoplasmic inclusion analysis or by using virus-specific polyclonal antibodies in ELISA. The results are summarized in Table 4.

TABLE 4

| | Plant response to injection with tobacco etch virus (TEV) | | |
|---|---|---|---|
| Entry[1] | Average Symptom Intensity[2] | Average Stunting[3] | Recovered Plant Phenotype[4] |
| Burley 49 | 4 | 4 | No |
| 35S-4.7 | 4 | 4 | No |
| F1-3.3 | 3—>0 | 1 | Yes |
| F1-24.3 | 3—>0 | 1 | Yes |
| ΔN-2.12 | 3—>0 | 1 | Yes |
| ΔN-8.1 | 3—>0 | 1 | Yes |
| ΔC-7.9 | 2 | 2 | No |
| ΔC-15.7 | 2 | 2 | No |
| ΔN/ΔC-6.9 | 2 | 2 | No |
| ΔN/ΔC-6.14 | 3 | 2 | No |
| ΔC118-18.1 | 0 | 0 | N/A |
| AS-6.1 | 4 | 4 | No |

TABLE 4-continued

| | Plant response to injection with tobacco etch virus (TEV) | | |
|---|---|---|---|
| Entry[1] | Average Symptom Intensity[2] | Average Stunting[3] | Recovered Plant Phenotype[4] |
| AS-7.2 | 4 | 4 | No |
| RC-5.02 | 0 | 0 | N/A |
| RC-7.16 | 0 | 0 | N/A |
| RC-9.1 | 4 | 4 | No |
| 2RC-6.13 | 0 | 0 | N/A |
| 2RC-1.8 | 0 | 0 | N/A |
| 2RC-3.3 | 2—>0 | 0 | Yes |
| 2RC-5.2 | 2—>0 | 0 | Yes |
| 2RC-8.13 | 2—>0 | 0 | Yes |

[1]Plant Entries and their nomenclature are described in FIG. 1. Number after line identification (i.e., 4.7 of 35S-4.7) indicates a particular line derived from a single transformed parent plant.
[2]Average symptom intensity was a subjective analysis of TEV-induced symptoms. The rating scale was from 0 to 4. 0 = no symptoms, 1 = mild chlorosis and mosaic, 2 = moderate mosaic, 3 = severe mosaic and some chlorosis and etching of leaves, 4 = severe chlorosis and etching of leaves. For plants that displayed the recovered phenotype, ratings are given for initial and final symptoms (i.e., 3—>0).
[3]Average stunting was an estimate of how TEV infection impacted plant growth. The rating scale was from 0 to 4 with 0 being no obvious stunting and 4 being severe stunting typical of TEV infection of N. tabacum cv. Burley 49.
[4]Some of the transgenic lines displayed a recovery phenotype in which the plant was able to 'outgrow' the infection. Older leaves displayed TEV-induced symptoms while younger leaves possessed no symptoms and virus. N/A, not applicable.

In general, four different plant responses were noted among the different transgenic lines. Selected entries became infected with TEV and displayed severe symptoms. Plants were stunted and showed significant etching (necrosis) and extreme chlorosis. All plants of the following entries displayed this response: Burley 49, 35S line, AS lines, and a selected RC line (RC-9.1). A second phenotype observed in selected lines following TEV infection was characterized by attenuated systemic symptoms, often in the form of localized chlorotic spots on the leaves. Transgenic lines ΔN/ΔC and ΔC18 displayed this attenuated symptom phenotype. The third generalized type of symptomatology was exhibited by all TEV-infected FL- and ΔN29-lines and by selected 2RC lines. These transgenic plants initially became infected and displayed typical TEV-induced symptoms; however, the plant gradually recovered from the infection. As new leaves emerged, symptoms were restricted to the interveinal areas. Subsequent leaves possessed less symptomatic tissue until finally leaves developed totally devoid of symptoms and virus. Once these plants recovered from TEV infection, the upper leaf tissue was virus and symptom-free and never became re-infected with TEV. A fourth response to TEV infection was displayed by selected RC and 2RC lines and on ΔC118 line. These plants never displayed any symptoms after infection with TEV via initial mechanical inoculation or subsequent aphid transmission.

The engineered resistance was TEV specific. None of the lines tested displayed any resistance to PVY or tomato spotted wilt virus (TSWV) as a limited number of plants were naturally infected with these viruses in the plot over the 2 year study.

In addition to mechanically transmitted TEV, the test plot was assessed for virus resistance against aphid-vectored TEV (Reagan et al., 1979). No colonizing aphid populations were detected, yet 100% of the uninoculated Burley 49 and susceptible transgenic plants became infected 2–3 weeks after transplanting. Virus movement was likely due to high migratory aphid populations during both years of the study. Under these conditions, the TEV-resistant RC and 2RC lines remained free of TEV.

Green weight of representative plants was also determined as an estimate of virus resistance. In 1992, these measurements were taken when ca. 75% of the plants were in flower. This was 2 weeks after the highly resistant RC and 2RC lines had flowered. In 1993, green weight measurements were taken when 10% of the plants were flowering. Only plots mechanically inoculated with TEV were assayed. Seven to 10-fold differences in average green weight were readily apparent between protected lines and untransformed Burley 49 tissue. The results are presented in Table 5.

TABLE 5

Average green weight of plants inoculated with TEV

| Entry[1] | Average green weight (grams/plant)[2] | |
| --- | --- | --- |
|  | 1992 | 1993 |
| Burley 49 | 286 | 121 |
| 35S-4.7 | 140 | 91 |
| F1-3.3 | 1893 | — |
| F1-24.3 | 1636 | — |
| ΔN-2.12 | 1944 | — |
| ΔN-8.1 | 1598 | — |
| ΔC-7.9 | 2094 | — |
| ΔC-15.7 | 1958 | — |
| ΔN/ΔC-6.9 | 1640 | — |
| ΔN/ΔC-6.14 | 1682 | — |
| ΔC118-18.1 | — | 1329 |
| AS-6.1 | 761 | — |
| AS-7.2 | 874 | — |
| RC-5.02 | 1648 | 1206 |
| RC-7.16 | 1639 | 1303 |
| RC-9.1 | 438 | 110 |
| 2RC-6.13 | 1487 | 1123 |
| 2RC-1.8 | — | 1382 |
| 2RC-3.3 | — | 1321 |
| 2RC-5.2 | — | 1121 |
| 2RC-8.13 | — | 848 |

[1]Plant entry and nomenclature is described in FIG. 4.
[2]Three representative plants from each plot were harvested and weighed. The plot was replicated four times and the average green weight for these four replicas is presented. In 1992, green weight was taken after most plants had flowered. The RC and 2RC plants flowered 2 to 3 weeks earlier, presumable because they were free from TEV the entire growing season. Therefore, their green weights are probably lower than the maximum weight achieved. In 1993, green weight measurements were taken as plants began to flower.

3.4 Discussion

Results from this field study demonstrate that genetically engineered resistance produced by expressions of plus-sense untranslatable RNA molecules homologous to the TEV coat protein gene can be effective at preventing losses incurred by TEV infection. Resistance to TEV was manifested in a variety of phenotypes. Lines producing an untranslatable version of the TEV coat protein gene (RC and 2RC lines) afforded superior protection. Many of these selected lines never became infected in the 2 year field trial. This was remarkable in view of the inoculum potential provided by endemic TEV and migratory aphid populations. All uninoculated control Burley 49 plants became infected 2 to 3 weeks after transplanting. Therefore, the highly resistant RC and 2RC lines withstood mechanical inoculation and severe aphid-vectored TEV pressure. Transgenic lines expressing these transgenes resulted in green weight difference that were, on average, 10 fold higher than susceptible Burley 49 tissue (Table 5).

Another form of resistance manifested itself in a recovering plant phenotype. ΔN29, FL and selected 2RC plant lines initially became infected with TEV but recovered. Newly emerging leaves were free from TEV and TEV-induced symptoms. Of particular interest was the observation that these plants never became re-infected with TEV during the reminder of the field test. These plants may therefore also offer a useful form of resistance.

Transgenic plants expressing ΔN/ΔC and ΔC18 forms of the TEV coat protein also displayed resistance to TEV infection although it was inferior to resistance described above and permitted a mild systemic infection. The results also showed that the 35S and AS transgenic plants did not provide a useful form of resistance to TEV.

The second major conclusion from this study was that the expression of particular transgenes affects plant type. A recent study by Brandle and Miki (1993) showed that transformed tobacco plants may have altered agronomic characteristics. In the present study, a dwarfed appearance was consistently associated with all plants expressing a ΔC18 or ΔN/ΔC transgene. This phenotype was observed regardless of transgene expression levels and suggests the transgene transcript or protein product was responsible for the altered plant morphology. Plants expressing an untranslatable RNA and displaying superior resistance (selected RC and 2RC) had good Burley plant characteristics. These transgenes and their products did not appear to impact Burley growth characteristics.

In summary, extremely effective virus resistance in the field can be generated using the untranslatable plus-sense RNA technique of the present invention. This technique is superior to existing genetic engineering approaches to virus resistance for a number of reasons. The virus resistance produced was superior in untranslatable plus-sense RNA lines; TEV was not detected in these lines over the 2 year study. Second, expression of the untranslatable plus-sense RNA transgenes did not obviously affect Burley plant type. Third, expression of a gene in the form of an untranslatable RNA molecule may address relevant concerns regarding the potential widespread application of PDR practice (de Zoeten, 1991; it has been suggested that transencapsidation of viral RNAs by transgene products may generate virions with expanded host range or new insect vector association). Transencapsidation occurs naturally and recently has been shown to occur in transgenic plants (Farinelli et al., 1992). Additionally, RNA recombination between viral genomes and transgene transcripts might increase the possibility of generating new viral entities. Transgenes which express untranslatable RNAs should minimize or essentially negate these concerns.

EXAMPLE IV

Studies with other virus types

The preceding Examples describe the use of untranslatable plus sense RNA to engineer resistance in plants to Tobacco Etch Virus, a member of the potyvirus family. Additional studies demonstrate that the present invention is applicable to produce plants resistant to other members of the potyvirus family as well as viruses outside of this family.

4.1 Production of Tobacco Plants Resistant to Potato Virus Y

Potato virus Y (PVY) is, like TEV, a member of the potyvirus family. Using a strategy similar to that described in Examples I and II above, two different varieties of tobacco (*N. tabacum* cv tabacum K149 and K326) were transformed with untranslatable versions of the PVY coat protein gene. The tobacco varieties are distinct from the *N. tabacum* cv Burley 49 used in the TEV studies described above. The transgene constructs are analogous to the TEV transgene constructs and are shown in schematic form in FIG. 7.

Preliminary data indicates that tobacco plants transformed with constructs encoding untranslatable plus sense RNA molecules homologous to the PVY coat protein are highly resistant to PVY infection. Table 6 below summarizes the results obtained to date. Three different PVY isolates were used to determine virus resistance. These three isolates ranged in their pathogenicity from the induction of mild mosaics to a necrotic reaction and plant death. Highly resistant lines were resistant to all isolates.

TABLE 6

| PVY Transgenic Tobacco Plant Summary | | | | | |
|---|---|---|---|---|---|
| | | | Response to challenge with PVY | | |
| Germplasm[a] Designation | Gene[b] Construct | Total number | Highly Resistant | Resistant | Susceptible |
| *N. tabacum* cv K149 | | | | | |
| Y-149-35S-XX | 35S | 3 | — | — | 3 |
| Y-149-AS-XX | AS | 6 | — | — | 6 |
| Y-149-CP-XX | CP | 18 | 3 | — | 5 |
| Y-149-RC1-XX | RC-1 | 17 | 11 | 2 | 4 |
| *N. tabacum* cv K326 | | | | | |
| Y-326-35S-XX | 35S | 6 | — | — | 6 |
| Y-326-AS-XX | AS | 15 | — | — | 15 |
| Y-326-CP-XX | CP | 19 | 1 | 2 | 5 |
| Y-326-RC1-XX | RC-1 | 41 | 10 | 3 | 18 |

[a]Two different tobacco varieties were used in this study. K326 and K149 are commercial flue-cured cultivars. The transgenic plant line designation is presented below each cultivar name. The line nomenclature (e.g., Y-149-35S-XX) indicates the virus the transgene is derived from [Y = PVY], the cultivar transformed [149 = *N. tabacum* cv K149], the transgene [35S = transgene regulatory sequences derived from the 35S RNA of cauliflower mosaic virus, and the individual line number [XX = 1, 2, etc.]
[b]Four different gene constructs were introduced into the various tobacco cultivars. A schematic drawing of the four gene constructs and their designation is presented i FIG. 7. 35S, transgene that contains a cauliflower mosaic virus transcriptional promoter and 5' and 3' untranslated regions of the 35S RAN; AS, antisense version of the potato virus Y (PVY) coat protein open reading frame; CP, a translatable version of the PVY coat protein ORF; RC-1, an untranslatable plus-sense version of the PVY coat protein ORF.

Studies from other laboratories have also shown that untranslatable plus sense RNA molecules are effective at preventing PVY infection in tobacco. For example, van der Vlugt et al. (1992) have shown that a coat protein plus sense RNA molecule lacking the AUG translation initiation codon (and therefore rendering the molecule untranslatable) is effective at preventing PVY infection in tobacco.

4.2 Production of Plants With Enhanced Resistance to Tomato Spotted Wilt Virus (TSWV)

The efficacy of the present invention beyond the potyvirus family has been independently demonstrated by de Haan et al. (1992) and Pang et al. (1993). Tomato spotted wilt virus (TSWV) is the type species of the genus Tospovirus within the arthropod borne Bunyaviridae. Haan et el. (1992), herein incorporated by reference, teaches that TSWV infection in tobacco can be prevented by expression of an untranslatable plus sense form of the TSWV N gene. Haan et al. manipulated the N gene from TSWV by distorting the ATG start codon and introducing frameshift mutations. Pang et al. (1993) have described similar results with TSWV.

EXAMPLE V

Studies in other plant types

The above Examples discuss the production of virus resistant tobacco plants. As will be apparent to one skilled in the art, application of the present invention is not limited to tobacco plants but rather may be used to suppress gene expression in other plant types, to produce desired results, including virus resistance. Set forth below is a description of preliminary data obtained with potato plants.

5.1 production of PVY Resistant Tobacco Plants

The constructs described in Example IV above for producing PVY resistant tobacco plants were introduced into two different varieties of potato (Russet Norkotah and Russet Burbank). These potato plants were transformed using protocol described by De Bloc (1988). Table 7 below summarizes the preliminary results obtained when transgenic potato lines were challenged with PVY.

TABLE 7

| PVY Transgenic Potato Plant Summary | | | | | |
|---|---|---|---|---|---|
| Transgene | Total Number of Transgenics | Number Screened | Highly Resistant | Resistant | Susceptible |
| | | Russet Burbank | | | |
| FL | 22 | 22 | 5 | — | 17 |
| RC-1 | 1 | 1 | — | — | 1 |
| RC-4 | 23 | 23 | 8 | — | 15 |
| AS | 17 | 17 | 0 | 2 | 15 |
| 35S | 6 | 6 | 0 | — | 6 |

TABLE 7-continued

| PVY Transgenic Potato Plant Summary | | | | | |
|---|---|---|---|---|---|
| Transgene | Total Number of Transgenics | Number Screened | Highly Resistant | Resistant | Susceptible |
| | | Russet Norkotah | | | |
| FL | 30 | 30 | 14 | 2 | 14 |
| RC-1 | 11 | 11 | 3 | 1 | 7 |
| RC-4 | 41 | 41 | 10 | 0 | 31 |
| AS | 31 | 31 | 0 | 1 | 30 |
| 35S | 11 | 11 | — | — | 11 |

EXAMPLE VI

Production of Plants With Multiple Virus Resistance

The foregoing Examples illustrate the efficacy of the present invention in producing plants with a reduced susceptibility to infection by a single virus type. However, resistance to multiple virus types may be produced in a single plant using the invention. For example, a DNA construct encoding two or more untranslatable plus sense RNA molecules, homologous to target genes of two or more viruses may be employed.

Alternatively, resistance to multiple virus types may be conferred by the introduction of DNA molecule encoding a single untranslatable plus sense RNA molecule, provided that the untranslatable plus sense RNA was sufficiently homologous to target genes in multiple virus types. This approach may be particularly effective where the target gene is highly conserved between virus types, such as a replicase gene.

Hence, if plants were transformed with a gene encoding an untranslatable plus sense RNA derived from a gene which was highly conserved between viruses of the potyvirus family, the plants would be protected from infection by a wide range of potyviruses. Regions of the potyvirus genome which are sufficiently conserved between potyvirus types to be potentially useful in such an approach may be readily determined by one skilled in the art. Highly conserved regions may be determined by reference to published sequence data (Allison et al. 1986; Robaglia et al. 1989; Domier et al. 1986; Lain et al. 1989; Maiss et al. 1989). The efficacy of the identified regions in this approach could be readily determined using the methodologies described above and substituting an untranslatable form of the identified region for the TEV coat protein gene in the vectors described. Regions of the potyvirus genome potentially suitable include, but are not limited to the genes encoding the viral replicase and the viral proteinase.

According to the proposed mechanism for this invention, a RNA sequence specific cellular activity or system may be induced by high levels of RNA within the cell; this activity or system would be induced by the presence of both the target virus RNA and the untranslatable plus sense RNA homologous to the virus RNA. If the inducible activity is induced by the presence of specific short RNA sequences ("RNA recognition sequences") in the target RNA, it may be possible to suppress multiple target genes by incorporating multiple RNA recognition sequences into a single untranslatable plus sense RNA molecule, encoded by a single DNA molecule.

EXAMPLE VII

Comparison with antisense technology

By way of comparison with other molecular techniques that may be used to suppress gene expression, it is noted that the method of using untranslatable plus-sense RNA is conceptually distinct from the use of antisense RNA.

Because the above examples relate to the use of untranslatable plus sense RNA to suppress the expression of genes of RNA viruses, the following discussion addresses the differences between untranslatable plus sense RNA and antisense RNA in that context. RNA viruses are comprised of single-stranded (ss) or double-stranded (ds) RNA. Single-stranded viruses are designated as plus (or positive) sense or as minus (or negative) sense.

In a plus sense virus, the nucleotides that comprise the encapsidated genomic RNA are arranged in such a manner that the viral RNA resembles a eukaryotic messenger RNA (mRNA). That is, ribosomes can directly associate with the viral RNA and translate that portion of the nucleotide sequence, arranged as an open reading frame (ORF), into a protein.

The genomic RNA of a virus in which the minus strand RNA is encapsidated cannot directly serve as a mRNA. Instead, this minus strand genomic RNA must be transcribed by a viral RNA-dependent RNA polymerass to form the complementary (in this case, a plus sense) RNA. This plus sense RNA then serves as mRNA and proteins are produced by translation of this RNA.

A dsRNA containing virus encapsidates positive and negative strands that have complexed together to generate the double strand genome structure. Reoviruses are examples of double strand RNA viruses. TEV and PVY are plus sense single stranded RNA viruses. Rhabdoviruses are minus sense RNA viruses.

The transgenes that are described above can be divided into two general types based on the type of RNA transcribed from the gene. The transgenes designated FL, RC or 2RC are transcribed by the host DNA-dependent, RNA-polymerase II into plus sense RNAs and produce RNAs that have a nucleotide sequence essentially identical to the virus genomic RNA. In the case of FL transcripts, the RNA can be translated by ribosomes into a protein. RC and 2RC transcripts are nearly identical to the sequence of the FL transcripts but, the presence of the premature translation termination codons immediately after the translation initiation codon renders the RC and 2RC transcripts untranslatable. That is, ribosomes bind to these RNAs but fall off immediately when the stop codons are encountered. Hence, RC and 2RC transcripts are referred to as untranslatable plus sense RNAs.

The above examples also describe experiments using antisense (AS) RNA. Antisense RNA is transcribed into an RNA which is complementary to the RNA sequence contained in the viral genome. The AS RNA is therefore a minus sense ENA and does not contain an open reading frame that could code for a protein (i.e., it is untranslatable antisense RA as opposed to untranslatable plus sense RNA).

In some instances, antisense RNA has been shown to hybridize to complementary RNA molecules, forming a double-stranded RNA and rendering the complementary RNA molecule (usually a messenger RNA molecule) biologically inactive. However, most, if not all, examples of expressing an antisense RNA to arrest (by hybridization) the replication and expression of plus sense RNA viruses have been unsuccessful.

The difference between sense RNA (as used in the untranslatable plus sense RNA in the present invention) and antisense RNA is summarized in FIGS. 8A and 8B. In both FIGS. 8A and 8B, genomic sense RNA (the viral genome) is shown as the top line. Below that is shown a partial sequence of a corresponding sense (FIG. 8A) or antisense (FIG. 8B) RNA molecule. As illustrated in FIG. 8A, the sense RNA contains the identical nucleotide sequence as that part of the viral genomic RNA from which the sequence is derived. Therefore, hybridization between the sense RNA and the genomic RNA cannot occur. However, as shown in FIG. 8B, the antisense RNA comprises a nucleotide sequence that is complementary to the genomic RNA from which it is derived. Accordingly, hybridization between the genomic sense RNA and the antisense RNA can occur.

FIG. 8 illustrates the primary difference between antisense RNA and untranslatable plus sense RNA.

Figure 5B:
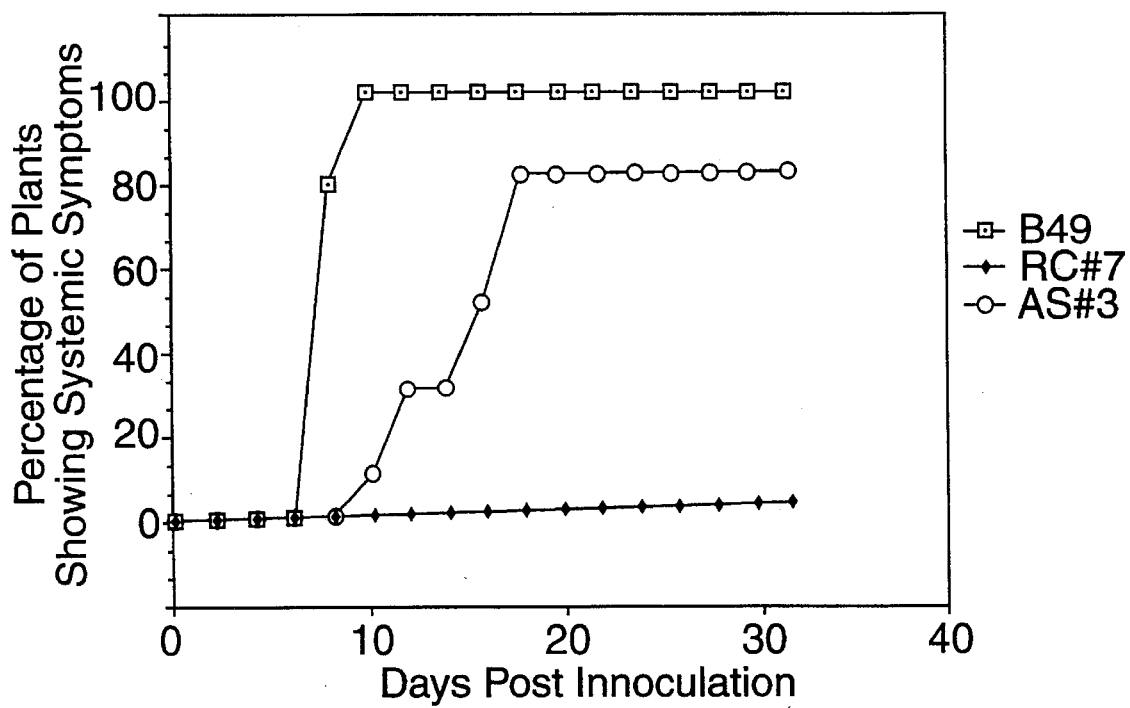

Finally, it is noted that U.S. Pat. No. 5,283,184 describes a method for suppressing the expression of genes endogenous to plants. Virus genes are not endogenous to plants, and it is not known if the method described in the '184 patent could be used to produce virus resistant plants. However, certain methods described in the '184 patent appear similar to experiments described herein with full length (FL) coat protein genes. As described in Example I herein and depicted in FIG. 5, plants transformed with full length coat protein transgenes FL #3 and FL #24 were initially as sensitive as control plants to virus. In contrast, plants transformed with untranslatable plus-sense forms of the FL gene, according to the methods of the present invention, were highly resistant to the virus.

The invention has been described in detail with particular reference to the above embodiments. It will be understood, however, that variations and modifications can be effected within the spirit and scope of the invention.

BIBLIOGRAPHY

Allison et al. 1985a. *Virology* 147:309–316.
Allison et al. 1985b. *Proc. Natl. Acad. Sci. U.S.A.* 82:3969–3972.
Allison et al. 1986. *Virology* 154:9–20.
Ausubel et al. 1992. *Short Protocols in Molecular Biology* (2d. Ed.) John Wiley & Sons.
Bevan 1984. *Nucl. Acids Res.* 12:8711–8721.
Bradford 1976. *Nucl. Acids Res.* 12:8711–8721.
Brandle and Miki, 1993. *Crop Sci.* 33:847–852.
Carrington and Dougherty 1987. *J. Virol.* 61:2540–2548.
Carrington et al. 1987. *Nucl. Acids Res.* 15:10066.
Christie and Edwardson, 1977. *Flor. Agric. Exp. Stat. Mono.* 9: 150.
Converse and Martin, 1990. Elisa methods for plant viruses. In "Serological Methods for detection and identification of viral and bacterial plant pathogens"(Hampton, R., Ball, E., and De Boer, S., Eds.) pp. 179–196 APS Press, St. Paul, Minn.
Cox and Goldberg, 1988. Analysis of plant gene expression. In "Plant molecular biology, a practical approach" (Shaw, C. H., Ed.) pp. 1–35. IRL Press, Washington, D.C.
de Block, 1988. *Theor. Appl. Genet.* 76:767–774.
de Haan et al. 1992. *Bio/Technoloy* 10:1133–1137.
de Zoeten, 1991. *Phytopathology* 81:585–586.
Ditta et al. 1980. *Proc. Natl. Acad. Sci. U.S.A.* 77:7347–7351.
Domier et al. 1986. *Nucl. Acids Res.* 14:5417–5430.
Dougherty and Hiebert 1980a. *Virology* 101:466–474.
Dougherty and Hiebert 1980b. *Virology* 104:183–194.
Farinelli et al., 1992. *Bio/Technology* 10:1020–1025.
Feinberg and Vogelstein, 1984. *Anal. Biochem.* 37:266–267.
Gluzman (1981). *Cell* 23:175–182.
Goldbach 1987. *Microbial Sci.* 4:197–205.
Gooding and Bing, 1970. *Phytopathology* 60:1293.
Groger et al. (1989). *Gene* 81:285–294.
Hanahan and Meselson 1980. *Gene* 10:63–67.
Herrera-Estrella et al. 1983. *Nature* (London) 303:209–213.
Hollings and Brunt 1981. *Commonwealth Mycological Institute/Association of Applied Biologists Descrip. Plant Viruses*, No. 245.
Horsch et al. 1985. *Science* 227:1229–1231.
Kado and Agrawai 1972. *Principles and Techniques in Plant Virology*.
Kay et al. 1987. *Science* 236:1299–1302.
Klein et al. (1987). *Nature* 327:70.
Kozak 1984. *Nature* (London) 308:241–246.
Kurtz and Nicodemus 1981. *Gene* 13:145–152.
Kuc, 1982. *BioScience* 32:854–860.
Laemmli 1970. *Nature* (London) 227:680–685.
Lain et al. 1989. *Virus Res.* 13:157–172.
Lawson et al. 1990. *Bio/Technoloy* 8:127–134.
Lindbo and Dougherty, 1992a. *Mol. Plant-Microbe Interact* 5:144–153.
Lindbo and Dougherty, 1992b. *Virology* 189:725–733.
Lindbo, et al. 1993b. *The Plant Cell* 5:1749–1759.
Ling et al. 1991. *Bio/Technology* 9:752–758.
Luciano et al. 1987. *Plant Science* 51:295–303.
Maiss et al. 1989. *J. Gen. Virol.* 70:513–524.
McCuthan et al. 1968. *J. Natl. Cancer Inst.* 41:351.
Melton et al. 1984. *Nucl. Acids Res.* 12:7145–7156.
Messing 1983. "Methods in Enzymology" (R. Wu, L. Grossman, and K. Moldave, eds.). Vol. 101c, pp. 20–78. Academic Press, New York.
Murashige and Skoog 1962. *Plant Physiol.* 15:473–497.
Orkin et al. 1988. *Prog. Med. Genet.* 7:130.
Pang et al. 1993. *Bio/Technology* 11:819–824.
Purcifull and Batchelor, 1977. *Fla. Agric. Exp. Stat. Tech. Bull.* 788.
Reagan et al., 1979. *J. Econ. Entomol.* 72:538–540.
Riechman et al., 1992. *J. Gen. Virol.* 73:1–16.
Robaglia et al., 1989. *J. Gen. Virol.* 70:935–947.
Rogers and Bendich, 1988. in "Plant Molecular Biology Manual" (Gelvin, S. B., and Schilperoort, R. A., Eds.) pp. A6:1–10. Kluwer Academic Publishers, Dordecht, Belgium.
Rothstein et al., 1987. *Gene* 53:153–161.
Sambrook et al., 1989. Molecular cloning: a laboratory manual, 2nd ed. Cold Spring Harbor Laboratories, Cold Spring Harbor, N.Y.
Sanford and Johnston 1985. *J. Theor. Biol.* 113:395–405.

Sanger et al. 1977. *Proc. Natl. Acad. Sci. U.S.A.* 74:5463–5467.
Schafner (1980). *Proc. Natl. Acad. Sci. U.S.A.* 77:2163–2167.
Schmidhauser and Helinski 1985. *J. Bact.* 164:446–455.
Stark and Beachy 1989. *Bio/Technology* 7:1257–1262.
Tabler and Tsagris 1991. *Gene* 100:175–183.
Taylor et al. 1985a. *Nucl. Acids Res.* 13:8749–8764.
Taylor et al. 1985b. *Nucl. ACids Res.* 13:8765–8785.
Towbin et al. 1979. *Proc. Natl. Acad. Sci. U.S.A.* 76:4350–4354.
van der Vlugt et al. 1992. *Plant Molecular Biology* 20:631–639.
Verwoerd et al. 1989. *Nucl. Acids Res.* 17:2372.
Whitty et al. 1994. *Tob. Sci.* 38:30–34.

We claim:

1. A method of producing a transformed plant cell with a reduced capacity to support the expression of a plus-sense RNA virus gene relative to an untransformed plant cell, the method comprising transforming the plant cell with a nucleic acid molecule wherein the nucleic acid molecule comprises a coding sequence operably linked to a promoter sequence, and wherein the coding sequence encodes an untranslatable plus-sense transcript that shares at least 80% nucleotide sequence similarity with a transcript of the plus-sense RNA virus gene.

2. The method of claim 1 wherein the plus-sense RNA virus gene is a potyvirus gene.

3. The method of claim 2 wherein the potyvirus gene is a coat protein gene.

4. The method of claim 1 wherein the plus-sense transcript from the coding sequence of the nucleic acid molecule shares at least 85% nucleotide sequence similarity with the transcript of the plus-sense RNA virus gene.

5. The method of claim 1 wherein the transcript encoded by the coding sequence of the nucleic acid molecule is rendered untranslatable prior to transformation into the plant cell by the introduction of a premature stop codon into the coding sequence.

6. The method of claim 5 wherein the premature stop codon is introduced into the coding sequence within 200 nucleotides of a translation initiation codon in the coding sequence.

7. The method of claim 6 wherein the premature stop codon is introduced into the coding sequence within 50 nucleotides of a translation initiation codon in the coding sequence.

8. A method of producing a transformed plant cell with a reduced capacity to support the expression of a potyvirus gene relative to an untransformed plant cell, the method comprising transforming the plant cell with a nucleic acid molecule wherein the nucleic acid molecule comprises a coding sequence operably linked to a promoter sequence, the coding sequence comprising a premature stop codon within 50 nucleotides of a translation initiation codon and encoding an untranslatable plus-sense transcript that shares at least 85% nucleotide sequence similarity with a transcript of the potyvirus gene.

9. A method of producing a plant with a reduced susceptibility to a plus-sense RNA virus comprising the steps of:
   providing a nucleic acid sequence that shares at least 80% nucleotide sequence similarity with a plus-sense RNA virus gene sequence over a length of at least 100 nucleotides and wherein the nucleic acid sequence encodes a plus-sense RNA molecule;
   modifying the nucleic acid sequence by introducing at least one stop codon or at least one frameshift mutation such that the plus-sense RNA encoded by the modified nucleic acid molecule is untranslatable;
   transforming at least one plant cell with the modified nucleic acid sequence;
   regenerating at least one differentiated plant from the transformed plant cells; and
   selecting a regenerated transformed plant that exhibits reduced susceptibility to the plus-sense RNA virus.

10. A method of producing a plant with a reduced susceptibility to infection by a target plus-sense RNA virus comprising the steps of:
    providing nucleic acid molecules comprising a coding sequence operably linked to a promoter sequence, wherein the coding sequence encodes an untranslatable plus-sense transcript that shares at least 80% nucleotide sequence similarity with a transcript of a gene of the target plus-sense RNA virus;
    transforming plant cells with the nucleic acid molecules;
    growing plants from the transformed plant cells; and
    selecting a transformed plant that shows a reduced susceptibility to infection by the target plus-sense RNA virus.

11. A transformed plant having reduced susceptibility to plus-sense RNA virus infection produced by the method of claim 10.

12. The plant of claim 11 wherein the plant has a reduced susceptibility to potyvirus infection.

13. A progeny plant produced by sexual or asexual reproduction of the plant of claim 11 wherein the progeny plant has a reduced susceptibility to infection by the target plus-sense RNA virus and wherein the progeny plant comprises cells containing at least one nucleic acid molecule according to claim 11.

14. A seed produced by selfing or outcrossing the plant of claim 11 wherein a plant grown from the seed has a reduced susceptibility to infection by the target plus-sense RNA virus and comprises cells containing at least one nucleic acid molecule according to claim 11.

15. The method of claim 10 wherein the target plus-sense RNA virus is a potyvirus.

16. The method of claim 15 wherein the target plus-sense RNA virus gene is a potyvirus coat protein gene.

17. A transformed plant having reduced susceptibility to potyvirus infection produced by the method of claim 15.

18. The method of claim 10 wherein the coding sequence comprises at least one premature stop codon within the first 200 nucleotides of the coding sequence.

19. The method of claim 18 wherein the coding sequence comprises at least one premature stop codon within the first 50 nucleotides of the coding sequence.

20. A recombinant DNA molecule effective to inhibit the expression of a potyvirus virus gene when the recombinant DNA molecule and the potyvirus gene are present in a plant cell, the recombinant DNA molecule comprising a coding sequence operably linked to a promoter sequence wherein the coding sequence encodes an untranslatable plus-sense transcript that shares at least 80% nucleotide sequence similarity with a transcript of a potyvirus gene.

21. A plant transformation vector comprising the DNA molecule of claim 20.

22. A plant cell transformed with the transformation vector of claim 21.

23. A different plant comprising plant cells according to claim 22.

24. The recombinant DNA molecule of claim 20 wherein the coding sequence comprises a premature stop codon within 200 nucleotides of a translation initiation codon.

25. The recombinant DNA molecule of claim 24 wherein the coding sequence comprises a premature stop codon within 50 nucleotides of the translation initiation codon and encodes an untranslatable plus-sense transcript that shares at least 85% sequence homology with a transcript of the virus gene.

26. A plant transformation vector comprising the DNA molecule of claim 25.

27. A plant cell transformed with the transformation vector of claim 26.

28. A differentiated plant comprising plant cells according to claim 27.

29. A recombinant DNA molecule according to claim 20, wherein the untranslatable plus-sense transcript encoded by the coding sequence shares at least 80% nucleotide sequence similarity with a transcript of a potyvirus coat protein gene.

* * * * *

UNITED STATES PATENT AND TRADEMARK OFFICE
CERTIFICATE OF CORRECTION

PATENT NO. : 5,583,021
DATED : December 10, 1996
INVENTOR(S) : Dougherty et al.

It is certified that error appears in the above-identified patent and that said Letters Patent is hereby corrected as shown below:

On the title page, item [56],

<u>In the References Cited:</u>

Please insert the following omitted references:

--5,034,323  7/1991  Jorgensen et al.--.

--5,283,184  2/1994  Jorgensen et al.--.

<u>In the Other Publications:</u>

"siquence" should read --Sequence--.

Column 5, line 28, "$R_1$, generation)." should read --$R_1$ generation).--.

Column 5, line 47, "polymerass" should read --polymerase--.

Column 8, line 48, "kNA" should read --RNA--.

Column 15, line 12, "050 µg/ml" should read --500 µg/ml--.

Column 16, line 20, ":02 gm" should read --:0.2gm--.

Column 18, line 6, "vital" should read --viral--.

UNITED STATES PATENT AND TRADEMARK OFFICE
CERTIFICATE OF CORRECTION

PATENT NO. : 5,583,021
DATED : December 10, 1996
INVENTOR(S) : Dougherty et al.

It is certified that error appears in the above-identified patent and that said Letters Patent is hereby corrected as shown below:

Column 18, line 28, "2.2 Materials and Methods Construction of DNA Molecules" should read --2.2 Materials and Methods--.

Column 18, line 29, and Generation of Transgenic plants" should read --Construction of DNA Molecules and Generation of Transgenic plants--.

Column 19, line 19, "stm." should read --stem--.

Column 20, line 52, "Response of 2RC lines to virus infection Transgenic 2RC" should read --Response of 2RC lines to virus infection--.

Column 20, line 52, "plants were screened for virus . . . ." should appear as follows:

-- Transgenic 2RC plants were screened for virus resistance . . . . coat protein (Lindbo et al. 1993b).--.

Column 21, line 46, "responsees" should read --responses--.

Column 24, line 55, "was" should read --with--.

UNITED STATES PATENT AND TRADEMARK OFFICE
CERTIFICATE OF CORRECTION

PATENT NO. : 5,583,021

DATED : December 10, 1996

INVENTOR(S) : Dougherty et al.

It is certified that error appears in the above-identified patent and that said Letters Patent is hereby corrected as shown below:

Column 25, line 36, "expressed. Transgenic plants expressing either a ΔC118" should read --expressed. Transgenic plants expressing a ΔC118--.

Column 25, line 52, "injection" should read --infection--.

Column 25, line 59, "F1-3.3" should read --FL 3.3--.

Column 25, line 60, "F1-24.3" should read --FL-24.3--.

Column 27, line 19, "F1-3.3" should read --FL-3.3--.

Column 27, line 20, "F1-24.3" should read --FL-24.3--.

Column 29, line 31, "presented i FIG. 7." should read --presented in FIG. 7.--.

Column 30, line 46, "Tobacco" should read --Potato--.

Column 32, line 42, "polymerass" should read --polymerase--.

Column 33, line 5, "ENA" should read --RNA--.

Column 33, line 7, "RA" should read --RNA--.

UNITED STATES PATENT AND TRADEMARK OFFICE
CERTIFICATE OF CORRECTION

PATENT NO. : 5,583,021

DATED : December 10, 1996

INVENTOR(S) : Dougherty et al.

It is certified that error appears in the above-identified patent and that said Letters Patent is hereby corrected as shown below:

Column 36, line 1, "*ACids*" should read --*Acids*--.

Column 66, line 31, "different" should read --differentiated--.

Signed and Sealed this

Fourteenth Day of April, 1998

Attest:

BRUCE LEHMAN

*Attesting Officer*    *Commissioner of Patents and Trademarks*